(12) United States Patent
Taylor et al.

(10) Patent No.: US 8,101,408 B2
(45) Date of Patent: Jan. 24, 2012

(54) INSECTICIDAL EXTRACT FROM LEGUME PLANTS AND METHOD OF PREPARING THE SAME

(75) Inventors: Wesley G. Taylor, Saskatchewan (CA); Paul G. Fields, Manitoba (CA); Daniel H. Sutherland, Saskatchewan (CA)

(73) Assignee: Her Majesty the Queen in right of Canada, as represented by the Minister of Agriculture and Agri-Food, Saskatoon, Saskatchewan (CA)

( * ) Notice: Subject to any disclaimer, the term of this patent is extended or adjusted under 35 U.S.C. 154(b) by 0 days.

(21) Appl. No.: 12/481,106

(22) Filed: Jun. 9, 2009

(65) Prior Publication Data

US 2010/0009912 A1  Jan. 14, 2010

Related U.S. Application Data

(62) Division of application No. 11/088,684, filed on Mar. 24, 2005, now abandoned.

(51) Int. Cl.
*A61K 36/48*  (2006.01)
*C12N 5/07*  (2010.01)
*A61N 65/00*  (2006.01)
*A23L 1/20*  (2006.01)
*A01N 37/18*  (2006.01)
*C11B 1/10*  (2006.01)

(52) U.S. Cl. .......... 435/348; 424/405; 426/46; 514/4.5; 530/370; 554/9; 554/12; 554/13; 554/15

(58) Field of Classification Search .................. None
See application file for complete search history.

(56) References Cited

U.S. PATENT DOCUMENTS

| 3,666,776 | A | 5/1972 | Dachs |
| 4,602,003 | A | 7/1986 | Malinow |
| 5,955,082 | A | 9/1999 | Bodnaryk et al. |
| 2002/0115623 | A1 | 8/2002 | Wu et al. |

FOREIGN PATENT DOCUMENTS

WO   1999/58695 A2   11/1999

OTHER PUBLICATIONS

Taylor, W.G.; Zulyniak,H.J.; Richards, K.W.;Acharya,S.N.; Bittman, S.; and Elder, J.L. "Variation in Diosgenin Levels among 10 Accessions of Fenugreek Seeds Produced in Western Canada" J. Agric. Food Chem.,2002,50(21), pp. 5994-5997.*

(Continued)

*Primary Examiner* — Christopher R Tate
*Assistant Examiner* — Aaron Kosar
(74) *Attorney, Agent, or Firm* — Ronald I. Eisenstein; Nixon Peabody LLP

(57) ABSTRACT

The invention may be summarized as follows. The present invention provides insecticides comprised of naturally-occurring compounds, such as, for example, PA1b-related peptides and terpenoid saponins. The present invention also provides for identification and characterization of a synergistic insecticidal effect between peptides and saponins extracted from plants. Furthermore, simplified extraction procedures are provided that avoid the use of a chloroform defatting step or a column chromatography step.

8 Claims, 31 Drawing Sheets

OTHER PUBLICATIONS

Chung Y.C., et al "Antioxidative activity and safety of the 50 ethanolic extract from red bean fermented by *Bacillus subtilis* IMR-NK1" J Agric Food Chem. Apr. 10, 2002,50(8),pp. 2454-2458. (Abstract only).*

Taylor, W.G.; Fields, P.G.;and Sutherland, D.H. "Fractionation of Lentil Seeds (*Lens culinaris* Medik.) for Insecticidal and Flavonol Tetraglycoside Components" J. Agric. Food Chem., 2007,55(14), pp. 5491-5498.*

DianasKitchen.com, Jun. 20, 2000, <URL:http://www.dianaskitchen.com/page/poultry/tequila.htm>, accessed Nov. 19, 2010, 1 page.*

Amarowicz, R. et al., Grasas y Aceites, 52(2):89-93 (2001). "Influence of the extraction procedure on the antioxidative activity of lentil seed extracts in a beta-carotene linoleate model system."

Fonseca, H. and Regitano-D'Arce, M.A.B., Scientia Agricola, 50(1):154-6 (1993). "Aflatoxin removal of peanut meals with aqueous ethanol."

Gressent, F. et al., Eur. J. Biochem., 270:2429-2435 (2003).

Higgins, T.J.V. et al., The Journal of Biological Chemistry, 261(24):11124-11130 (1986).

Kalaichelvan, P.T. and Mahadevan, A., Indian Phytopathology, 41(4):581-5 (1988). "Distribution of prohibitins in groundnut: I. Solvent effects and phenol estimation."

Louis, S. et al., Plant Science, 167:705-714 (2004).

Revilleza, M.J.R., Plant Foods for Human Nutrition, 40(1):83-94 (1990). "Oligosaccharides in several Philippine indigenous food legumes determination localization and removal."

Rudinger, J., Peptide Hormones, JA Parsons, Ed. 1-7 (1976).

SIGMA. Designing Custom Peptides. http://www.sigmaaldrich.com/Brands/Sigma_Genosys/Custom_Peptides/Key_Resources/Designing_Peptides.html (Accessed May 31, 2007), 2 pages.

Taylor, W. et al., Journal of Agricultural and Food Chemistry, 52:7484-7490 (2004).

Taylor, W. et al., Journal of Agricultural and Food Chemistry, 52:7491-7498 (2004).

Taylor, W. et al., Journal of Agricultural and Food Chemistry, 52:7499-7506 (2004).

Watanabe, Y. et al., Eur. J. Biochem., 224:167-172 (1994).

Yamazaki, T. et al., Eur. J. Biochem., 270:1269-1276 (2003).

* cited by examiner

```
            5        10       15       20       25       30       35
a    ASCNGVCSPFDIPPCGSPLCRCIPVGLVIGKCRNPYG (4)  3788
     ASCNGVCSPFDMPPCGTSACRCIPAGLFIGKCRNPYG (10)

b    ASCNGVCSPFEMPPCGSSACRCIPAGLFIGKCRNPYG (11)
     ASCNGVCSPFEIPPCGTPLCRCIPAGLVIGKCRNPYG (12)

c    ISCNGVCSPFDIPPCGSPACRCIPVGLVIGKCRNPYG (13)
     VSCNGVCSPFDIPPCGSPLCRCIPAGLVIGKCRNPYG (3)
     VSCNGVCSPFDIPPCGTPACRCIPVGLVIGKCRNPYG (14)
     ISCNGVCSPFEIPPCGTPACRCIPAGLVIGKCRNPYG (15)
     VSCNGVCSPFEIPPCGSPACRCIPVGLVIGKCRNPYG (16)

d    ASCNGVCSPFDMPPCGSSACRCIPVGLFIGNCRNPYG (17)
     VSCNGVCSPFDMPPCGSSACRCIPAGLFIGNCRNPYG (18)
     ASCNGVCSPFEMPPCGTSACRCIPAGLFIGNCRNPYG (19)
     ISCNGVCSPFDIPPCGSPLCRCIPAGLVIGNCRNPYG (1)  PA1b
     ISCNGVCSPFDIPPCGTPACRCIPVGLVIGNCRNPYG (20)
     ASCNGVCSPFDIPPCGTPLCRCIPVGLVIGNCRNPYG (21)
     VSCNGVCSPFDIPPCGTPLCRCIPAGLVIGNCRNPYG (22)
     ISCNGVCSPFEIPPCGSPACRCIPVGLVIGNCRNPYG (23)
     ASCNGVCSPFEIPPCGSPLCRCIPVGLVIGNCRNPYG (24)
     VSCNGVCSPFEIPPCGSPLCRCIPAGLVIGNCRNPYG (25)
     VSCNGVCSPFEIPPCGTPACRCIPVGLVIGNCRNPYG (26)

e    ISCNGVCSPFDIPPCGSPLCRCIPVGLFIGNCRNPSG (27)
     VSCNGVCSPFDIPPCGTPLCRCIPVGLFIGNCRNPSG (28)
     ISCNGVCSPFEIPPCGTPLCRCIPAGLFIGNCRNPSG (29)
     VSCNGVCSPFEIPPCGSPLCRCIPVGLFIGNCRNPSG (30)
     ISCNGVCSPFDIPPCGTPLCRCIPAGLFIGKCRNPSG (31)
     VSCNGVCSPFDIPPCGSPLCRCIPVGLFIGKCRNPSG (32)
     ISCNGVCSPFEIPPCGSPLCRCIPAGLFIGKCRNPSG (33)
     ISCNGVCSPFEIPPCGTPACRCIPVGLFIGKCRNPSG (34)
     ASCNGVCSPFEIPPCGTPLCRCIPVGLFIGKCRNPSG (35)
     VSCNGVCSPFEIPPCGTPLCRCIPAGLFIGKCRNPSG (36)
```

Fig. 18

```
              5         10        15        20        25        30        35
a     ASCNGVCSPFEmPPCGTSACRCIPVGLVIGYCRNPSG (6)    3757
      ASCNGVCSPFEmPPCGSSLCRCIPAGLVIGYCRNPSG (37)
      ASCNGVCSPFDmPPCGTSLCRCIPAGLVIGYCRNPSG (38)

b     ISCNGVCSPFEmPPCGSSACRCIPAGLVIGYCRNPSG (39)
      VSCNGVCSPFEmPPCGTSACRCIPAGLVIGYCRNPSG (40)
      ISCNGVCSPFDmPPCGTSACRCIPAGLVIGYCRNPSG (41)
      VSCNGVCSPFDmPPCGSSACRCIPVGLVIGYCRNPSG (42)
```

Fig. 19

```
             5        10        15        20        25        30        35
a    ASCNGVCSPFEmPPCGTSACRCIPVGLFIGYCRNPSG (7)   3805
     ASCNGVCSPFEmPPCGSSLCRCIPAGLFIGYCRNPSG (43)
     ASCNGVCSPFDmPPCGTSLCRCIPAGLFIGYCRNPSG (44)

b    ISCNGVCSPFEmPPCGSSACRCIPAGLFIGYCRNPSG (45)
     VSCNGVCSPFEmPPCGTSACRCIPAGLFIGYCRNPSG (46)
     ISCNGVCSPFEIPPCGTPLCRCIPAGLVIGYCRNPSG (47)
     VSCNGVCSPFEIPPCGSPLCRCIPVGLVIGYCRNPSG (48)
     ISCNGVCSPFDmPPCGTSACRCIPAGLFIGYCRNPSG (49)
     VSCNGVCSPFDmPPCGSSACRCIPVGLFIGYCRNPSG (50)
     ISCNGVCSPFDIPPCGSPLCRCIPVGLVIGYCRNPSG (51)
     VSCNGVCSPFDIPPCGTPLCRCIPVGLVIGYCRNPSG (52)

c    ASCNGVCSPFEmPPCGTSACRCIPAGLVIGYCRNPYG (53)
     ASCNGVCSPFDmPPCGSSACRCIPVGLVIGYCRNPYG (54)
     VSCNGVCSPFDmPPCGSSACRCIPAGLVIGYCRNPYG (55)
```

Fig. 20

```
                  5        10       15       20       25       30       35
a       ASCNGVCSPFEmPPCGSSACRCIPVGLVVGYCRHPSG (5)      3752
        ASCNGVCSPFDmPPCGTSACRCIPVGLVVGYCRHPSG (56)
        ASCNGVCSPFDmPPCGSSLCRCIPAGLVVGYCRHPSG (57)

b       VSCNGVCSPFEmPPCGSSACRCIPAGLVVGYCRHPSG (58)
        VSCNGVCSPFDmPPCGTSACRCIPAGLVVGYCRHPSG (59)
        ISCNGVCSPFDmPPCGSSACRCIPAGLVVGYCRHPSG (60)
```

```
                    1    5       10       15      20      25    30      35 37
PA1b (3788)         I S C N G V C S P F D I P P C G S P L C R C I P A G L V I G N C R N P Y G   (1)
Variant                 A               E M       T S A       Y   F   Y           S            (2)
substitutions           V                                     V       K                        (3)

3788                    A               D I       S P L       V   V   K           Y            (4)
(iso PA1b)

3752                    A               E m       S S A       V   V V Y       H   S            (5)

3757                    A               E m       T S A       V   V   Y           S            (6)

3805                    A               E m       T S A       V   F   Y           S            (7)

Protéine PT             A               E M       T S A       V   V   Y           S            (8)
(3741)

Leginsulin          A D       A         E V       R S R D     V I F V F   I H     T            (9)
(3919)
```

Fig. 23

INSECTICIDAL EXTRACT FROM LEGUME PLANTS AND METHOD OF PREPARING THE SAME

CROSS-REFERENCE TO RELATED APPLICATION

This application is a Divisional of U.S. patent application Ser. No. 11/088,684 filed on Mar. 24, 2005, the contents of which are incorporated herein by reference.

FIELD OF INVENTION

The present invention relates to an insecticidal composition that comprises compounds that occur naturally in legumes. The present invention further relates to a method of isolating the compounds from their natural source or setting. More particularly, the present invention relates to a legume extract comprising an insecticidal peptide, saponin, or a combination thereof.

BACKGROUND OF THE INVENTION

Insects have been a problem for crops and stored food products since the dawn of agriculture. Since the 1950's synthetic insecticides have been the method of choice to control insect infestations in crop fields, stored grain, warehouses and food processing facilities. However, there are several reasons that alternatives to synthetic insecticides are required. Insects have developed resistance to several synthetic insecticides. Many consumers want no insecticide residues on their food. The application of synthetic insecticides has become more onerous. For example, the fumigant aluminum phosphide in the U.S.A. has a new label which requires more sampling of product and greater notification of the public.

Some insecticides are being phased out because they are harmful to the environment. Methyl bromide, widely used as a fumigant, is an ozone-depleting substance that will be banned after 2005 in most countries. Phosphine, the most widely used grain fumigant, is also being restricted in its use. New protectants are needed that are safe for humans and the environment.

To control insects there are a number alternatives to synthetic insecticides; physical, biological, or botanical. Botanical insecticides have a long history of use in agricultural product protection. Pyrethrums, usually synergized with piperonyl butoxide, are used extensively commercially to control stored-product insects. Neem has been used for centuries in India in stored grain. However, other than spices, food plants have not been widely used to control insects.

It has long been known that legume seeds contain a wide range of chemicals with toxic or deterrent effects against insect pests. For example, pea seeds (Pisum sativum L.) and their extracts are toxic to many insects, especially Sitophilus spp. (Bodnaryk et al, U.S. Pat. No. 5,955,082, issued Sep. 21, 1999; Delobel et al, PCT publication WO99/58695 published Nov. 18, 1999). A multigenic family of small linear, 37-amino acid peptides, was isolated from peas (Higgins et al., 1986) and variants of this cysteine-rich pea albumin (PA1b) were found to be toxic to stored-product insects and aphids (Delobel et al., WO99/58695). Delobel et al. isolated from peas and sequenced an insecticidal variant of PA1b with a mass of 3741 Da. Gressent et al., 2003) have studied the binding of this 3741 variant to microsomal fractions of wheat-feeding and pea feeding weevils. Other legume seeds have been studied genetically for the presence of insect-toxic seed albumins (Louis et al., 2004).

Bodnaryk et al. (U.S. Pat. No. 5,955,082) developed an extraction procedure comprising treatment steps using chloroform and hot 80% methanol to obtain crude insecticidal pea extracts. The aqueous methanol extracts from defatted, protein-rich flour were partially purified with reversed phase C8 silica. Activity was found in fractions obtained by elution of the C8 silica column with methanol. These C8 extracts displayed insecticidal and antifeedant activity against rice weevil [Sitophilus oryzae (L.)] and other stored-product insects but the active ingredients of C8 extracts were not identified. Furthermore, the use and disposal of chloroform is expensive, and insecticides containing residual chloroform may be of limited use, particularly with regard to food-grade crops or products. The use of column chromatography is also expensive and may limit industrial scale-up.

Sitophilus spp., S. granarius (L.), S. oryzae (L.) and S. zeamais Motschulsky, are examples of serious, cosmopolitan pests of stored cereals. Previous work has shown that mixing pea seed with wheat seed at a ratio of 1:1 reduced S. oryzae populations by 70%. However, mixing equal weights of whole peas and wheat is not a practical means for controlling pests.

None of the previous approaches has been adapted for industrial use in controlling insects.

Thus, there is a need for alternative natural extracts and methods of preparing the same, for controlling insect spoilage of agricultural products.

SUMMARY OF THE INVENTION

The present invention relates to an insecticidal composition that comprises compounds that occur naturally in legumes. The present invention further relates to a method of isolating the compounds from their natural source or setting. More particularly, the present invention relates to a legume extract comprising an insecticidal peptide, saponin, or a combination thereof.

It is an object of the invention to provide an insecticidal composition and a process for preparing the same.

According to the present invention there is provided an insecticidal, alcohol-soluble extract of a non-defatted legume seed material, the extract comprising an insecticidal peptide to saponin ratio ranging from 10:1 to 1:10. As an example, the extract may comprise at least one PA1b-related peptide comprising a sequence that is at least 70% identical to an amino acid sequence selected from the group consisting of: SEQ ID NO:1, SEQ ID NO:2, SEQ ID NO:3, SEQ ID NO:4, SEQ ID NO:5, SEQ ID NO:6, SEQ ID NO:8, and SEQ ID NO:9. In another example, the saponin may be a triterpenoid saponin and may further, be selected from the group consisting of: soyasaponin I, soyasaponin II, soyasaponin III, soyasaponin VI, dehydrosoyasaponin I, echinocystic acid 3-glucoside, glycyrrhizic acid, hederacoside C, beta-escin, and alpha-hederin.

According to the present invention there is provided a method of preparing an insecticidal alcohol soluble legume extract comprising: extracting a non-defatted legume seed material with a lower molecular weight alcohol, for example C(1-4) alcohol. Methods of the present invention may further comprise precipitating the alcohol soluble extract with an organic acid.

In an example of the method of the present invention the organic acid may be selected from the group consisting of: benzoic, acetic, trichloroacetic, trifltioroacetic, sorbic, citric, formic, and propionic acids.

According to the present invention there is provided an insecticidal composition comprising an isolated PA1b-related peptide and an isolated saponin, the peptide to saponin ratio ranging from 10:1 to 1:10. In an example of the insecticidal composition of the present invention the PA1b-related peptide comprises a sequence that is at least 70% identical to an amino acid sequence selected from the group consisting of: SEQ ID NO: 1, SEQ ID NO:2, SEQ ID NO:3, SEQ ID NO:4, SEQ ID NO:5, SEQ ID NO:6, SEQ ID NO:8, and SEQ ID NO:9. In another example, the saponin is a triterpenoid saponin, and may optionally be selected from the group consisting of: soyasaponin I, soyasaponin II, soyasaponin III, soyasaponin VI, dehydrosoyasaponin I, echinocystic acid 3-glucoside, glycyrrhizic acid, hederacoside C, beta-escin, and alpha-hederin.

According to the present invention there is provided a method of controlling insects comprising exposing the insects to an effective amount of an extract or composition of the present invention. In an example, the composition or extract may comprise dehydrosoyasaponin I.

According to the present invention there is provided an insecticidal alcohol soluble plant extract comprising a PA1b-related peptide. By "PA1b-related peptide" is meant any peptide that comprises a sequence that is at least 60%, 62%, 64%, 66%, 68%, 70%, 72%, 74%, 76%, 78% or 80% identical to any one of the sequences represented in FIGS. 18-21 and 23 (SEQ ID Nos:1-60), and exhibits insecticidal activity alone or in combination with a saponin.

In an example of the present invention, a PA1B-related peptide comprises an amino acid sequence of Cys-(Xaa)n-(Xaa) n-Cys-(Xaa) n-Pro-(Xaa)n-(Xaa) n-Pro-Cys-(Xaa)n-(Xaa)n-Cys-(Xaa)n-Cys-(Xaa) n-Pro-(Xaa)n-(Xaa)n-(Xaa) n-Cys (SEQ ID NO:63), where each Xaa is independently selected from any amino acid and each n independently equals 1, 2, 3, 4, or 5. In another example of the present invention, a PA1B-related peptide comprises an amino acid sequence of Cys-(Xaa) n-(Xaa)n-Cys-(Xaa)n-Pro-(Xaa)n-(Xaa) n-Pro-Pro-Cys-(Xaa) n-Xaa)n-Cys-(Xaa)n-Cys-(Xaa) n-Pro-(Xaa)n-(Xaa)n-(Xaa) n-Cys-(Xaa)n-Pro (SEQ ID NO:64), where each Xaa is independently selected from any amino acid and each n independently equals 1, 2, 3, 4, or 5. In again another example of the present invention, a PA1B-related peptide comprises an amino acid sequence of Cys-Xaa-Xaa-(Xaa)n-Cys-Xaa-Pro-Xaa-(Xaa)n-Xaa-Xaa-Pro-Cys-Xaa-Xaa-Xaa-(Xaa)n-Cys-Xaa-Cys-Xaa-Pro-Xaa-(Xaa) n-Xaa-Xaa-Xaa-Xaa-(Xaa) n-Cys (SEQ ID NO:65), where each Xaa is independently selected from any amino acid and each n independently equals 0, 1, 2, 3, or 4. In still another example of the present invention, a PA1B-related peptide comprises an amino acid sequence of Cys-Xaa-Xaa-(Xaa)n-Cys-Xaa-Pro-Xaa-(Xaa)n-Xaa-Pro-Pro-Cys-Xaa-Xaa-Xaa-(Xaa)n-Cys-Xaa-Cys Xaa-Pro-Xaa-(Xaa)n-Xaa-Xaa-Xaa-Xaa-(Xaa)n-Cys-(Xaa)n-Xaa-Pro (SEQ ID NO:66), where each Xaa is independently selected from any amino acid and each n independently equals 0, 1, 2, 3, or 4. In yet another example of the present invention, a PA1B-related peptide comprises an amino acid sequence of Cys-Xaa-Xaa-(Xaa)n-Cys-Ser-Pro-Phe-(Xaa) n-Xaa-Pro-Pro-Cys-Xaa-Xaa-Xaa-(Xaa)n-Cys-Xaa-Cys-Xaa-Pro-Xaa-(Xaa)n-Leu-Xaa-(Xaa)n-Gly-Xaa-Cys-(Xaa)n-Xaa-Pro (SEQ ID NO:67), where each Xaa is independently selected from any amino acid, and each n independently equals 0, 1, 2, 3, or 4. It will be understood that each n independently indicates multiples of an Xaa residue. For example, where n equals zero an Xaa residue is removed, where n equals one a single residue is represented, where n equals two a double Xaa sequence is represented with each Xaa being independently selected from any amino acid, where n equals three a triple Xaa sequence is represented with each Xaa being independently selected from any amino acid, etc. In a further example, a PA1B-related peptide comprises an amino acid sequence having the general formula X1-C-X2-C-X3-C-X4C-X5-C-X6C-X7 as previously defined in WO99/58695 (Delobel et al.).

Alcohols for use with the present invention, may be empirically determined by persons skilled in the art. As an example lower molecular weight alcohols may be used. In further examples the alcohol may be selected from the group consisting of methanol, ethanol, n-propanol, isopropanol, n-butanol, tert-butanol, 1-isobutanol, and 2-buten-1-ol. Use of ethanol may be advantageous in regards to insecticidal protection of food-grade crops and products. In still another example, the alcohol is an about 50-98% aqueous solution of the alcohol, and may optionally be an about 60-95% aqueous solution of the alcohol. The temperature of the alcohol is not critical to the present invention.

There are potential commercial applications of this invention for control of insects attacking stored grains in home, farm or elevator locations and on ships. Worldwide, there is a great deal of interest in developing botanical or natural insect control products, especially from food grade materials. The combination of field peas as a raw material source and aqueous alcohol as extraction solvent should be attractive to industry.

The methods, extracts, or compositions of the present invention might find considerable utility in, or when exporting grain to, warmer areas of the world inhabited by major storage pests, for example the rice weevil.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 18 shows sequences (labeled as groups a-e) of pea peptides with an average molecular mass of 3788 Daltons. The top sequence was that found for the isolated 3788 peptide. For comparison, the sequence of the isobaric PA1b described by Higgins et al. (1986, *J. Biol. Chem.*, 261: 11124-11130) is also indicated. SEQ ID NOs are indicated in brackets at the right of each sequence.

FIG. 19 shows sequences (groups a-b) of pea peptides with an average molecular mass of 3757 Daltons. SEQ ID NOs are indicated in brackets at the right of each sequence.

FIG. 20 shows sequences (groups a-c) of pea peptides with an average molecular mass of 3805 Daltons. SEQ ID NOs are indicated in brackets at the right of each sequence.

FIG. 21 shows sequences (groups a-b) of pea peptides with an average molecular mass of 3752 Daltons. SEQ ID NOs are indicated in brackets at the right of each sequence.

FIG. 23 shows a sequence of PA1b (3788 average molecular mass) with allowed sites of amino acid substitution (boldface letters), possible amino acids of PA1b variants as described by Higgins et al. (1986, supra) and sequences, determined by MALDI mass spectrometry, of the four isolated variants with their indicated molecular masses. The sequence of protein PT (calculated average molecular mass of 3741 Daltons) is taken from Delobel et al. (WO99/58695) and the sequence of leginsulin (calculated average molecular mass of 3926 Daltons) is taken from Watanabe et al. (1994, *Eur. J. Biochem.*, 224:167-172). SEQ ID NOs are indicated in brackets at the right of each sequence.

DETAILED DESCRIPTION

Figure 1:
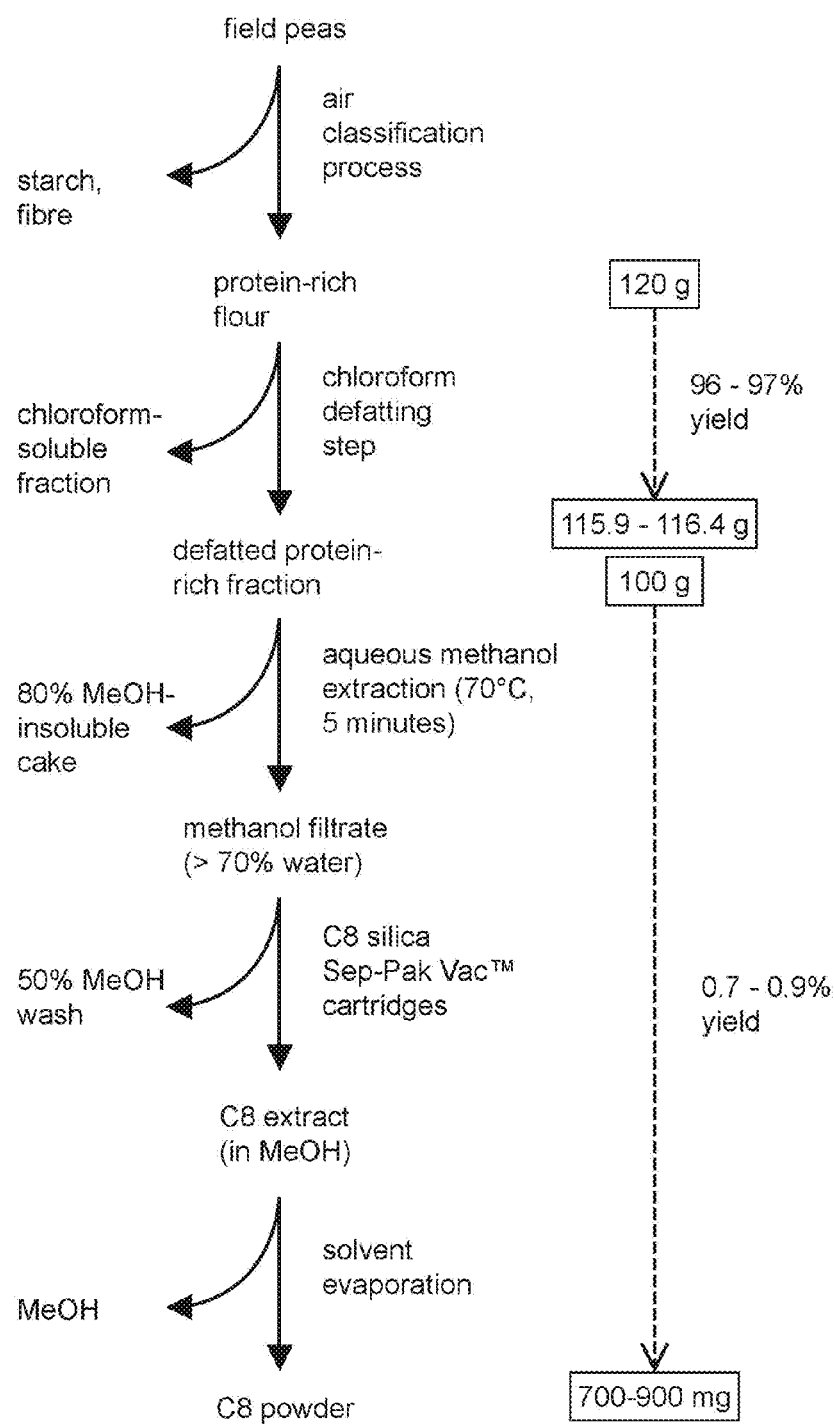
FIG. 1 shows an example of processing steps and yields obtained in an isolation of insecticidal C8 extracts by methods from Bodnaryk et al. (U.S. Pat. No. 5,955,082).

The present invention relates to an insecticidal composition that comprises compounds that occur naturally in legumes. The present invention further relates to a method of isolating the compounds from their natural source or setting. More particularly, the present invention relates to a legume extract comprising insecticidal peptides and soyasaponins.

The following description is of a preferred embodiment.

The present invention pertains to naturally-occurring insecticidal compounds. The insecticidal compounds of the present invention are isolated from their natural setting. However, insecticidal compounds need not be separated from all other compounds in order to be used in the context of the present invention. For example, without limitation, complete or partially purified insecticidal compounds are considered to be isolated from their natural setting and are contemplated for use in controlling insect pests. As another non-limiting example, insecticidal compounds, such as PA1b-related peptides and triterpenoid saponins synthesized using conventional biological or chemical techniques are also considered to be isolated from their natural setting. As yet another example, PA1b-related peptides or triterpenoid saponins obtained from prokaryotic or eukaryotic cells, engineered to produce these compounds, are also considered to be isolated from their natural setting.

Accordingly, peptides and saponins of the invention may be isolated together, for example when using an alcohol extraction method of the present invention or peptides and saponins may be produced separately and/or purified to be separate. Regardless of whether peptides and saponins are isolated together or separately, they may be mixed or added to each other in accordance with peptide to saponin ratios of the present invention to obtain a desired insecticidal activity.

The present invention provides a composition of natural products or natural product mixtures isolated from plants, for example, legumes, that have utility to control insect pests. The Leguminosae Family (also as Fabaceae Family) is one of the largest in the plant kingdom with about 650 genera and over 18,000 species. Examples of legume seeds include, without limitation, mung bean, lima bean, kidney bean, soyabean, peanut, chick pea, pea, lentil, or alfalfa. A non-limiting example of a pea is a yellow field pea (*Pisum sativum* L.).

The present invention provides novel extracts that are shown to control insecticidal activity. Naturally occurring compounds isolated from chemically impure extracts (C8 extracts) for example, protein-containing fractions, saponin-containing fractions or their mixtures are shown to control insect activity. Furthermore, various active ingredients and combinations of active ingredients are discovered and herein disclosed by separation, identification and remixing of legume extracts.

The bioactivity of separated fractions was determined primarily by a flour disk antifeedant bioassay with the rice weevil (*Sitophilus oryzae*), an insect pest of stored products. However, the specific bioassay and test insect is not critical to the present invention, and any conventional bioassay may be used to test or optimize the present invention and the methods and products of the present invention may be used with respect to any insect of interest.

The present invention provides naturally-occurring legume plant extracts that can be obtained by treating plant material with alcohol. The alcohol is preferably a low molecular weight alcohol, such as methanol, ethanol, n-proponal, isopropanol, 2-propen-1-ol (allyl alcohol), n-butanol, tert-butanol, 1-isobutanol, 2-buten-1-ol (crotyl alcohol), or tert-pentanol. For example, legume seed flour may be treated with an alcohol of 1 to 4 carbons to obtain an extract having insecticidal activity. Examples of C(1-4) alcohols include, without limitation, methanol, ethanol, n-butanol, or tert-butanol. Treatment of plant flour with methanol, ethanol, or n-butanol is shown in the Examples. However, other alcohols, and other organic solvents known to extract peptides, saponins or both peptides and saponins may be used. Alcohols or other organic solvents that are non-toxic to humans, for example ethanol, may be advantageously used in preparing an insecticidal composition intended for protection of a food-grade crop or product.

Alcohols for use with the present invention, may be empirically determined by persons skilled in the art. As an example lower molecular weight alcohols may be used. In further examples, the alcohol is an about 50-98% aqueous solution of the alcohol, and may optionally be an about 60-95% aqueous solution of the alcohol.

The temperature of an alcohol treatment is not critical to the present invention and alcohol treatment may be carried out at room temperature or the temperature of an alcohol may be different than room temperature. For example, useful insecticidal components may be extracted using alcohol that varies from 15 degrees C. to 90 degrees C. Persons skilled in the art will recognize advantages to elevating or decreasing alcohol temperature. For example, increasing alcohol above room temperature, such as a range from about 40 to 85 degrees C., may shorten the time of an extraction step.

Previous methods (U.S. Pat. No. 5,955,082, Bodnaryk et al.) for obtaining insecticidal extracts from plant flour have taught the use of a chloroform treatment step to remove lipids and produce a defatted flour extract. The present inventors have surprisingly found that alcohol extraction of a non-defatted or a lipid-containing starting plant material can produce the insecticidal compounds of the present invention. Accordingly, the use of chloroform to defat or remove lipids from plant starting material is not required. Absence of a chloroform treatment step provides for methods of production that are less expensive, more suited to industrial scale-up, and avoids concerns regarding residual chloroform in insecticidal extracts or compositions. In the present invention, by the term "non-defatted" is meant an absence of treatment or extraction with chloroform for the purposes of removing lipids from a plant material.

U.S. Pat. No. 5,955,082 also discloses the use of silica column chromatography for purifying insecticidal compounds. Similar to the use of chloroform, the use of column chromatography also presents concerns with regards to expense and industrial scale-up. The present invention provides a technique to avoid the use of silica columns by treating alcohol extracts of plant material with a precipitating agent. Any precipitating agent known in the art, that is capable of precipitating the insecticidal components of the present invention may be used. Acetonitrile, acetone, ammonium chloride, zinc sulfate, sodium chloride, sodium hydroxide or organic acids are non-limiting representative examples of a precipitating agent. For example, the present inventors have shown that insecticidal components may be precipitated from alcohol extracts by using an organic acid solvent that is soluble or slightly soluble in water. Any conventional water-soluble organic acid that is capable of precipitating the insecticidal components of the present invention may be used, including without limitation, benzoic, acetic, trichloroacetic, trifluoroacetic, sorbic, citric, formic, or propionic acids. For example, after alcohol extraction of pea flour, the alcohol may be evaporated and residue remaining after evaporation can be suspended in acetic acid. The present inventors have found that precipitates from acetic acid, for example those derived from acetic acid treatment of crude ethanol extracts, demonstrate insecticidal activity. Furthermore, the acetic acid precipitates have been found to comprise not only insecticidal peptides but also soyasaponins and lysolecithins. Use of acetic, benzoic, citric, propionic, or sorbic acids are all approved for use in foods, and therefore may be particularly advantageous with respect to insecticidal compositions intended for protection of food-grade crops or products.

The present invention provides insecticidal peptides, insecticidal peptide-containing extracts, saponins, saponin-containing extracts or mixtures thereof that have insecticidal activity. A non-limiting example of insecticidal peptides are PA1b-related peptides, for example SEQ ID NOs:1-9. Non-limiting examples of saponins are triterpenoid saponins. A composition comprising an insecticidal peptide or a saponin may be used as an insecticide. Furthermore, a composition comprising both an insecticidal peptide and a saponin may be used. It will be recognized that an insecticidal peptide may be isolated from the same or different plant material used for isolation of a saponin. Furthermore, an insecticidal peptide and a saponin may be separately isolated from the same plant material, for example, by treatment with a precipitating agent that selectively precipitates an insecticidal peptide or a saponin. It will be further recognized that separately isolated insecticidal peptides and saponins may be mixed to achieve a desired insecticidal activity.

Figure 25:
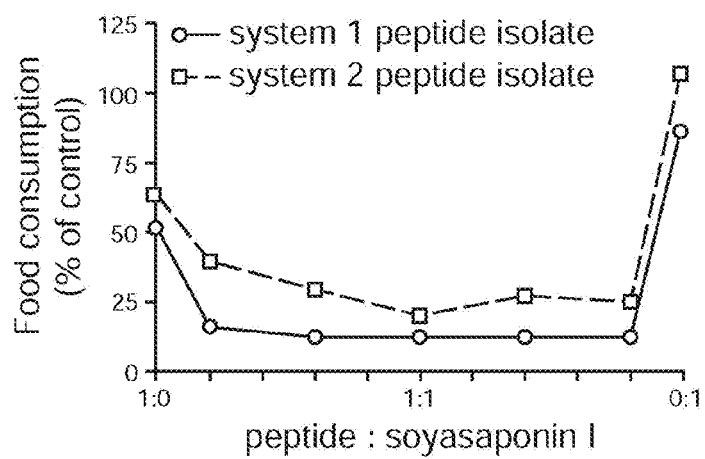
FIG. 25 shows a comparison of antifeedant activity against *S. oryzae* of system 1 and system 2 peptide isolates from flash chromatography when mixed with soyasaponin I (purified by methods a, c, b and d) in various proportions. The total dose was 1.6 mg/200 mg flour.
Figure 26:
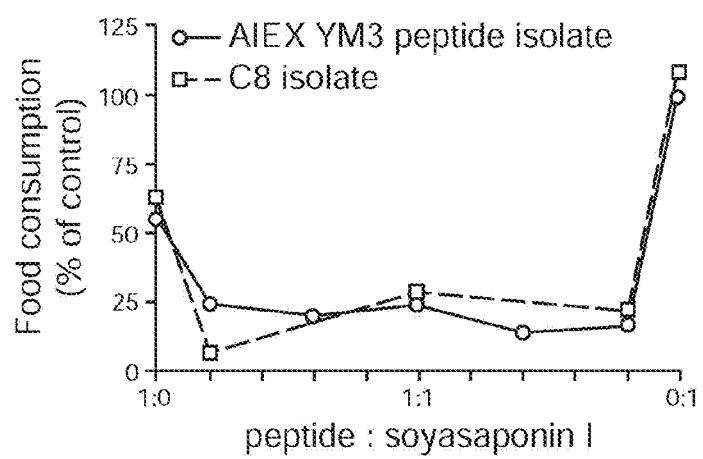
FIG. 26 shows a comparison of antifeedant activity against *S. oryzae* of an anion exchange flowthrough isolate (AIEX YM3) and a crude C8 isolate when mixed with soyasaponin I in various proportions. The total dose was 1.6 mg/200 mg flour.
Figure 28:
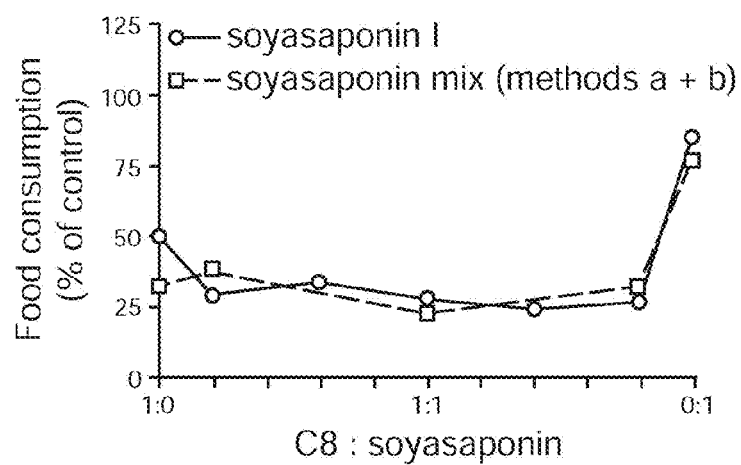
FIG. 28 shows a comparison of antifeedant activity against *S. oryzae* of a crude C8 isolate when mixed in various proportions with soyasaponin I and a soyasaponin mixture partially purified by Diaion HP 20 and neutralized with Dowex SOW (methods a+b). The total dose was 1.6 mg/200 mg flour.

Following teachings of Bodnaryk et al. (U.S. Pat. No. 5,955,082) and isolating extracts with C8 silica Sep Pak Vac™ technology produces a composition that is highly enriched in peptides than saponins with a typical PA1b-related peptide to saponin ratio of 30:1. The inventors have discovered an insecticidal peptide to saponin ratio range that provides for more effective insecticidal activity. The present invention provides for compositions that have a more effective insecticidal peptide to saponin ratio ranging from about 10:1 to about 1:10. As a non-limiting example, FIGS. 25, 26 and 28 show insecticidal efficacy of PA1b-related peptide to saponin ratios ranging from 9:1 to 1:9. Other examples of an effective PA1b-related peptide to saponin ratio include, without limitation, 8:1, 7:1, 6:1, 5:1, 4:1, 3:1, 2:1, 1:1, 1:2, 1:3, 1:4, 1:5, 1:6, 1:7, 1:8 or any ratio therebetween.

The inventors have surprisingly found that absence of chloroform treatment provides for an alcohol extracted insecticidal composition that has an insecticidal peptide to saponin ratio that is closer to unity (that is, 1:1). For example, pea flour treated with chloroform and methanol typically results in an extract having a 10:1 peptide to saponin ratio, whereas in absence of chloroform treatment, methanol extraction of non-defatted or lipid-containing pea flour results in ratios that typically range from 2:1 to 5:1.

Figure 8:
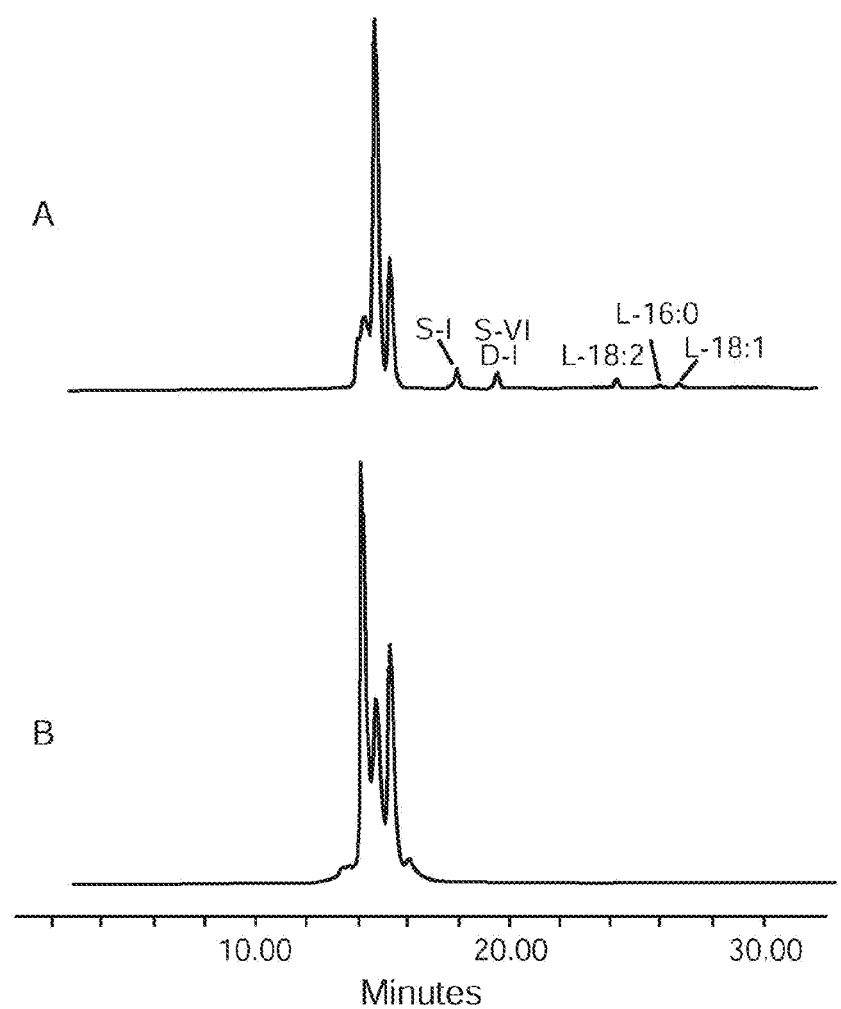
FIG. 8 shows a comparison by HPLC with a reversed phase C-18 Symmetry™ column and an evaporative light scattering detector illustrating major components eluting from 14-16 minutes in (A) a crude mixture of C8 and (B) a system 1 isolate (fraction 4) from silica flash chromatography on C8 with chloroform-methanol-water. See FIG. 5 for identification of the labeled peaks. HPLC conditions were the same as in FIG. 3.

Insecticidal peptide to saponin ratios may be determined by any number of conventional methods for determining peptide and saponin levels. As an example, PA1b-related peptide to saponin ratios may be determined by HPLC with an internal standard (for example, alpha-hederin), as described in Example 31. In another example of the present invention shown in FIG. 8, HPLC analysis reveals PA1B-related peptides having a molecular weight of about 4000 Daltons typically eluting in a range from about 13 to about 19 minutes, while a significant proportion of other peptides elute before 5 minutes, and an internal standard of alpha-hederin eluting at about 20 to 22 minutes.

Any plant may be used as starting material for treatment with alcohol to extract naturally-occurring insecticidal compounds in the context of the present invention. Any plant that contains an insecticidal peptide, a saponin, or both an insecticidal peptide and a saponin is relevant to the present invention. Thus, the use of plant material that comprises at least one insecticidal peptide or at least one saponin is contemplated. Legumes are examples of plants that may be used as starting material. Other non-limiting examples are plants that are selected from the group consisting of: species from the genus *Pisum*, species from the genus *Cajanus*, species from the genus *Lablab*, species from the genus *Lens*, species from the genus *Macrotyloma*, species from the genus *Phaseolus*, species from the genus *Psophocarpus*, species from the genus *Vignia*, species from the genus *Medicago*, and species from the genus *Cicer*. Still other non-limiting examples are plants that are selected from the group consisting of: *Pisum sativum, Cajanus cajan, Lablab purpureus, Lens culinaris, Macrotyloma uniflorum, Phaseolus vulgaris, Psophocarpus tetragonolobus, Vignia anonitafolia, Vigniafaba, Vignia mungo, Vignia unguiculata, Medicago sativa,* and *Cicer arietinum*. Other examples of suitable plant material can easily be determined empirically using standard techniques.

The present invention provides peptide-containing plant extracts having insecticidal activity. Characterization of the peptide-containing extracts has identified multiple related polypeptides of molecular mass 3731, 3736, 3741, 3752, 3757, 3788, 3789, 3805, 3841, 3857 and 3957, all of which were found by mass spectrometry to be related to pea albumin 1b (PA1b; mass of 3788). Accordingly, the present invention provides an insecticidal alcohol soluble plant extract comprising a PA1b-related peptide. By "PA1b-related peptide" is meant any peptide comprising a sequence that is at least 60%, 62%, 64%, 66%, 68%, 70%, 72%, 74%, 76%, 78% or 80% identical to any one of the sequences represented in FIGS. 18-21 and 23 (SEQ ID Nos:1-60), and exhibits insecticidal activity alone or in combination with a saponin.

In an example of the present invention, a PA1B-related peptide comprises an amino acid sequence of Cys-(Xaa)n-(Xaa)n-Cys-(Xaa) n-Pro-(Xaa)n-(Xaa) n-Pro-Cys-(Xaa)n-(Xaa) n-Cys-(Xaa) n-Cys-(Xaa)n-Pro-(Xaa)n-(Xaa)n-(Xaa) n-Cys (SEQ ID NO:63), where each Xaa is independently selected from any amino acid and each n independently equals 1, 2, 3, 4, or 5. In another example of the present invention, a PA1B-related peptide comprises an amino acid sequence of Cys-(Xaa)n-(Xaa) n-Cys-(Xaa)n-Pro-(Xaa)n-(Xaa)n-Pro-Pro-Cys-(Xaa)n-(Xaa)n-Cys-(Xaa)n-Cys-(Xaa) n-Pro-(Xaa)n-(Xaa) n-(Xaa)n-Cys-(Xaa)n-Pro (SEQ ID NO:64), where each Xaa is independently selected from any amino acid and each n independently equals 1, 2, 3, 4, or 5. In again another example of the present invention, a PA1B-related peptide comprises an amino acid sequence of Cys-Xaa-Xaa-(Xaa)n-Cys-Xaa-Pro-Xaa-(Xaa)n-Xaa-Xaa-Cys-Xaa-Xaa-Xaa-(Xaa)n-Cys-Xaa-Cys-Xaa-Pro-Xaa-(Xaa) n-Xaa-Xaa-Xaa-Xaa-(Xaa) n-Cys (SEQ ID NO:65), where each Xaa is independently selected from any amino acid and each n independently equals 0, 1, 2, 3, or 4. In still another example of the present invention, a PA1B-related peptide comprises an amino acid sequence of Cys-Xaa-Xaa-(Xaa)n-Cys-Xaa-Pro-Xaa-(Xaa)n-Xaa-Pro-Pro-Cys-Xaa-Xaa-Xaa-(Xaa)n-Cys-Xaa-Cys Xaa-Xaa-(Xaa)n-Xaa-Xaa-Xaa-Xaa-(Xaa)n-Cys-(Xaa)n-Xaa-Pro (SEQ ID NO:66), where each Xaa is independently selected from any amino acid and each n independently equals 0, 1, 2, 3, or 4. In yet another example of the present invention, a PA1B-related peptide comprises an amino acid sequence of Cys-Xaa-Xaa-(Xaa)n-Cys-Ser-Pro-Phe-(Xaa)n-Xaa-Pro-Pro-Cys-Xaa-Xaa-Xaa-(Xaa)n-Cys-Xaa-Cys-Xaa-Pro-Xaa-(Xaa)n-Leu-Xaa-(Xaa) n-Gly-Xaa-Cys-(Xaa)n-Xaa-Pro (SEQ ID NO:67), where each Xaa is independently selected from any amino acid, and each n independently equals 0, 1, 2, 3, or 4. It will be understood that each n independently indicates multiples of an Xaa residue. For example, where n equals zero an Xaa residue is removed, where n equals one a single residue is represented, where n equals two a double Xaa sequence is represented with each Xaa being independently selected from any amino acid, where n equals three a triple Xaa sequence is represented with each Xaa being independently selected from any amino acid, etc. In a further example, a PA1B-related peptide comprises an amino acid sequence having the general formula X1-C-X2-C-X3-C-X4-C-X5-C-X6-C-X7 as previously defined in WO99/58695 (Delobel et al.).

PA1B-related peptides, for examples see FIG. 23 (SEQ ID Nos:1-8), have been identified from field pea (*Pisum sativum*) extracts (C8 extracts) and were found to be approximately 4000 Daltons (Da) in molecular mass, mixtures of which could be synergized by a saponin, for example, triterpenoid saponins. Two groups of major peptides were identified, those with a methionine at position 12 (molecular masses of 3736, 3741 and 3789 Da) and those with an oxidized methionine (methionine sulfoxide) at position 12 (3752, 3757 and 3805 Da). In addition, a pair of related peptides (with isoleucine rather than methionine at position 12) of 3788 and 3731 Da were identified. These peptides are closely related to pea albumin 1b (PA1b), cysteine-rich methanol soluble peptides first reported by Higgins et al. (1986).

Accordingly, the present invention provides an insecticidal composition comprising an isolated PA1b-related peptide and an isolated saponin, the peptide to saponin ratio ranging from 10:1 to 1:10, wherein the PA1b-related peptide comprises a sequence that is at least 60%, 62%, 64%, 66%, 68%, 70%, 72%, 74%, 76%, 78% or 80% identical to an amino acid sequence selected from the group consisting: SEQ ID NO:1, SEQ ID NO:2, SEQ ID NO:3, SEQ ID NO:4, SEQ ID NO:5, SEQ ID NO:6, SEQ ID NO:8, and SEQ ID NO:9.

The present inventors have surprisingly discovered saponin-containing plant extracts having insecticidal activity. Saponins are naturally-occurring detergent compounds (glycosides) found in a wide variety of plant life. Structurally, saponins are characterized by one or more carbohydrate moieties linked to a polycyclic aglycone or sapogenin moiety which can have a steroid, triterpene, or steroid alkaloid ring system. The carbohydrate moieties are most frequently derived from glucose, but saponins in which the aglycone is linked to other saccharides including without limitation rhamnose, xylose, galactose, and mannose, as well as disaccharides and trisaccharides, are also useful. Saponins are usually found in complex mixtures of closely related compounds, but separation of individual saponin compounds from one another is not required for use in accordance with this invention. Beans are representative examples for a source of saponins. Some herbs known for their saponin content include ginseng, alfalfa, yucca, aloe and quinoa seed. Previous work (U.S. Pat. No. 5,955,082 issued Sep. 21, 1999) showed that a sample of soyasaponin I was nearly inactive in the rice weevil bioassays.

Characterization of the saponin-containing extracts has identified saponins that lack insecticidal activity alone, but demonstrate an insecticidal effect in combination with peptides. Other saponins are identified that exhibit insecticidal activity both alone or in combination with peptides. Furthermore, both saponins that lack insecticidal activity alone and saponins that exhibit insecticidal activity alone, have been shown to act synergistically in combination with peptides with respect to insecticidal activity. For example, Soyasaponin I, isolated from peas and soybeans, and mixtures of soyasaponins, comprised of soyasaponins I-III and isolated from soybeans, were inactive as insecticides but were effective synergists of insecticidal pea peptides. As another example Dehydrosoyasaponin I (C-22 ketone derivative of soyasaponin I), a minor component isolated from pea extracts, was also an effective synergist but showed antifeedant activity by itself. As yet another example, triterpenoid saponins available commercially were found to be insecticidal alone (beta-escin and alpha-hederin) whereas echinocystic acid 3-glucoside, glycyrrhizic acid and hederacoside C demonstrated an additive-like effect on mixing with pea polypeptides.

Accordingly, the present invention provides an insecticidal alcohol soluble plant extract comprising a saponin. The saponin can be any natural or chemically synthesized structural equivalent of a saponin, examples of which are found throughout the plant kingdom. For example, the saponin may be a triterpenoid saponin. Non-limiting examples of triterpenoid saponins are soyasaponins I-III, soyasaponin VI, dehydrosoyasaponin I, echinocystic acid 3-glucoside, glycyrrhizic acid, hederacoside C, beta-escin or alpha-hederin. Any saponin that has insecticidal activity alone or in combination with a PA1b-related peptide can be used in the context of the present invention.

Saponins can be isolated from various plants. For example, dehydrosoyasaponin-I is known to occur as a minor component in peas as well as other common legumes, including alfalfa and soybeans. This saponin has also been isolated from other leguminosae, notably *Desmodium styracifolium, Wistaria brachybotrys, Sophorae Subprostatae, Abrus cantoniensis* and *D. adscendens*. The present disclosure is the first to show the insecticidal activity of dehydrosoyasaponin-I.

Still other examples of saponins are listed in U.S. Pat. No. 5,698,191, issued Dec. 16, 1997 and include horse chestnut saponins such as alpha-escin, beta-escin, and combinations thereof; quillaja saponins such as those extracted from the bark of the tree *Ouillaria saponaria*; root saponins such as those extracted from various species of soapwort roots such as Iranian soapwort root (*Acanthophylum squarrosum* boiss, family caryophyllaceae) and Levantine soapwort root (mixture of *Gypsophila paniculata* L., *G. effusa*, and *G. acutifolia fisch*); saponins extracted from the group of plants consisting of *Agave, Dioscorea, Yucca, Medicago,* and *Cyamopsis*, particularly the Yucca species *Yucca mohavenis, Yucca schidigera,* and *Yucca augustifolia*, as well as the saponin source materials of such sapogenins as smilagenin, hecogenin, and tigogenin.

Complex phospholipids of the lysolecithin type were also identified in C8 extracts. Three of these compounds had no insecticidal activity and they did not enhance the insecticidal activity of pea polypeptides in tests for synergism. However, the activity of saponins may be enhanced in the presence of lysolecithins.

Dosage and application methods of insecticidal compounds of the present invention can be similar to those used for conventional insecticide agents. Furthermore, the compounds of the present invention that are naturally-occurring and isolated from food grade material may advantageously be used in even higher doses than synthetic pesticides such as methyl bromide.

Effective concentrations of the compounds or extracts of the present invention may readily be determined empirically. Non-limiting examples of effective concentrations range from 0.005 to 13% weight/weight based on the grain or flour being treated, or 1 microgram to 340 microgram per square centimeter of leaf or other plant surface. In representative examples of the present invention, compounds or extracts were typically dissolved in 70% ethanol and mixed with flour in doses ranging from 0.01-25.6 milligram/200 milligram flour.

The present invention will be further illustrated in the following examples.

EXAMPLES

Tables referred to in the Examples are presented together on consecutive pages at the end of the Examples.

Example 1

Isolation of Insecticidal C8 Extracts from Field Peas

Protein-rich pea flour, obtained by an air-classification process, was supplied by Parrheim Foods Limited. This flour was extracted in the laboratory as shown in FIG. 1. These processes have been described previously (U.S. Pat. No. 5,955,082, issued Sep. 21, 1999 to Bodnaryk et al.,) whereby C8 extracts were isolated in the last step using C8 SepPak Vac™ cartridges (purchased from Waters Corporation). The extracts thus obtained were concentrated by evaporation of the methanol and redissolving the residue in 95% ethanol for testing. In the present work, utilizing two C8 SepPak Vac™ cartridges per 100 g of flour, the C8 extracts (in methanol) were combined and concentrated to dryness at 43° C. with a centrifugal evaporator (model SC 110A Savant SpeedVac Plus) and weighed. Starting with 100 grams of defatted protein-rich fraction, C8 powder (beige in color) was obtained in 0.7-0.9% yield in ten experiments.

Example 2

Partitioning Behavior of Antifeedant Substances in the C8 Mixture (Powder Form)

A small portion of C9 powder (27 mg) was suspended in water (10 ml). The pH (indicator paper) was 6. One-half (5 ml) was removed, extracted three times with an Ames aliquot mixer and 2 ml of ethyl acetate, centrifuging between extractions. Savant evaporation of the combined ethyl acetate fraction gave trace quantities (<1 mg) of a residue. This residue did not show activity (117% feeding) in the rice weevil antifeedant bioassay (see Example 29) with 50% ethanol as solvent. The aqueous layer remaining was adjusted to pH 7.5 with 10% sodium bicarbonate solution and extracted as before with ethyl acetate. The residue (<1 mg) was inactive (98% feeding). Further adjustment of the pH to 9.5 with 10% sodium carbonate solution and extraction with ethyl acetate also gave an inactive residue (106% feeding). Finally, the pH of the remaining aqueous layer was adjusted to 7 with 10% hydrochloric acid. Extraction with ethyl acetate gave 2 mg of a solid that was moderately active (50% feeding). The aqueous layer that remained was extracted with n-butanol (1×5 ml). Savant evaporation (65° C.) of the n-butanol gave 10 mg of active material (5% feeding). The remaining aqueous layer on Savant evaporation (65° C.) gave 22 mg of a solid (contaminated with inorganic salts from pH adjustments) that displayed activity (19% feeding).

In a separate experiment, a portion of the C8 mixture (approximately 13.5 mg) in water (5 ml) was extracted directly with n-butanol (1×5 ml) without any pH adjustment. Centrifugation (1500 g) and Savant evaporation (65° C.) of the n-butanol gave 14 mg of active material (11% feeding). The remaining aqueous layer on Savant evaporation (65° C.) gave 2 mg of a solid that displayed activity (34% feeding). Dual extractions of aqueous suspensions of C8 material with n-butanol gave a nearly quantitative transfer of mass from the aqueous to the n-butanol layer. The antifeedant activity was concentrated in the first and second extracts. Residues obtained by Savant evaporation of the third n-butanol extract and of the aqueous layer that remained showed some antifeedant activity (55-60% feeding).

Example 3

Fractionation of C8 Powder by Silica Gel Column Chromatography

A glass column (1.2 cm internal diameter×20.5 cm length) equipped with a solvent reservoir and stopcock was filled with silica gel (Mallinckrodt SilicAR cc-7) using a slurry of the silica gel in chloroform (Merck OmniSolv containing 1% ethanol). The top of the bed was protected with sea sand. C8 powder (130 mg) was applied to the column, after mixing with silica gel, as a 1.25 cm band. Using a slight positive air pressure to maintain reasonable flow rates, the column was eluted with chloroform (75 ml) then with 75 ml volumes of various mixtures of chloroform and methanol followed by pure methanol (Table 1). The column was eluted with more methanol (75 ml) and finally with two additional volumes of methanol (250 ml each). Each of the 12 fractions was rotary evaporated on a Buchi Rotavapor R-114 apparatus with the aid of a Buchi B-169 vacuum system and a water bath (maintained at ≦45° C.). The residue that remained in each flask was transferred to preweighed test tubes (Kimax, 8 ml) by washing successively with 95% ethanol (1 ml), water (0.5 ml) and 95% ethanol (2 ml). A final evaporation was performed with a Savant apparatus (43° C.). The tubes were re-weighed, capped and transferred to the bioassay laboratory. Each sample was dissolved in 70% ethanol (0.5 ml) and 0.2 ml of that solution was added to the wheat flour (200 mg) for preparation of the disks. Dose-response experiments (FIG. 2) were conducted on active extracts, by taking 200, 100, 50, 25, 12.5 and 6.25 microliter aliquots of the original bioassay solution and adjusting the final volume for bioassays to 0.2 ml with 70% ethanol. Control disks were prepared with 0.2 ml of 70% ethanol.

Antifeedant activity was absent in fractions obtained from elution of a silica gel column without the C8 sample (blank in Table 1). This meant that residues from the solvents or the silica gel adsorbent did not contribute to antifeedant effects.

Elution of the column with 100% chloroform removed various, nonpolar compounds from the C8 extract. These nonpolar mixtures accounted for about 14% of the mass of applied C8 extract. Small fractions obtained from elution with 90-95% chloroform (5-10% methanol) showed weak to moderate antifeedant activity. The 80% and 60% chloroform fractions that followed were inactive, exhibiting slight feeding enhancement effects (food consumption >100% of control).

The C8 powder gave 2 chromatographically distinct, high polarity bands that showed good antifeedant activity, the first (12 mg, 15.1% food consumption) appearing in the 40% chloroform (60% methanol) fraction, designated C8-1a.

Figure 2:
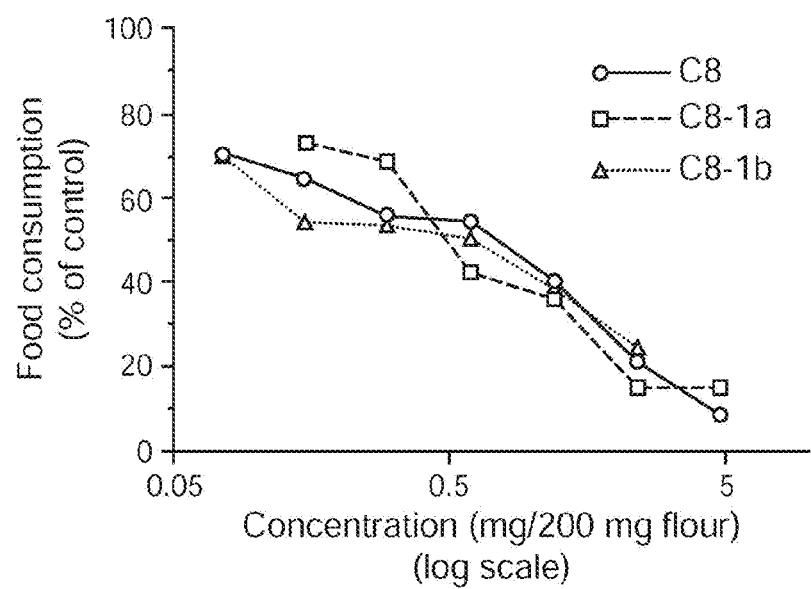
FIG. 2 shows a comparison of dose-response curves in antifeedant bioassays with rice weevils (*S. oryzae*) using a crude C8 extract and partially purified extracts from silica gel column chromatography with 60% methanol-40% chloroform (C8-1a) and 100% methanol (C8-1b).

The second active, very highly polar band eluted gradually with 85-100% methanol and was collected as 5 separate fractions at the end of the experiment. These end fractions, collectively representing about 25% of the mass of applied C8, gave food consumption values of 24.4-45.3% (uncorrected). The most active of these 5 fractions, designated as C8-1b, was compared in a dose-response experiment to C8-1a and to impure C8 (FIG. 2).

Samples of C8, C8-1a and C8-1b were spotted on analytical thin layer chromatography (TLC) plates (EM Science plastic sheets, 0.2 mm layer thickness) and developed with solvent mixtures of system 1 (the lower layer of chloroform-methanol-water: 65-35-10, by volume) and, in separate experiments, with system 2 (n-butanol-ethanol-ammonium hydroxide: 7-2-5). By employing ultraviolet light plus various TLC detection reagents (applied as sprays to the developed plates and exemplified by ninhydrin and Liebermann-Burchard reagents), it could be demonstrated that C8, C8-1a and C8-1b were mixtures of many natural products, the C8 sample of course being the most complex. However, certain of the TLC spots in the sample of C8-1a gave a grey colored response to Liebermann-Burchard, indicative of the presence of triterpene saponins such as soyasaponin I (Hostettmann and Marston, 1995) whereas most of the spots from C8-1b were positive to ninhydrin, indicating that this fraction probably contained nitrogen-containing compounds such as amino acids or peptides (Stahl, 1969). This seemed to imply that at least two chemically distinct insecticidal components were present in the C8 extract of field peas.

Example 4

Fractionation of C8 by Silica Flash Chromatography Using Solvent System 1

A faster method than column chromatography with silica gel was sought to fractionate the C8 mixture into the equivalent of C8-1a and C8-1b, ensuring that there was a clear separation between these insecticidally active fractions. This objective was achieved by flash chromatography (Still et al., 1978) using a FLASH 40 M™ chromatography apparatus (purchased from Biotage Inc., a Division of Dyax Corp., Charlottesville, Va.) equipped with a 1 liter stainless steel solvent reservoir (pressurized with argon gas), a sample injection module (SIM) and a prepacked 90 gram (4×15 cm) KP-Sil™ (Biotage) cartridge (32-63 micrometer, 60 Angstrom silica). A sample of C8 (250 mg) was prepared for chromatography by mixing with Biotage silica (5 g), adding 50 ml of solvent system 1 (the lower layer of chloroform-methanol-Water: 65-35-10) and removing the solvent by rotary evaporation. The dry mixture that remained was transferred to the SIM and packed with a Teflon plunger. The top frit was added to the SIM. The solvent reservoir was filled with system 1 and pressurized. Solvent flow rate was maintained at approximately 20 ml/min. Initially, fractions were collected in 8 ml test tubes and examined by TLC on silica gel with solvent systems 1, visualizing the chromatograms by UV light then by spraying with ninhydrin followed by the Liebermann-Burchard reagent. Fractions were combined on the basis of high, intermediate and low $R_F$ values, corresponding to compounds eluting during flash chromatography with 0-365 ml (combined fraction 1; low polarity), 366-730 ml (combined fraction 2; intermediate polarity) and 731-1000 ml (combined fraction 3; high polarity). Continued elution with 250 ml of methanol gave fraction 4 of very high polarity. All fractions were rotary evaporated and the residue transferred to preweighed test tubes using 70-95% ethanol before Savant evaporation. The properties of these fractions are shown (Table 2).

Compared to column chromatography, flash chromatography with silica cartridges was very effective at separating nonpolar material (fraction 1) in C8 samples. No antifeedant activity could be demonstrated in this major fraction. Fraction 2, designated C8-2a and representing about 20% of the mass of applied C8, was similar in activity and TLC profile (Liebermann-Burchard positive spots) to C8-1a from the silica gel column. Combined fractions 3 and 4, designated as C8-2b, represented a low yield of high polarity, ninhydrin-positive components that were similar to C8-1b from the column.

Example 5

Figure 3:
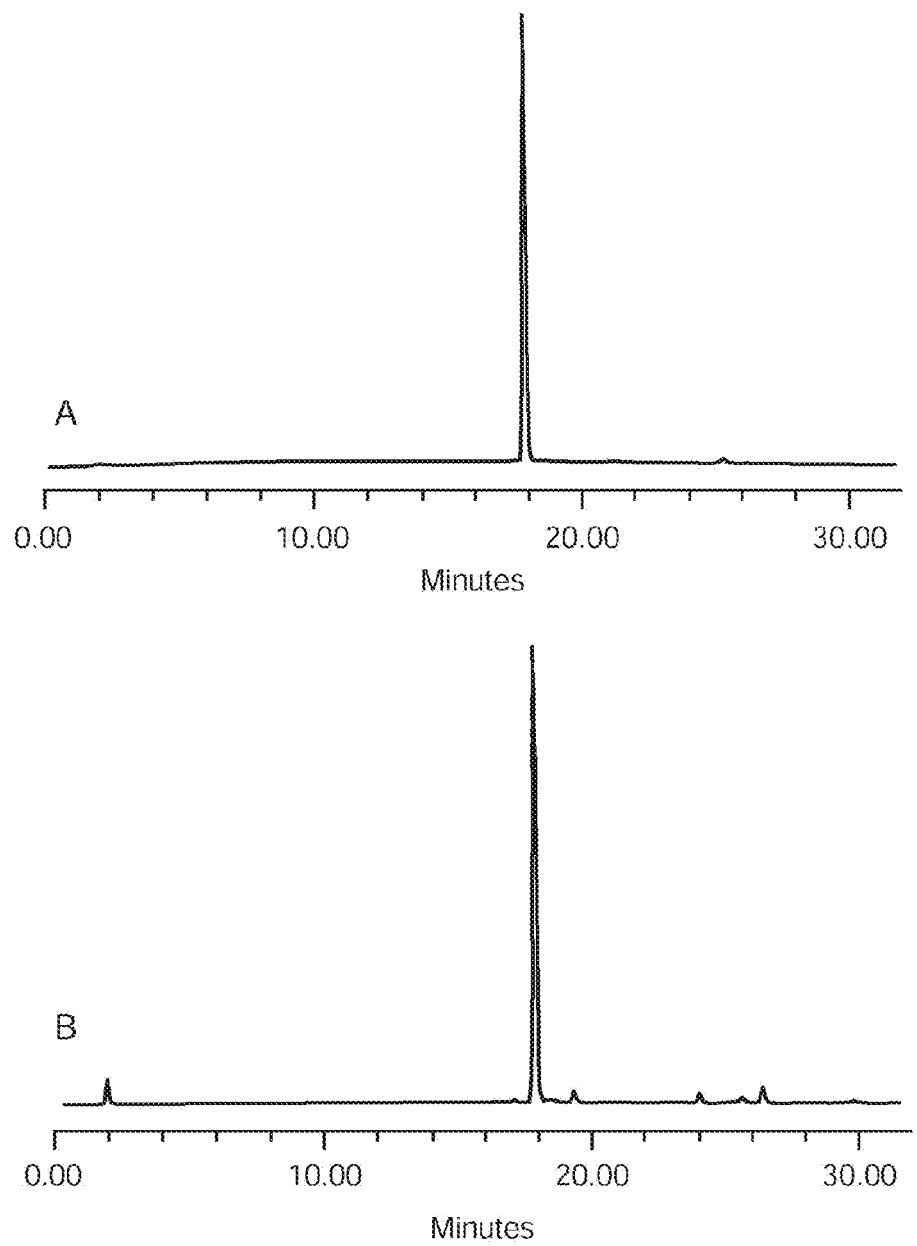
FIG. 3 shows a comparison by HPLC with a reversed phase C-18 Symmetry™ column and an evaporative light scattering detector of (A) a reference sample from Japan of inactive soyasaponin I (S-I) with a retention time of 17.9 minutes and (B) an active S-I enriched extract (C8-2a) isolated from C8 material by silica flash chromatography.

Isolation of Samples of Soyasaponin I and Confirmation of Low Antifeedant Activity Evidence from TLC and HPLC suggested that extracts of C8-2a contained the triterpenoid saponin soyasaponin I as a major component. Authentic samples of soyasaponin I showed the same TLC properties as the proposed soyasaponin I component of C8-2a, using various solvent systems and spray reagents. HPLC clearly illustrated the similarity of these two samples, as illustrated by the ELSD traces shown in FIG. 3. Although several late eluting minor components were found in C8-2a, it was reasonable to suspect that soyasaponin I might be responsible for the antifeedant properties of the C8-2a extract. However, Bodnaryk et al. (U.S. Pat. No. 5,955, 082 issued Sep. 21, 1999) showed previously that a sample of soyasaponin I (received as a gift from a Japanese scientist) was nearly inactive in the rice weevil bioassays. In the present work, samples of soyasaponin I of various purities were isolated from soybean meal (using procedures from Kitigawa et al., 1974 and 1976) and the antifeedant activity compared (Table 3). The results demonstrated that none of the preparations of soyasaponin I approached the activity of C8-2a.

Isolation of soyasaponins from soybeans by the procedures of Kitagawa et al. was carried out in a pilot plant (POS pilot plant, Saskatoon) which involved treatment with 5% sodium hydroxide near the end of the extraction process. This meant that compounds with a carboxylic acid functional group were isolated as the sodium salt. With soyasaponin I, which contains glucuronic acid (glcUA) at position 3 (C-3 glcUA-galactose-rhamnose), this compound was isolated as the sodium salt, composed of a mixture of sodium salts of soyasaponin II (C-3 glcUA-ara-rha), soyasaponin III (C-3 glcUA-gal) and other impurities. By starting with 10 kg of defatted soybean flour (Sigma S9633, type I), a total of 24 grams of a crude mixture containing the sodium salts of soyasaponins I-III was obtained.

Figure 4:
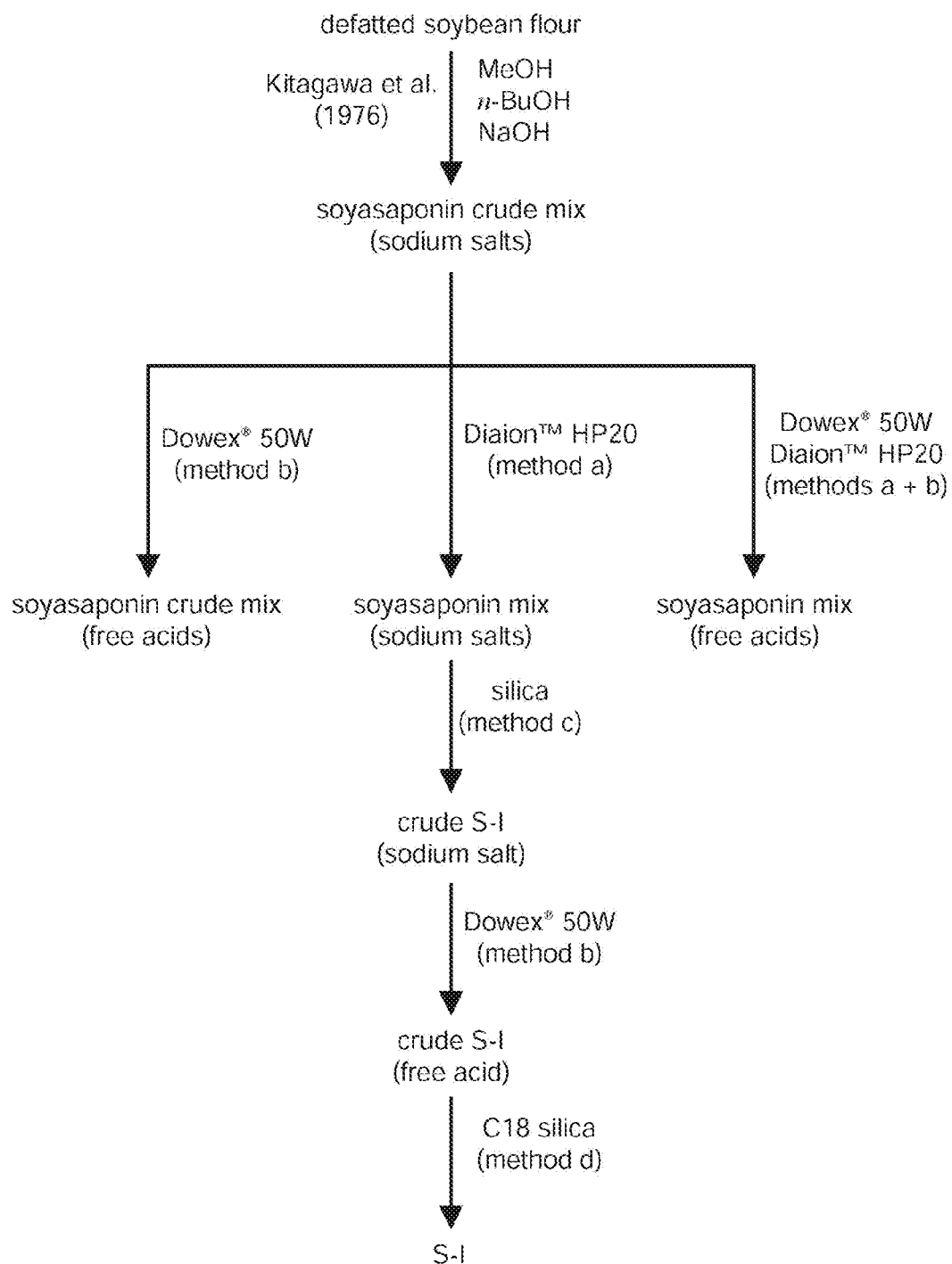
FIG. 4 shows an isolation of soyasaponin mixtures from soybean flour and a purification of soyasaponin I (S-I).

Small portions of this crude mixture were purified by the following methods, depicted in FIG. 4:

(a). With the nonionic macroreticular resin Diaion™ HP20 (250-600 micrometer, 300-600 A). Using a FLASH 40 M™ chromatography apparatus, the crude mixture (0.5 g) dissolved in water (5 ml) was syringe injected onto a 180 ml cartridge of Diaion™ HP20 (a highly porous styrene/divinylbenzene polymeric adsorbent purchased from Biotage) that had been previously washed with water. The cartridge was eluted with water (200 ml), with water containing 50% methanol (200 ml) and finally with methanol (400 ml), using a flow rate of 30 ml/min. The methanol fraction was concentrated by rotary evaporation, transferred to preweighed test tubes with the use of 80% methanol and Savant evaporated (43° C.) to dryness. The contents in the tubes were dried in a vacuum desiccator (containing a package of silica gel beads) to give 246 mg of the soyasaponin mix (sodium salts), as an off white solid Similar yields were obtained when this cleanup was repeated with 2 g of the crude mixture, either by freeze drying the concentrated methanol extract (989 mg of product) or, as described, by rotary and Savant evaporation (1017 mg).

(b). With strongly acidic cation exchange resin (Dowex® 50WX8-400). This resin (10 g, H form), purchased from Sigma, was mixed with deionized water (25 ml) and slurry packed in a 1.5×12 cm polypropylene column (Econo-Pac, from Bio-Rad) equipped with upper and lower porous polymer bed supports. The column was rinsed successively with 1 M hydrochloric acid (30 ml), water (120 ml) and methanol (90 ml). The soyasaponin mix (sodium salts) (136 mg) dissolved in methanol (100 ml) was passed through the column at 5 ml/min. The methanol was collected and evaporated (rotary then Savant). A soyasaponin mix (free acids) was obtained, as an off white, hygroscopic solid (155.6 mg, after drying in a vacuum desiccator) that was highly soluble in methanol and aqueous methanol or ethanol mixtures. Repeating this experiment with 101 mg of soyasaponin sodium salt mixture gave 104 mg of the soyasaponin free acid mixture. The crude soyasaponin mix (sodium salts) (106 mg) without Diaion™ HP20 cleanup gave 101 mg of a brown soyasaponin crude mix (free acids).

(c). With silica gel. A sample of the soyasaponin mix (sodium salts) (1.85 g) cleaned up with Diaion™ HP20 [procedure (a)] was subjected to silica gel flash chromatography as described in Example 4. Fractions eluting with the first 600 ml of solvent 1 gave 774 mg of a brown solid that was rejected on the basis of low soyasaponin I content found by TLC and HPLC. The 200 ml fraction that followed was enriched in soyasaponin I which on solvent evaporation gave 444 mg of a white solid, composed principally of the sodium salt of soyasaponin I. The last fraction (800-1200 ml) on evaporation gave an additional quantity (327 mg) of soyasaponin I, but of lower purity.

(d). With reverse phase silica gel. A cartridge of C-18 silica gel (55 g of Biotage KP-C18-HS, 35-70 micrometer, 60 A) in a FLASH 40 M™ chromatography apparatus was conditioned with a mixture of 95% water and 5% methanol (300 ml total) followed by 50% methanol (250 ml) and 90% methanol (250 ml). The solvent reservoir was filled and the cartridge was equilibrated with 250 ml of 70% methanol. A portion (180 mg) of the main sample from method (c) was neutralized with Dowex 50WX8-400 (method b) and the resulting free acid mixture (165 mg) in 70% methanol (1.65 ml) was injected. After eluting at 15 ml/min with 70% methanol (250 ml), the solvent was switched to 90% methanol (400 ml) and the center fractions obtained with the latter solvent contained mostly soyasaponin I. Savant evaporation at 43° C. gave 95 mg of a white solid, identified as the free acid of soyasaponin I by mass spectrometry (molecular weight of 942) and by recording the FT-IR and carbon-13 FT-NMR spectra (see Example 29) and comparing the spectra to those described in the literature (Kitagawa et al., 1976; Tsurumi et al., 1992).

Example 6

Sovasaponin VI

Because soyasaponin I alone could not explain the antifeedant activity of extracts of C8-2a, other possibilities were considered. Tsurumi et al. (1992) previously reported that pea seedlings contained soyasaponin I in the form of a 2,3-dihyro-2,5-dihydroxy-6-methyl-4H-pyrone (DDMP) conjugate at the C-22 hydroxyl group (soyasaponin VI, also termed chromosaponin I, soyasaponin BeA and soyasaponin βg). They suggested that soyasaponin I does not occur in the free form in peas but is formed from soyasaponin VI during extraction. This type of conjugation has also been demonstrated in dehulled, mature pea seeds and in other legume seeds, including alfalfa, soybeans, scarlet runner beans and adzuki beans. The hydrolytic reaction at C-22, generating 3-hydroxy-2-methyl-4-pyrone (maltol) and soyasaponin I, is reputed to occur gradually in solution, is promoted by heat and is catalyzed by mild alkaline conditions. It was therefore of interest to determine if soyasaponin VI was present in C8 extracts and whether this compound (or maltol) possessed antifeedant activity.

Isolation of soyasaponin VI was carried with a commercial source of air-classified protein-rich pea flour, using a batch of flour that was also used for preparation of C8 extracts. The defatted flour (50 g) was homogenized for 1 min in a Waring blender with ice-cold 80% methanol (500 ml) and centrifuged at 8000 g for 10 min, according to Tsurumi et al. (1992). The supernatant was concentrated on a rotary evaporator (bath temp <30° C.) and the concentrated extract (80 ml) was subjected in 20 ml portions to Diaion™ HP20 flash chromatography according to procedure (a) of Example 5. The resulting methanol extracts were concentrated by rotary evaporation, diluted with water and freeze dried. Combining the freeze dried material gave 284 mg of a light brown solid, which was shown to consist of a complex mixture by TLC with solvent systems 1 and 2 (system 1: the lower layer of chloroform-methanol-water: 65-35-10, by volume; system 2: n-butanol-thanol-ammonium hydroxide: 7-2-5). However, some of the components appeared to be common with those of C8, including at least two soyasaponins (Liebermann-Burchard positive spots) and several spots that were ninhydrin positive. This mixture (130 mg) was subjected to flash chromatography with solvent system 1 with a flow rate of 7 ml/min(as described in Example 4) using a Biotage FLASH 12i apparatus with a prepacked 8 gram (1.2×15 cm) KP-Sil™ (Biotage 12M) cartridge (32-63 micrometer, 60 A silica). The sample was mixed with silica (1.3 g) plus methanol (50 ml), rotary evaporated and transferred to the SIM. Properties of the 6 fractions that were collected are shown in Table 4.

The antifeedant activity of early fractions 1-3 was absent but tended to increase in fractions 4 through 6. Fraction 5 was of particular interest because the sample contained soyasaponins I and VI predominantly and, unlike fraction 6, ninhydrin positive TLC spots that could easily contribute to activity were undetectable. Since soyasaponin I alone was already shown to be inactive, it seemed that soyasaponin VI might be contributing to the activity. However, the potential influence of minor or co-chromatographing components in this fraction needed to be evaluated. Furthermore, synergism between soyasaponin I and VI or between either of these soyasaponins and other components could not be ruled out.

Soyasaponin VI, a complex molecule of molecular mass 1068, was somewhat unstable in solution. During TLC and HPLC analyses, the content of soyasaponin I was found to gradually increase in enriched samples of soyasaponin VI dissolved in aqueous alcohol solutions. Samples containing soyasaponin VI, freshly prepared in 80% ethanol, could be shown to contain intact soyasaponin VI by HPLC/MS with electrospray ionization, by the appearance of the strong quasimolecular ion at mass1069. However, the samples were always contaminated with soyasaponin I (quasimolecular ion at 943).

Maltol, the other hydrolysis product that was inactive as an antifeedant (Table 4), could easily be detected by TLC with solvent system 1 as a mobile, UV-active spot. Reference samples of maltol were available commercially from the Aldrich Chemical Co.

The HPLC properties of fraction 5 of Table 4 were similar to fraction 2 (C8-2a) of Table 2 except that fresh solutions of fraction 5 showed soyasaponin VI as the major peak at 19.5 min. Importantly, the availability of this reference sample confirmed that soyasaponin VI was present as a minor component in C8-2a, at 19.5 min (see FIG. 3). It therefore seemed unlikely that soyasaponin VI, of weak antifeedant activity, could account for the moderate to high activity of C8-2a, which contained soyasaponin VI as a minor component. A logical explanation might be that another active natural product with similar properties to soyasaponins I and VI coexisted in these extracts.

Soyasaponin VI has recently been reported to stimulate the sugar taste receptor cells of the blowfly, Phormia regina (Ahamed et al., 2000), perhaps implicating this compound as a feeding stimulant for certain insects.

Example 7

Mass Spectral Identification of other Components in C8-2a Extracts

Figure 5:
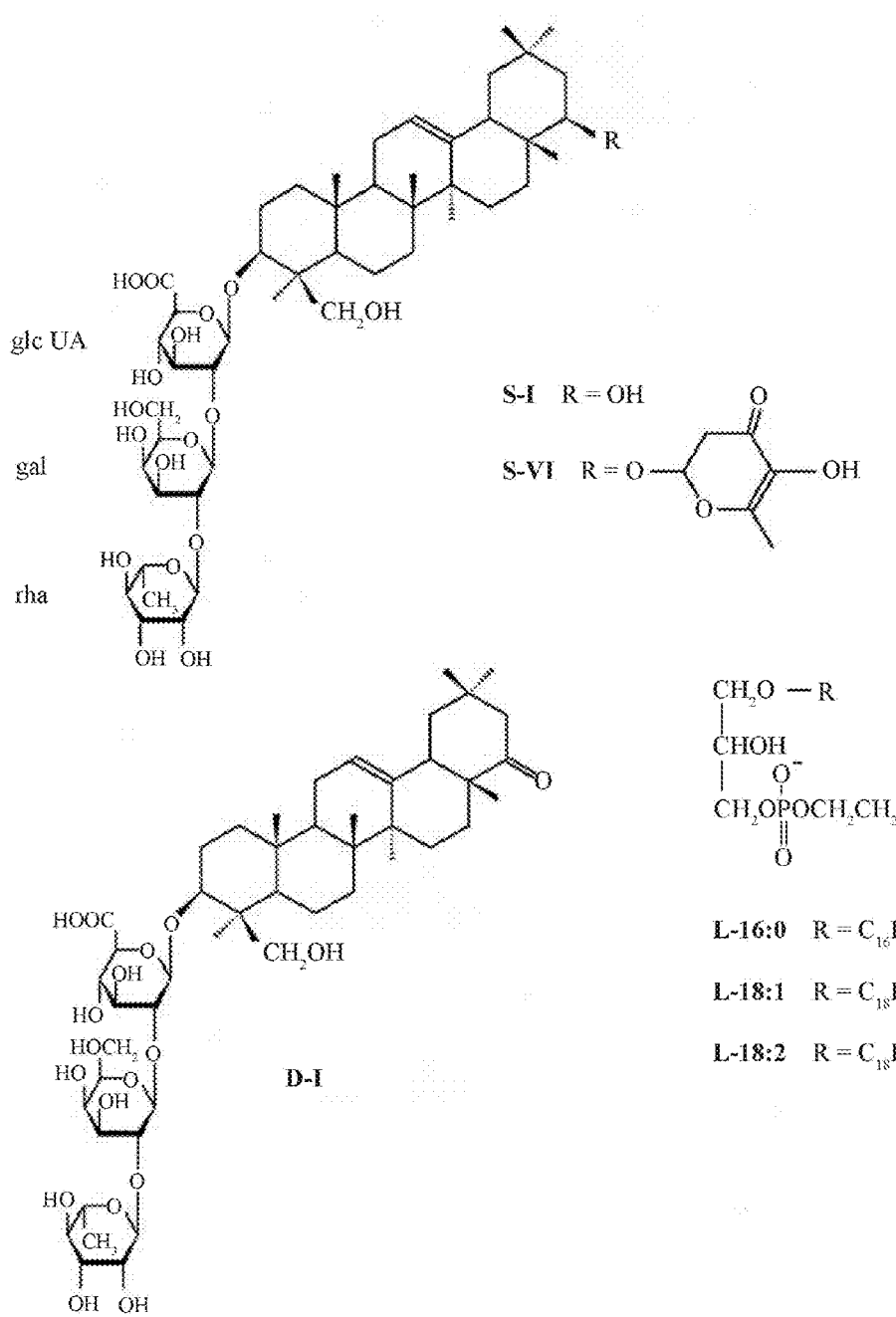
FIG. 5 shows examples of structures of the soyasaponins and lysolecithins identified in C8-2a extracts.

Attempts were made to identify some of the minor components of C8-2a to further characterize its antifeedant activity. This was achieved primarily by HPLC and HPLC/MS (Table 5). The derived chemical structures are shown in FIG. 5.

The major HPLC peak at 17.9 minutes in C8-2a was confirmed as soyasaponin I (S-I in FIG. 5) by HPLC/MS. The peak at 19.5 minutes was of particular interest because not only the quasimolecular ion for soyasaponin VI (S-VI) was observed but also another prominent ion at m/z 941 that corresponded to the molecular weight of dehydrosoyasaponin I (D-1), a natural product that has been isolated previously from other plants. Previous workers have shown that D-1, which occurs as a minor component in soybeans, also coeluted with S-VI under reversed phase HPLC conditions that were quite different than those employed here (Kudou et al., 1992).

The last eluting peaks representing about 5% of the mixture were found by HPLC/MS to represent known phospholipids of the lysolecithin (lyso-phosphatidylcholine) type (Khaselev and Murphy, 2000). Their identity (FIG. 5) was easily confirmed because reference samples containing these compounds were available commercially (Sigma). Reference samples of L-16:0 and L-18:1 were inactive antifeedants, both giving values for food consumption of 102% in the rice weevil bioassay (1.6 mg/200 mg of flour). The reference sample of L-18:2, purchased as a mixture of lysolecithins, showed food consumption of 152% (114% at 1.44 mg/200 mg of flour).

There were very small peaks that eluted close to S-1, two with shorter retention times (17.3 and 17.7 minutes) and two with longer retention times (18.7 and 19.2 minutes). These four unidentified peaks gave observable ions during HPLC/MS at m/z 1029, 1045, 536 (534, 518) and 536 (534, 518) respectively.

Example 8

Additional Fractionation of C8-2a

MCI gel CHP20P, a polymeric adsorbent resin frequently employed in saponin separation chemistry, was washed with methanol and water according to instructions from the supplier (Supelco). The gel was slurry packed into a 1.6×70 cm column (XK model, Amersham Pharmacia Biotech) equipped with dual adaptors. The bed height was 45 cm. The C8-2a extract (46 mg) in 80% methanol (5 ml) was loaded onto the column with a pump (model RP-D, Fluid Metering Inc.). With a flow rate of 3 ml/minute (2 bed volumes/hour), the column was eluted with a step gradient of 100% water to 90% methanol in 10% increments (50 ml fractions). Elution was continued with 100% methanol. Rotary and Savant evaporation of the solvent showed that the first eluting material was contained in the 80% methanol fraction. Appropriate fractions were combined on the basis of similar TLC profiles with solvent system 1 and Liebermann-Burchard (or naphthoresorcinol) spray. Table 6 summarizes the results.

The major component of fractions 1 and 2 was S-I. Both fractions were nearly inactive. Fraction 3, representing the main fraction from the column, contained not only S-I as the major component but also D-I as a minor component. This fraction was the most active. Fraction 4 appeared to be free of both S-I and S-VI but enriched in D-I yet the activity was moderate. The major components in this fraction were the lysolecithins. This evidence seemed to indicate that D-I was contributing to the insecticidal effect of the C8-2a extracts.

D-I is known to occur as a minor component in peas as well as other common legumes, including alfalfa (Kitazgawa et al., 1988) and soybeans (Kudou et al., 1992). This saponin has also been isolated from other leguminosae, notably *Desmodium styracifolium* (Osbeck) Merr. (Kubo et al., 1989), *Wistaria brachybotrys* Sieb. et Zucc (Konoshima et al., 1991), Sophorae Subprostatae Radix (Ding et al., 1992), *Abrus cantoniensis* Hance (Miyao et al., 1996) and *D. adscendens* (Sw.) DC. var. *adscendens* (Papillonaceae) (McManus et al., 1993). In mammalian in vitro experiments (McMannus et al., 1993; McMannus et al., 1995), D-I was shown to be a high-affinity activator of calcium-dependent potassium channels. This compound was 60 fold more potent than S-I as a potassium channel opener. These observation could explain the smooth muscle relaxation effect of extracts of *D. adscendens*, which have been used (particularly in Ghana) as a treatment for asthma. The influence of D-I on insects has not been reported.

Example 9

Isolation of Dehydrosoyasaonin I (D-I)

Although MCI gel provided reasonable separation of S-I and D-I, the latter compound could not be isolated in pure form because of the coeluting phospholipids (lysolecithins). HPLC with C-18 reverse phase columns did not offer a logical solution because D-I and S-VI coeluted under acidic conditions. Using RPC (see Example 29), a good separation of all of these components was achieved with a column of polystyrene/divinylbenzene beads operated at high pH (pH 10.5) and a gradient composed of dilute ammonium hydroxide and acetonitrile.

Figure 6:
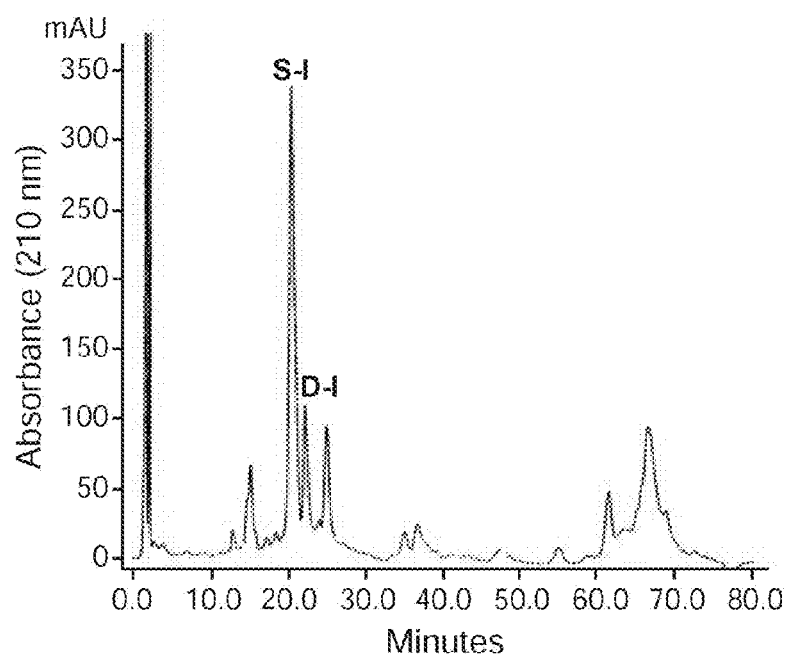
FIG. 6 shows a chromatogram illustrating the separation by medium pressure reverse phase chromatography (Resource 15 RPC column) of soyasaponin I (S-I) and dehydrosoyasaponin I (D-I) contained in S-I enriched fraction 3 from MCI gel liquid chromatography.

A chromatogram (210 nm trace) from RPC separation of D-I and S-I in a MCI gel fraction (fraction 3 of Table 6) is shown (FIG. 6), following a sample injection of 3 mg. After repeating this experiment with additional sample (2.6 mg) and combining the fractions corresponding to D-I (6 ml total volume), a total of 0.64 mg of D-I was obtained as a white solid. The peak that followed D-I, at 25 minutes, corresponded to the retention time of S-VI (from injecting samples known to be enriched in S-VI). Lysolecithins L-16:0, L-18:1 and L-18:2 were strongly retained under these conditions, eluting from 60-70 minutes. With RPC at pH 9 (1 ml Resource 15 column; ammonium bicarbonate buffer), the lysolecithins were less retained, eluting near 40 minutes.

The identity of D-I was readily established by CID experiments (see Example 29) using a tandem mass spectrometer equipped with an electrospray ionization source. These experiments, summarized in Table 7, were-initially done on the protonated form of S-I because the daughter ion fragments of this saponin have been assigned previously (Lee et al., 1999). It was found that D-I fragmented under appropriate CID conditions in an entirely analogous manner, yielding the same daughter ions as S-I but 2 mass units lower, corresponding to the difference in molecular masses of the aglycones. The daughter ion spectra showed that the trisaccharide sequence (see FIG. 5) was the same in both molecules.

Figure 7:
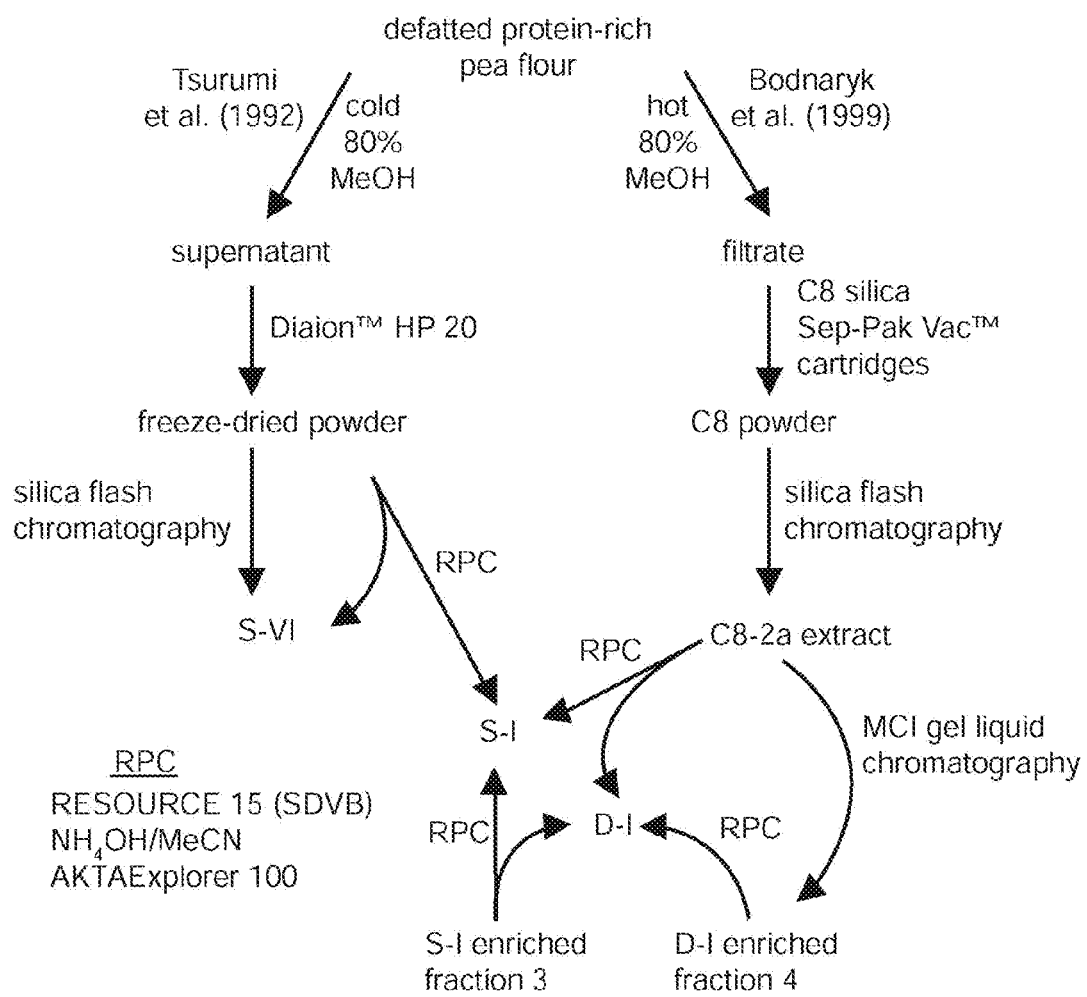
FIG. 7 shows an isolation and purification of S-I, S-VI and D-I from pea flour.

Additional D-I (0.26 mg) was isolated by RPC on MCI gel fraction 4, by injecting 3.2 mg in two equal batches and combining the fractions corresponding to the peak for this saponin. Small amounts of D-I could also be isolated by RPC on saponin-enriched C8-2a extracts but of reduced purity, as evidenced by the appearance of contaminants of similar retention times in 280 nm traces. It was also possible to isolate additional small samples of S-I and S-VI by RPC. FIG. 7 gives a summary of the procedures used in the isolation of the saponins of peas.

Since quantities of RPC isolates were very limited, the antifeedant tests were performed on disks made from one-half the usual amount of flour. This meant that a fewer number of disks were available from which to select for the bioassay but the concentrations were similar to standard conditions (the equivalent of 1.6 mg/200 mg or 0.8 mg/100 mg of flour). Under these conditions, the RPC isolates of S-I, S-VI and D-I gave food consumption values in the rice weevil bioassay of 100% (0.43 mg dose), 80% (0.8 mg) and 65% (0.64 mg) respectively.

Although the activity of D-I was slightly greater than S-VI, it did not seem reasonable that the presence of D-I by itself could account for the antifeedant effect of C8-2a extracts or of fractions of C8-2a obtained by MCI gel chromatography. Another important observation was the S-VI isolated by RPC showed weaker antifeedant activity than the isolate of S-VI obtained by silica flash chromatography (fraction 5 of Table 4). A possible explanation could be that one or more of the saponins present in these samples was interacting synergistically with the ninhydrin-positive antifeedant component that might be contaminating the active saponin samples.

It should be noted, however, that samples of C8-2a, including the MCI gel purified fractions of C8-2a, appeared to be free of high-polarity ninhydrin-positive components, that is the components of $R_F < 0.25$ by TLC with solvent system 1 (see C8-2b of Table 2). In addition, these highly polar substances were not readily detected during HPLC (FIG. 3), but were subsequently shown to elute near 15 minutes.

Example 10

System 1 and System 2 Ninhydrin-Positive Isolates

End fractions from flash chromatography with silica gel (fraction 34 of Table 2) contained at least one other insecticide that was chemically unrelated to the saponins. In addition to the pink spots detected on TLC plates with ninhydrin, other spray reagents (Stahl, 1969; Schlittler and Hohl, 1952; Fried and Sherma, 1994) gave positive reactions including Dragendorff, Ehrlich, chlorine-tolidine, iodoplatinate, potassium permanganate, Schlittler and fluorescamine. These spray reagents collectively suggested that the other insecticide was probably an amino acid, peptide, protein, alkaloid or other nitrogen-containing compound. Fractions 3 and 4 were impure by TLC but one main spot was detected, tailing from the origin with solvent system 1 (chloroform-methanol-water) and with an $R_F$ of 0.5 with system 2 (n-butanol-ethanol-ammonium hydroxide). HPLC comparison of fraction 4 and a crude C8 extract (FIG. 8) illustrated the complexity of the mixture (fraction 3 gave a similar HPLC profile to fraction 4) and suggested that other components, including the major component of C8, were probably retained on the silica gel flash chromatography cartridge, even after eluting with methanol.

To overcome this difficulty, the purification of C8 extracts by silica gel flash chromatography with solvent system 2 was investigated. The main HPLC component of C8 (at 14.9 minutes in FIG. 8) appeared to have an $R_F$ of 0.28, which was much lower than the system 1 isolate and the least mobile ninhydrin-positive spot detected in C8 mixtures. Thus, a C8 extract (150 mg) was subjected to flash chromatography on a Biotage FLASH 12i apparatus with a prepacked 8 gram cartridge (see Example 4) and solvent system 2 (2 m/min), collecting 5 fractions (with 67 ml per fraction). After solvent evaporation, first with a nitrogen line (50° C. bath temperature) and then with a Savant apparatus, fractions were obtained with the properties shown in Table 8.

C8 mixtures could be quickly fractionated by flash chromatography using relatively small quantities of solvent system 2. The first fraction was practically inactive in antifeedant tests, reminiscent of nonpolar fractions from previous experiments. Fraction 2, isolated as a highly complex mixture, was quite active. Active fractions 3-5 were clearly enriched in a major component of the C8 mixture. The main fraction (fraction 3) was compared to the main fraction (fraction 4 of Table 2) from flash chromatography with solvent system 1 by FT-IR spectroscopy, MALDI mass spectrometry and amino acid analyses.

Amino acid analyses were performed by separately transferring solvent system 1 and 2 isolates (1 mg) to test tubes containing 1 ml of 6M hydrochloric acid (Sigma H-0636, constant boiling). The mixture was heated for 16 hours at 110 degree C. with the Pierce Reacti-Therm system, equipping the test tubes with a Teflon-lined screw-cap. The excess hydrochloric acid was evaporated on an N-EVAP apparatus with a gentle stream of nitrogen gas (fumehood).

The residue that remained was dissolved in acidified isopropanol (0.5 ml; prepared at 2.8 M hydrochloric acid by the addition of 250 microliter of acetyl chloride per ml of isopropanol), the tube was capped and the contents were heated at 110 degree C. for a further 45 minutes and then cooled (−15 degree C.). A dry residue was obtained (N-EVAP) which was dissolved in methylene chloride (0.25 ml) and pentafluoropropionic anhydride (1100 microliter, Supelco 3-3167) was added. The test tube was capped and the contents were heated at 110 degree C. for 15 minutes. Excess reagent was removed (N-EVAP) and the samples were transferred with hexane (200 microliter) into autosampler vials for analysis by electron impact (70 eV) GC/MS (Hewlett-Packard model 5989A) with a HP-1701 column (30 m×0.25 mm i.d., 0.25 μm film thickness) and helium as the carrier gas (under electronic pressure control). Samples (1 microliter), including derivatized L-amino acids as references, were injected splitless (45 seconds) at an initial oven temperature of 50 degree C. After 1 minute, the temperature rose at 25° C./minute to 100 degree C. then at 10° C./minute to 250 degree C. The column was held at 250 degree C. for 10 minutes. Background subtracted mass spectra were obtained with a scan range of 35-800 mass units. The temperature of the ion source was 250 degree C. Confirmation of molecular weights of the pentafluoropropionamide isopropyl ester derivatives was obtained by chemical ionization mass spectrometry with isobutane as the reagent gas. To detect tryptophan, acid hydrolyses were also conducted in the presence of 1% phenol (Muramoto and Kamiya, 1990).

Figure 9:
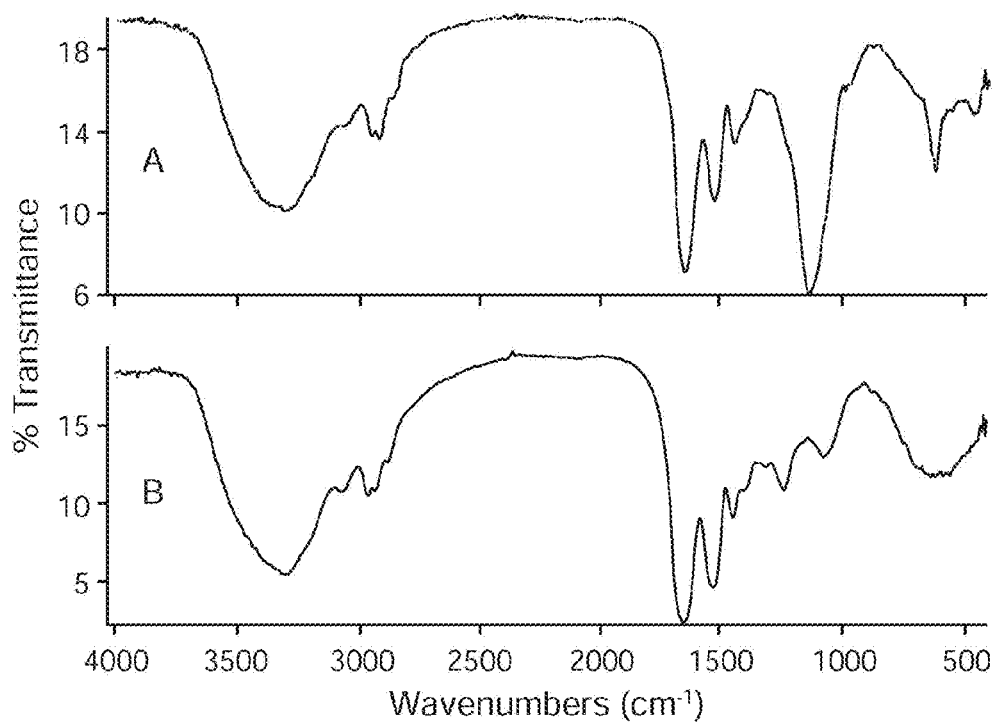
FIG. 9 shows an FT-IR spectra (KBr disks) of (A) system 1 and (B) system 2 isolates from silica flash chromatography.
Figure 10:
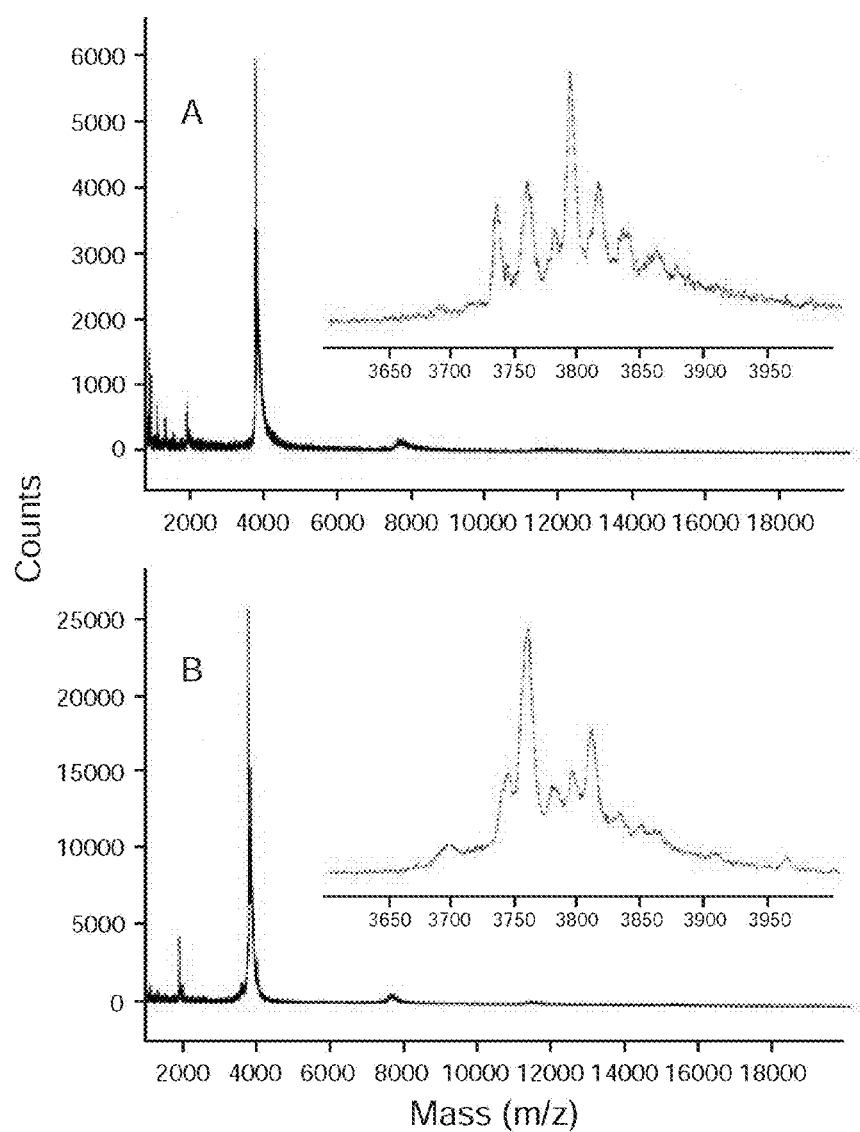
FIG. 10 shows a positive ion low resolution MALDI mass spectra of (A) system 1 and (B) system 2 isolates from silica flash chromatography. The insets show an expansion of the main cluster of ions from each sample.
Figure 11:
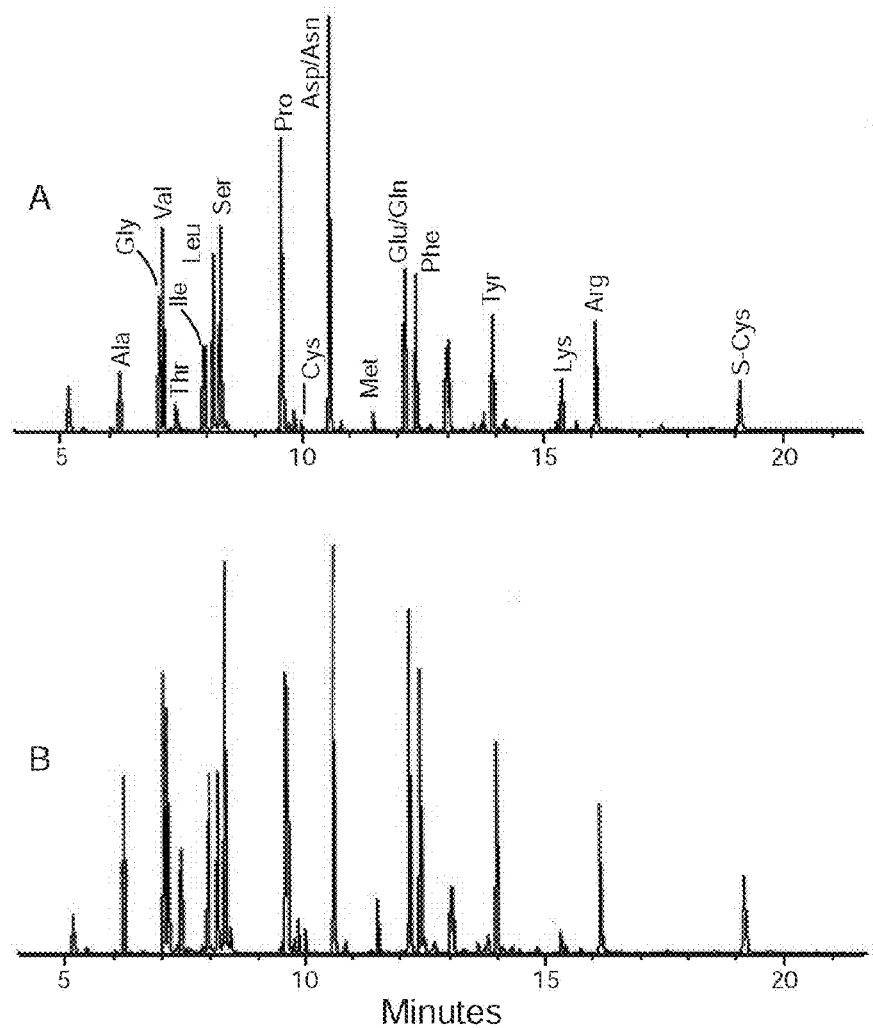
FIG. 11 shows a total ion chromatogram from GC/MS analysis (HP-1701 capillary column, 70 eV) of the pentafluoropropionamide isopropyl ester derivatives of amino acids found in acid-hydrolyzed samples of (A) system 1 and (B) system 2 isolates from silica flash chromatography.

The strong IR absorption band near 1655 $cm^{-1}$ indicated that these two isolates contained amide functional groups (FIG. 9). MALDI mass spectrometry (linear mode, FIG. 10) showed prominent molecular ions near 3800, at approximately 3790 for the system 1 isolate and 3755/3805 for system 2. Following 6M hydrochloric acid hydrolysis, amino acid determinations by GC/MS analysis of pentafluoropropionamide isopropyl ester derivatives (Macko et al., 1997; Gerard et al., 1997) revealed that both isolates contained all of the naturally occurring amino acids, except tryptophan (FIG. 11). Standard samples of histidine were not reliably detected under these conditions and asparagine-aspartic acid or glutamine-glutamic acid cannot be differentiated on acid hydrolysis. Cysteine was detected at trace levels. Detection of cystine (S-cys) suggested that the cysteine residues were probably disulfide-linked.

Example 11

Reduction of C8 with 2-Mercaptoethanol and Ellman Assays

Samples of C8 powder (25 mg) were dissolved in 8 M urea (containing 0.5 M Tris hydrochloride at pH 8.5 plus 5 mM EDTA) and treated with 2-mercaptoethanol (50 microliter) according to the procedure of Imoto and Yamada (1989). After heating the mixture at 40 degree C. for 2 hours, the incubate was transferred to a Sep-Pak Vac (5 g) C8 silica cartridge (Waters) that had been previously conditioned with methanol and water. After washing with water (100 ml) and with a 1:1 mixture of water-methanol (100 ml), the (reduced) peptides were eluted with methanol (200 ml). Evaporation of the solvent gave 18 mg of a solid. This solid was completely inactive in the rice weevil bioassay (food consumption of 102%, relative to control). At the same dose (1.6 mg/200 mg flour), a sample of C8 treated identically but without addition of 2-mercaptoethanol gave a food consumption value of 30%.

In the Ellman assay for thiols, performed in 6 M guanidinium chloride with 0.1 M phosphate buffer at pH 7.3 and 1 mM EDTA according to Creighton (1989), the reduced solid gave a strong absorbance at 412 nm for released nitrothiobenzoate, indicating the presence of free thiol groups. Samples of C8 as well as system 1 and system 2 peptide isolates (Example 10) were negative in the Ellman assay, suggesting that the cysteine thiol groups in the native peptides were disulfide bridged.

Example 12

Reduction and Alkylation Experiments

These experiments were performed initially with samples of C8 (25 mg) exactly as described for 2-mercaptoethanol reduction (Example 11) but with introduction of the alkylation step after the 2 hour incubation. The alkylating agent was iodoacetamide (67 mg), added as a solution in 0.5 M Tris buffer (pH 8.5). After stirring in the dark at room temperature for 15 minutes, the mixture was desalted with a Sep-Pak Vac (5 g) C8 silica cartridge (Waters) as before. Evaporation of the methanol gave 21 mg of a light brown solid that was inactive in the rice weevil bioassay (food consumption of 96.1%). This product was also a useful reference for the mass spectral determination of the number of cysteine groups (see Table 10).

Example 13

Anion Exchange Chromatography on Crude C8 Extracts

Figure 12:
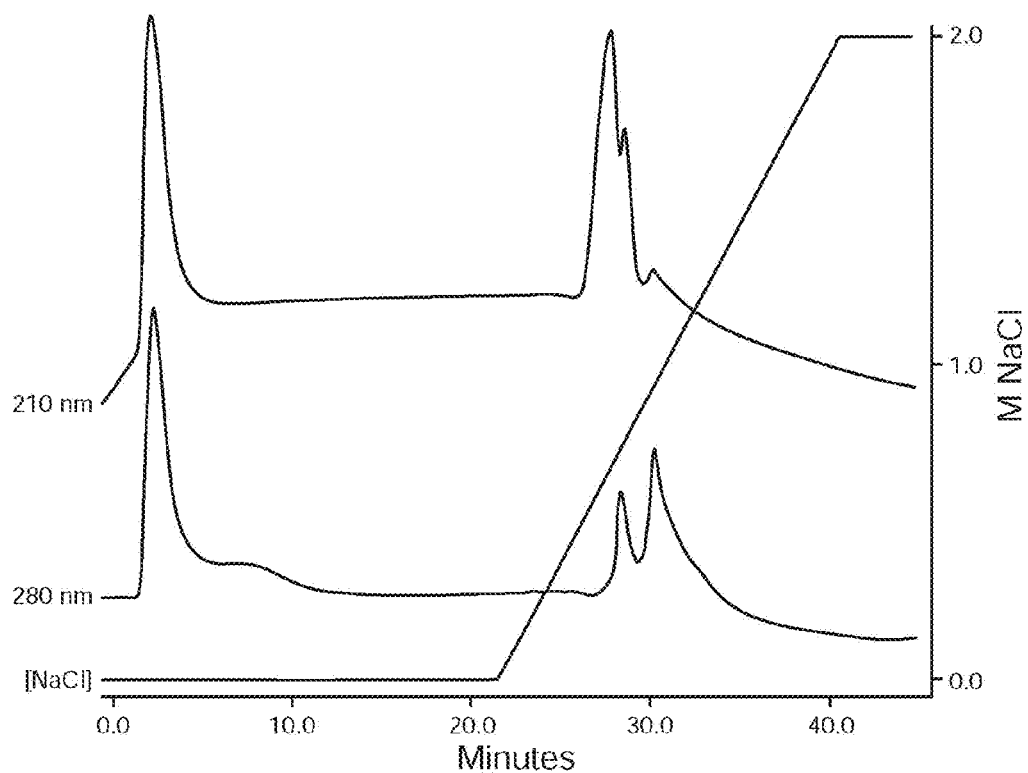
FIG. 12 shows an anion exchange chromatogram (HiTrap Q Sepharose Fast Flow 1 ml column) of crude C8 material illustrating the flowthrough and salt-eluted fractions. The starting buffer was 50 mM ammonium acetate, pH 9.

These experiments were carried out with an AKTAExplorer 100 instrument (see Example 29), initially with a 1 ml (7×25 mm) column prepacked with HiTrap Q Sepharose Fast Flow (Amersham Pharmacia Biotech), a strong anion exchange gel of the quaternary ammonium type. The starting buffer was 50 mM ammonium acetate, adjusted to pH 9 with ammonium hydroxide, and delivered to the column at a flow rate of 1 ml/min. Samples of C8 were prepared in this buffer at a concentration of 4 mg/ml and syringe filtered (0.45 micrometer). After injection of 0.25 ml (1 mg), the column was eluted with 22 ml of buffer before a linear gradient of sodium chloride was applied from 0 to 2 M over 20 minutes. Chromatograms obtained with the UV monitor set at 210 and 280 nm are shown (FIG. 12).

Based on an analysis literature reports on the isolation with Q Sepharose of plant peptides of similar mass (Terras et al., 1992; Cammue et al., 1992), it was predicted that the peptides of interest would elute in the flowthrough fraction (ie., with the first eluting peak of FIG. 12). It was more difficult to predict if this technique would provide a separation of the desired peptides from the other components in the C8 extracts. By collecting the two main fractions, preliminary evidence from TLC and HPLC suggested that the peptides of interest were indeed concentrated in the flowthrough fraction whereas the saponins and lysolecithins eluted during the salt gradient (ie., within the cluster of peaks eluting around 30 minutes). However, the collected samples were very dilute and contaminated with buffer and salt. This was solved by developing methods for chromatographic scale-up and for desalting/concentrating of the peptide-containing fractions.

Scale-up was achieved with a 53 ml (26×100 mm) column prepacked with HiLoad Q Sepharose Fast Flow (Amersham Pharmacia Biotech). In a typical experiment, the C8 sample (700 mg) in 35 ml of 50 mM ammonium acetate (pH 9) was transferred to a Superloop™ (Amersham Pharmacia Biotech) and 32 ml (640 mg) injected onto the column. The column was eluted with 400 ml of 50 mM ammonium acetate at 5 ml/minute followed by a linear gradient of 50 mM ammonium acetate containing sodium chloride (0-2 M NaCl over 106 minutes). The flowthrough and salt-eluted fractions were collected from 0-80 minutes (400 ml volume) and 81-166 minutes (425 ml) respectively.

The flowthrough (unretained) fraction was subjected to ultrafiltration with an Amicon YM3 membrane (3000 molecular weight cutoff) using a pressurized stirred cell (model 8200, Millipore Inc.). The retentate was obtained by washing the membrane with 80% methanol (3×25 ml) and concentrating the solvent on a rotary evaporator. A final concentration was done by transferring the residue (with the use of 6 ml of 80% methanol) to a preweighed test tube followed by Savant evaporation. A white powder (163.5 mg), designated as AIEX YM3, was obtained. Repetition of the entire experiment with a different batch of C8 material and using an Amicon YM1 membrane (rather than YM3) gave an off-white powder (115.6 mg), designated as AIEX YM1.

A 400 ml fraction collected during application of the salt gradient was freeze dried and the resulting powder was stirred in methanol (100 ml) at room temperature. After an hour, the mixture was filtered (scintered glass) and the filtrate was rotary evaporated to give 2.1 g of a white solid, designated AIEX NaCl.

In a separate experiment, a 400 ml fraction collected during application of the salt gradient on freeze drying gave a white powder (15.5 g). A portion (7 g) of this powder was dissolved in water (250 ml) and ultrafiltered (YM3 membrane). The retentate was isolated as described for the flowthrough fraction. A tan solid (80.3 mg), designated as AIEX NaCl YM3, was obtained.

Figure 13:
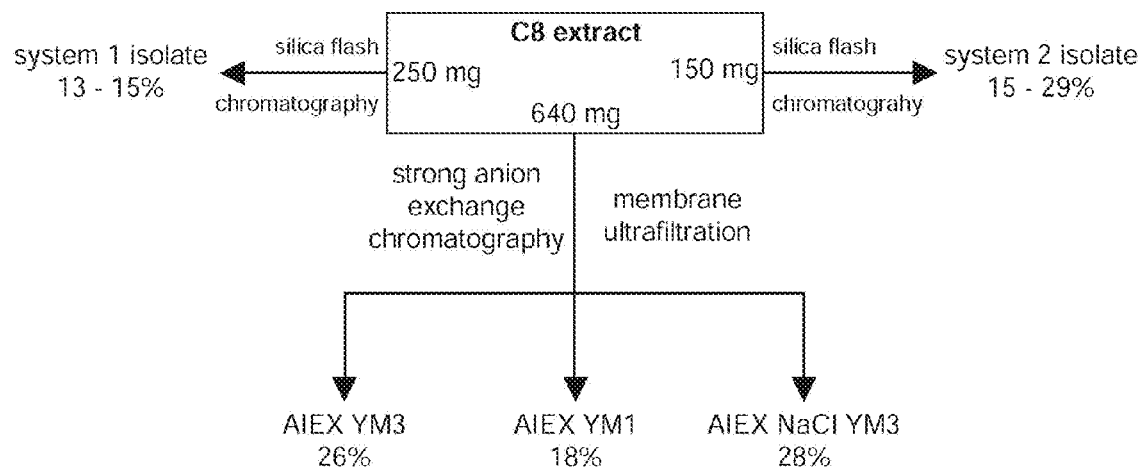
FIG. 13 shows a yield of pea peptide mixtures isolated by silica and anion exchange chromatography.

The yields of peptide mixtures isolated by the various techniques are shown in FIG. 13.

Example 14

Further Small-Scale Studies on the Salt-Retained Material from Anion Exchange Chromatography (a). Treatments with strong base. AIEX NaCl (1 g) was dissolved in 80% methanol (25 ml) containing 25 mM NaOH and stirred at 4 degree C. for 18 hours. The mixture was neutralized with 10% hydrochloric acid and concentrated on a rotary evaporator. The opaque aqueous solution that remained (12 ml) was transferred to a conical centrifuge tube with the aid of water (5 ml). n-Butanol (4 ml) was added with vortex mixing. After centrifuging at 4000 rpm for 10 minutes, the n-butanol layer was transferred to a test tube. The extraction with n-butanol was repeated. Evaporation of the combined n-butanol layers with an N-EVAP at 50° C. gave 33.1 mg of a brown solid, designated as AIEX NaCl NaOH. Additional material (11.9 mg), similar in chromatographic and antifeedant properties to the first isolate, was isolated by re-extracting the remaining aqueous layer with n-butanol (2×4 ml). This experiment was repeated as described but with 250 mM NaOH at 22° C. for 2 hours. A brown powder (22.2 mg) was obtained on extraction with n-butanol (8 ml). Additional extractions with n-butanol (2×5 ml) gave 30.5 mg of an off white powder.

(b). Treatments under controlled conditions of pH. Four samples of AIEX NaCl (100 mg each) were dissolved 15 ml of 10 mM acetic acid (pH 2.8), water (pH 6.8), 50 mM ammonium acetate (pH 9) and 10 mM ammonium hydroxide (pH 10.5) contained in the outer chamber of a centrifugal filter device (Centriprep® YM3, Millipore Corp.). Each Centriprep® YM3 unit had been prerinsed at the appropriate pH. After centrifugation at 1500 g for 1 hour, the filtrate was decanted. After recentrifuging and decanting, the retentate and chamber were rinsed with a solution of appropriate pH (5 ml) and centrifuged. Following two additional rinses with water and centrifugations, the retentate was dissolved in 80% methanol (3×2 ml) with vortex mixing, decanting the solvent after each wash. The combined solutions were Savant evaporated (43° C.) in preweighed test tubes to give the following recoveries: 1.38 mg (pH 2.8), 1.95 mg (pH 6.8), 1.21 mg (pH 9) and 1.42 mg (pH 10.5).

Example 15

Cation Exchange Chromatography

Figure 14:
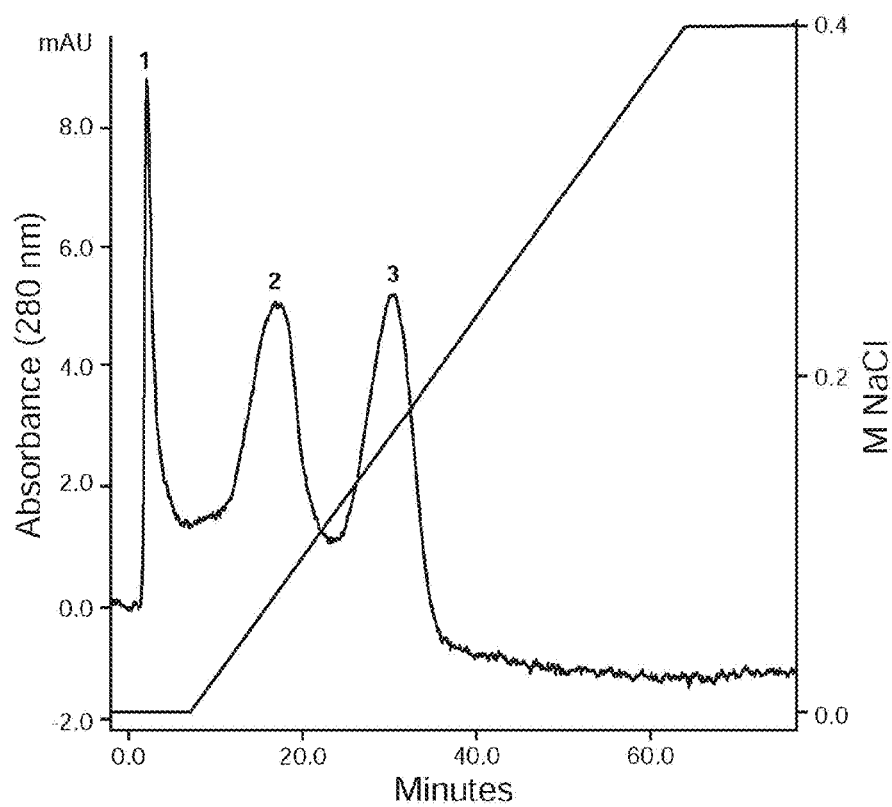
FIG. 14 shows a cation exchange chromatogram (SP Sepharose Fast Flow 1 ml column) of a flowthrough fraction from anion exchange chromatography showing the separation of peptide fractions 1, 2 and 3. The starting buffer was 50 mM sodium acetate, pH 3.

These experiments were carried out with an AKTAExplorer 100 instrument, initially with a 1 ml strong (sulfopropyl) cation exchange column of SP Sepharose Fast Flow (Amersham Pharmacia Biotech). Using 1 mg test samples of AIEX YM3, appropriate separation conditions were demonstrated with 50 mM sodium acetate (pH 3) and a linear salt gradient to 0.4 M. These conditions gave 3 resolved peaks at 280 nm (FIG. 14), the first being relatively unretained whereas the main components eluted during the salt gradient. Resolution of these components was much less apparent at pH 4 and, with ammonium acetate buffer, at pH 6. Experiments with 1 ml columns of HiTrap SP Sepharose Fast Flow and Resource S (Amersham Pharmacia Biotech) gave similar results. Scale-up was achieved with a 20 ml (16×100 mm) column prepacked with HiLoad SP Sepharose Fast Flow. In a typical experiment, an AIEX YM3 fraction (140 mg) in 35 ml of 50 mM sodium acetate (prepared from sodium acetate trihydrate and adjusted to pH 3 with acetic acid) was syringe filtered (0.45 micrometer), transferred to a Superloop™ (Amersham Pharmacia Biotech) and 22 ml (88 mg) injected onto the column. The column was eluted with 200 ml of 50 mM sodium acetate (pH 3) at 5 ml/minute followed by a linear gradient of 50 mM sodium acetate (pH 3) containing sodium chloride (0-0.4 M NaCl over 240 minutes). The peak eluting before the gradient (24-36 min post-injection, CIEX fr. 1), the first peak eluting during the gradient (66-139 min, CIEX fr. 2) and the second peak eluting during the gradient (148-207 min, CIEX fr. 3) were collected and processed as follows.

A portion (15 ml of 60 ml) of the eluent containing CIEX fr. 1 was transferred to a centrifugal filter device (Centriprep® YM3, Millipore Corp.) that had been prerinsed with 50 mM sodium acetate solution (pH 3). After centrifugation at 3000 g, the filtrate was decanted and the retentate and chamber were rinsed with 5 ml of 0.05% acetic acid (pH 3.4). After recentrifugation, the retentate and chamber were rinsed with water (5 ml) and centrifuged. The retentate was dissolved in 80% methanol (3×2 ml) with vortex mixing, decanting the solvent after each wash. The combined solution was Savant evaporated (43° C.) in a preweighed test tube to give 1.65 mg of a white solid. Using the above-described Centriprep procedure, portions (15 ml) of the eluent containing CIEX fr. 2 and CIEX fr. 3 gave 1 mg and 0.7 mg respectively.

The eluent containing CIEX fr. 2 (350 ml of 365 ml) was ultrafiltered with a stirred cell containing a YM3 membrane (according to Example 13). After washing the membrane with 80% methanol and Savant evaporation, 42.3 mg of a white powder of CIEX fr. 2 was obtained. Using the same techniques, CIEX fr. 3 (280 ml of 295 ml) gave 32.5 mg of a white solid (see Tables 9 and 10).

Example 16

Reduction and Alkylation Experiments for Electrospray Mass Spectrometry

Small scale reduction-alkylation experiments were conducted with the same reagents as described (Example 12), using 0.5 mg of peptide in a buffered solution of urea (130 microliter) plus 2-mercaptoethanol (10 microliter) and iodoacetamide (6.7 mg). Sample cleanup and concentration were performed using pipette tips containing C18 silica (Zip-Tip C18, Millipore Corp.), using procedures described by the manufacturer and a Gilson P-20 manual pipettor. The elution buffer (100 microliter total volume), which consisted of 0.1% formic acid in a 1:1 mixture of methanol and water, was transferred to an autosampler vial equipped with a glass insert, for analysis by HPLC/MS (Table 10, bottom).

Example 17

Purification of Selected Peptides

Figure 15:
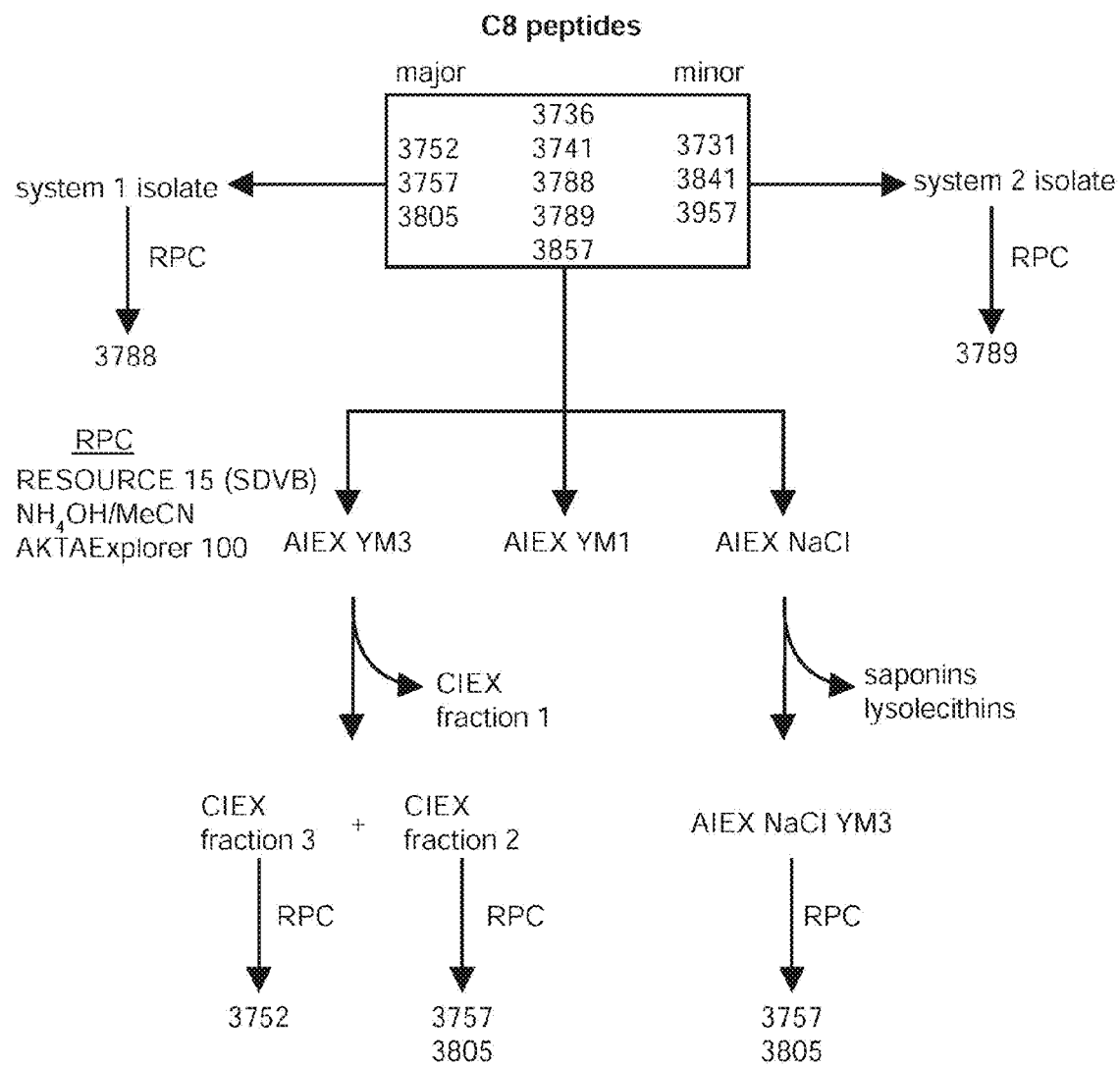
FIG. 15 shows examples of strategies employed in the purification of selected peptides found in C8 extracts of field peas.

Peptide-enriched isolates obtained by either flash or ion exchange chromatography were purified by RPC at pH 10.5 to obtain samples of high purity peptides of mass 3752, 3757, 3788, 3789 and 3805. The overall strategies involved in purification of these C8 peptides are summarized (FIG. 15).

Under the conditions of RPC (see Example 29), enriched samples of the C8 peptides were adequately resolved to be able to collect highly purified samples of the five target peptides. Their elution order during RPC was 3752, 3757, 3805, 3789 and 3788. The success of these purifications was dependent on the use of previously enriched peptide fractions otherwise the isolates could be contaminated with minor peptides. For example, peptides of mass 3736 and 3857 appeared to coelute with the peptide of mass 3757 as did peptides 3731 and 3788. The minor peptide of mass 3741 appeared to elute between the 3805 and 3789 peptides. The peptide of mass 3752 could possibly be isolated directly from crude peptide mixtures (C8 or AIEX YM3) because it eluted before the other peptides. However, the relative retention time of the minor peptide of mass 3957 could not be determined during RPC.

Figure 16:
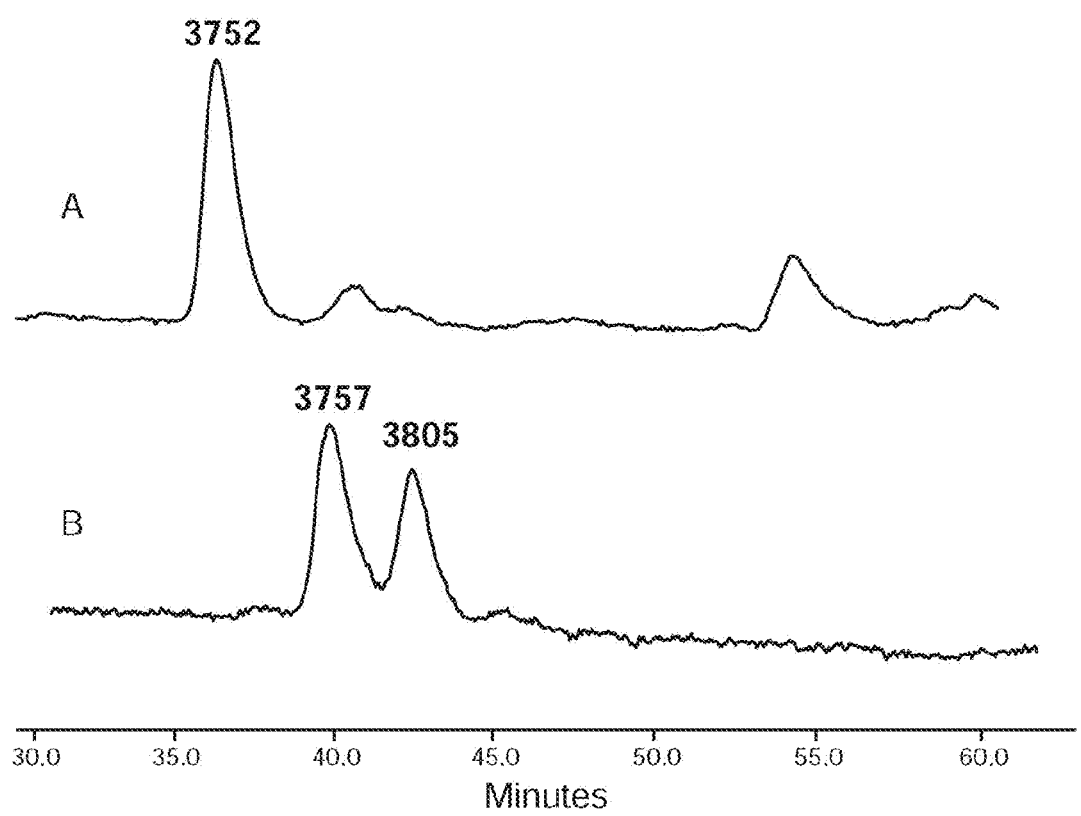
FIG. 16 shows a chromatogram (280 nm traces) illustrating the separation by medium pressure reverse phase chromatography (Resource 15 RPC column) of peptides found in (A) cation exchange fraction 3 and (B) cation exchange fraction 2. Chromatographic conditions were the same as in FIG. 6. About 1.6 mg of each sample dissolved in 80% methanol was injected. The main peaks that were isolated are identified by their molecular mass, determined by mass spectrometry.

FIG. 16 illustrates the purification by RPC of the 3752 (trace A) and 3757/3805 (trace B) peptides. After anion and cation exchange chromatography, RPC showed that CIEX fraction 3 was enriched in the 3752 peptide whereas CIEX fraction 2 yielded a mixture of the 3757 and 3805 peptides, in agreement with the results from Table 10. Although fraction 3 contained later eluting peptides, collection of the first peak gave a highly purified sample of the desired 3752 peptide (0.67 mg from a total of 4.96 mg injected). In a similar manner, fraction 2 yielded pure samples of the 3757 (0.43 mg) and 3805 (0.31 mg) peptides (4.93 mg injected). These 3 peptides were major components in crude C8 extracts.

The peptide fraction that eluted during application of the salt gradient during anion exchange chromatography (AIEX NaClYM3) was also subjected to semi-preparative RPC. Two main peptides were isolated (0.3 mg and 0.19 mg from 4.88 mg injected) and were shown by MALDI mass spectrometry to be of mass 3805 and 3757 respectively. The occurrence of these two peptides in both the flowthrough and salt retained fractions was quite unexpected. A possible explanation could be related to complex formation between the peptides and the saponins. Such a complex would be expected to have different properties from the native peptides during anion exchange chromatography. During RPC at alkaline pH, the complex apparently dissociated to some extent, leading to isolation of the two native peptides. RPC on AIEX NaCl YM3 showed that most of the other peptides were present, albeit in relatively low concentrations. It therefore appeared that the peptides of mass 3805 and 3757 had a greater propensity than the other peptides to complex formation. Another explanation might be related to the relative ease of dissociation of the various peptide-saponin complexes.

Higgins et al. (1986) have studied pea albumins in detail. Some of the chemical properties of pea albumins are shown (Table 11).

The peptide of mass 3788 was of particular interest because its molecular weight was the same as that of PA1b described by Higgins et al. (1986). During RPC, the 3788 peptide was found in highest concentrations in the end fractions from silica gel flash chromatography of C8 with chloroform-water-methanol and then methanol as eluent (system 1 isolate). A pure sample of this peptide was obtained (0.74 mg) by RPC on the system 1 isolate (3.54 mg injected). Additionally, the 3789 peptide was obtained (0.22 mg) from the system 2 isolate (4.56 mg injected) but the isolated sample was unstable on storage as judged by HPLC and mass spectrometry.

Example 18

Analytical HPLC with XTerra Columns

Figure 17:
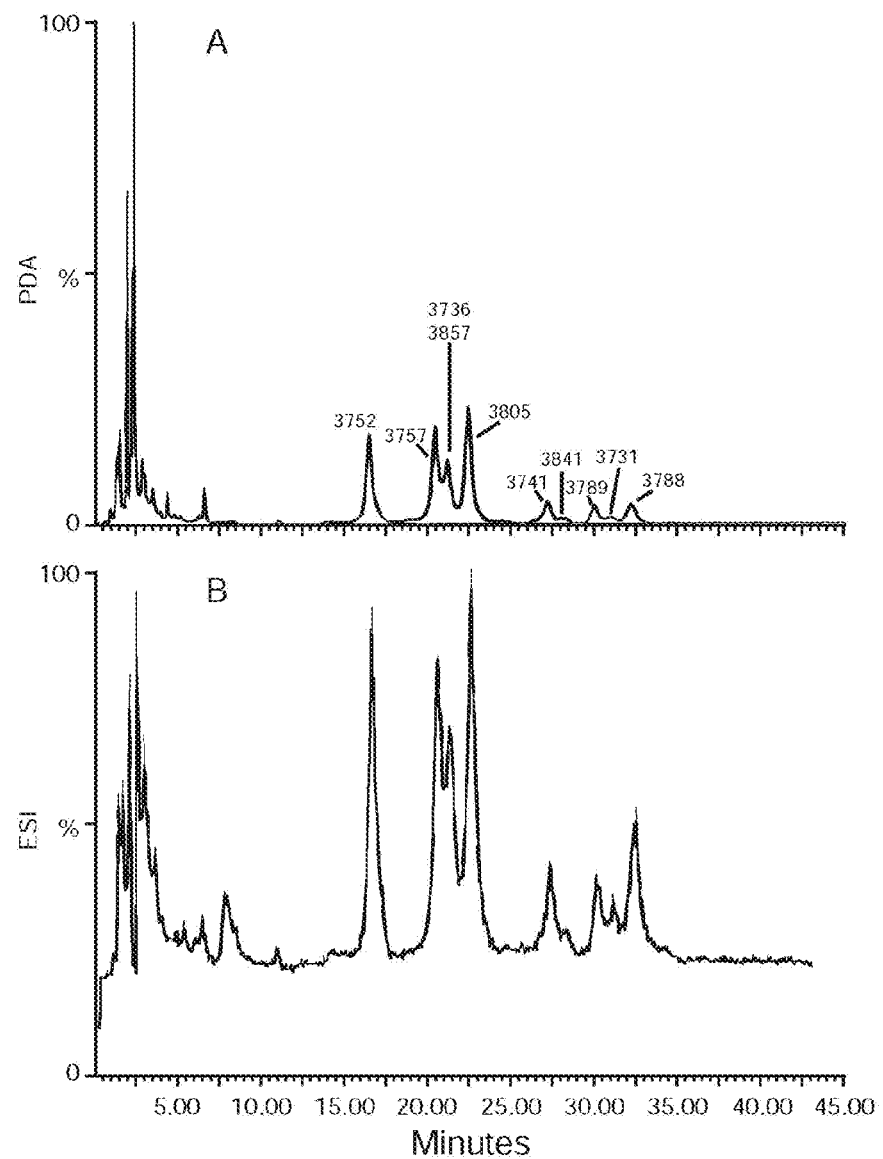
FIG. 17 shows a separation by HPLC/MS of pea peptides in a sample of AIEX YM3 (0.5 mg/ml dissolved in 80% methanol and diluted with an equivolume mixture of 10 mM ammonium hydroxide in water and 10 mM ammonium hydroxide in 80% acetonitrile) with a Waters Xterra™ RP-18 column (2.1×150 mm, 3.5 micrometer particle size). Trace (A) represents a total PDA chromatogram (sum of the absorbance from 1.95400 nm) whereas trace (B) is a total ion chromatogram obtained during electrospray ionization (ESI detector). The traces were recorded concurrently with the same sample. The top trace is labeled with the peptide masses found by electrospray mass spectrometry.

C-18 HPLC columns that are stable over a wide pH range have recently become commercially available and their utility in peptide separations at alkaline pH has been recognized (Agilent Technologies, 2000). The present work established that Waters XTerra™ RP18 columns, operating at 50° C. with a gradient of aqueous ammonium hydroxide and acetonitrile, resolved most of the peptides of interest. Further, these elution solvents were compatible with electrospray mass spectrometry so it was therefore possible to confirm the mass of the separated peptides. This is illustrated with the peptide sample AIEX YM3 (FIG. 17), which shows chromatograms from the photodiode array detector (A) and from positive electrospray ionization current (B) from a single injection. As indicated, nine distinct peaks were observed under optimum conditions. Only the peptides of mass 3736 and 3857 coeluted. This technology was useful to obtain the distribution of peptides in C8 samples and in the various chromatographic fractions derived from this material (see FIG. 15) without the need to rely on co-chromatographing peptides observed during TLC (see Table 9) or Symmetry HPLC (see FIG. 8). Results from analysis of these samples with XTerra columns are shown (Table 12). XTerra HPLC and HPLC/MS were also useful to assess the purity of peptide samples isolated by RPC for sequencing.

Example 19

Accurate Mass Determinations on Purified Peptides

Since the purified peptide of (average) mass 3788 corresponded to that of the linear, 37 amino acid PA1b (see FIG. 23), it was reasonable to conclude that PA1b itself or an isobaric variant (isoform) of PA1b of the same (or nearly the same) molecular mass had been isolated. It also seemed reasonable that the other isolated peptides of lower or higher mass were sequence variants of PA1b because Higgins et al. (1986) had shown that two or three amino acid substitutions were possible at 10 sites in PA1b (boldfaced in FIG. 23), always with conservation of the 6 cysteine residues (3 disulfide bonds). Within these constraints of Higgins et al. (1986), it was easy to show that 3456 variants (including isoforms) of PA1b were possible ($3 \times 2 \times 2 \times 2 \times 2 \times 2 \times 3 \times 2 \times 3 \times 2 = 3456$) and that these variants in theory would span an average molecular weight range of 3618-4023 Daltons. All of the detected peptides in C8 extracts (see Table 12), ranging in molecular weight from 3733-3957, were well within that mass range. The accurate masses, calculated with the aid of a spreadsheet for each of the 3456 possible variants, ranged from 3615.5608-4020.7411.

To assist in the sequencing of the four purified peptides, their accurate (monoisotopic) masses were determined by MALDI mass spectrometry in reflectron mode (Table 13). Following these determinations and considering that the mass accuracy with the spectrometer was ±0.2 Daltons, the sequences in the spreadsheet that corresponded to the accurate mass of an isolated peptide were selected as possible variants. This strategy resulted in selection of a reasonable number of likely sequence variants. For example, 30 sequences for the 3788 peptide that fell within the selected mass range (FIG. 18) were identified. Each of the other peptides showed 4-14 possible variants (see Table 13).

Example 20

Considerations for Peptide Sequencing by MALDI Mass Spectrometry

MALDI mass spectrometry was used to obtain amino acid sequence information after the purified peptides (reduced with dithiothreitol and alkylated with iodoacetamide) were incubated with commercially-available peptidases under various conditions, details of which are given in Example 29. Exopeptidases gradually shorten peptides at either one of their termini, creating C-terminal (carboxypeptidases A, P and Y) or N-terminal (aminopeptidase M) sequence ladders that are analyzed directly by MALDI mass spectrometry (Gevaert and Vandekerckhove, 2000). Sequence information was also obtained by employing endoproteinase Asp-N, a site-specific endopeptidase that cleaves peptides at the amino side of aspartic acid. Additionally, use was made of pronase, a proteolytic enzyme mixture containing carboxypeptidases, aminopeptidases and endopeptidases (Marzilli et al., 2000). Fragments from pronase digests were also sequenced by MALDI post source decay (PSD), a relatively new technique (Brown and Lennon, 1995) that generates amino acid immonium ions (to aid in determining amino acid compositions) as well as series of N-terminal product ions (a-, b-, c- and d-type fragments) and C-terminal product ions (x-, y- and z-type fragments). Since PSD fragmentation mainly occurs at peptide bonds, b- and y-type fragment (decay) ions are predominantly observed in MALDI-PSD spectra and are perhaps the most useful ions for sequencing peptides directly. With some peptides, y-ions representing uninterrupted sequences of 20 or more amino acid residues can be found (Keough et al., 1999). Internal fragments, representing two or more amino acids derived from neither termini, are also observed in MALDI PSD spectra.

In theory, ladder sequencing with exopeptidases results in the sequential hydrolysis of C- or N-terminal amino acids and the quasimolecular ions of resulting peptide fragments are detected in the incubates by MALDI mass spectrometry. In practice, the detection of every possible peptide fragment is rarely possible, mainly because the peptidases have different specificities towards peptide bonds. According to the manufacturer (Roche Diagnostics), aminopeptidase M does not cleave at the amino side of proline, alanine, glutamine or aspartic acid containing peptides whereas the C-terminal release of glycine and aspartic acid is considerably retarded with carboxypeptidase Y. Carboxypeptidases P and Y do not readily cleave long peptides and or those with disulfide bridges (Bonetto et al., 1997). Using mixtures of carboxypeptidases P and Y, the present inventors have found that degradation of peptides containing carboxymethylated cysteine residues was terminated one residue before the cysteine. One can therefore expect to encounter gaps in mass spectral data during sequence determinations of complex peptides.

Example 21

Sequencing of the 3788 Peptide

Analysis of the purified 3788 peptide sample by reflectron MALDI confirmed the close match between the monoisotopic mass (3785.6) and that of PA1b (3785.7). However, the spreadsheet calculations showed 30 sequence variants with monoisotopic masses in the range of 3785.58 to 3785.74 Da (FIG. 18). Based on amino acid composition at positions 1, 11, 31 and 36, the isoforms were segregated into five groups, labeled a-e.

Linear MALDI analysis of enzyme-depleted incubates showed not only a strong MH+ ion (at m/z 4138) but also a weaker ion that corresponded to the loss of glycine (at m/z 4081). Since this loss appeared to be independent of the nature of the matrix, laser power and buffer, the sample may have contained small concentrations of a truncated peptide. This impurity was also detected by electrospray mass spectrometry.

It was apparent that information on amino acid composition, particularly on glutamic acid, lysine, methionine and threonine occurring only in isoforms of PA1b, would help to establish the sequence. Of these amino acids, immonium ions from PSD experiments provided evidence for the presence of lysine (ions at m/z 84 and 129), suggesting that PA1 b itself had not been isolated.

C-terminal sequencing (Table 14) showed tyrosine at position 36, thus eliminating the 10 sequences of group e. The occurrence of lysine (at position 31) was supported by experiments with carboxypeptidase P, thus excluding the 11 sequences of group d. These enzymes provided good sequence coverage, although considerable differences in specificity were apparent.

N-terminal sequencing (Table 15) indicated alanine at position 1, which excluded the five sequences of group c. These enzymes did not give good sequence coverage, likely due to blockage by cysteine at position 3.

Incubation of the peptide isolate with pronase, a proteolytic enzyme mixture containing carboxypeptidases, aminopeptidases and endopeptidases, gave two main fragments at m/z 2353 and 1804. These fragments could be rationalized by the occurrence of amide hydrolysis at arginine-cysteine (positions 21 and 22). The two possibilities of group b, containing glutamic acid at position 11, were excluded by use of endoproteinase Asp-N, a commercially-available enzyme that hydrolyzes peptides at the amino side of aspartic acid. With the proposed sequence, the peptide bond of phenylalanine-aspartic acid would be hydrolyzed, leading to expected ions at m/z 3058 and 1099. These ions were indeed observed. Absence of an immonium ion for methionine (at m/z 104) reduced the two possibilities of group a to one, leading to a tentative sequence (see FIG. 18, top).

The peptide of m/z 2353 found in pronase digests was sequenced by PSD analysis. This 21 amino acid peptide gave strong C-terminal product ions corresponding to y9, which confirmed isoleucine (rather than methionine) at position 12. Fragmentation efficiency is known (Keough et al., 1999) to decrease considerably at amide bonds on the C-terminal side of proline. Consequently, PSD fragment ions at proline sites (y3, y7, y8 and y12) were very weak. Several of the y ions appeared to lose ammonia (y-17). An incomplete set of N-terminally charged b ions (b3-b8) were found and were often accompanied by ions representing the loss of water (b-18). Nearly all of the internal fragments contained proline. The smaller peptide found in pronase digests, representing the 16 amino acid sequence of 1803.2 Da (Table 15), gave a complete set of y ions with one exception (y15). These data helped to confirm the sequence.

Example 22

Sequences of 3757 and 3805 Peptides, and Considerations for Sequence of 3752 Peptide These peptides were also sequenced by a combination of MALDI mass spectrometry and digestion with proteolytic enzymes, especially with pronase. These peptides were initially considered as possible variants of PA1b, like the 3788 peptide (iso PA1b). With their accurate masses available, the variant possibilities from spreadsheet calculations showed ten possible variants of 3752, ten of 3757 and four of 3805 (Table 13). However, it became apparent that the model of PA1b (see FIG. 23, top) could not account for the observations from mass spectral data and needed to be modified. For example, the 3752 peptide was shown (both before and after reduction and alkylation) to contain histidine by the appearance of a PSD immonium ion at m/z 110, an ion that is characteristic for this amino acid. Although 3757 and 3805 did not appear to contain histidine, their immonium ion spectra were not definitive with regard to the presence of other possible (according to the model) amino acids, especially methionine, glutamic acid, aspartic acid and threonine. The oxidized form of methionine, methionine sulfoxide (m), was also considered but the immonium ion of m occurs at the same mass as the immonium ion of phenylalanine (m/z 120), the latter of which is always found at position 10 of PA1b and variants.

Before reduction and alkylation, the purified samples of the 3 peptides when examined by high resolution MALDI mass spectrometry (reflectron mode) gave not only the expected quasimolecular ions (Table 13) but also ions of lesser intensity that corresponded to the loss of approximately 57-64 mass units. Initially, this was a puzzling observation because purified samples of 3788 (MH+ 3789) were shown under linear MALDI and electrospray ionization conditions to contain a truncated species at m/z 3732 corresponding to the loss of the C-terminal glycine (3789-57 mass units). In linear MALDI experiments with the current peptides dissolved in buffers for incubation (enzyme-depleted treatments), ions that corresponded to both MH+−57 and MH+−64 were observed, suggesting that these peptides contained not only peptide impurities without a C-terminal glycine but also another structural feature to explain the loss of 64 mass units. Since an ion corresponding to MH+−64 was not observed in MALDI spectra of 3788, one could conclude that an amino acid, or modified amino acid, was unique to the 3752, 3757 and 3805-peptides. Further, this loss of 64 mass units was also observed during MALDI mass spectral analysis of cleavage products from pronase digestions (containing the amino acids 1-21 of PA1b and variants) and represented a predominant ion during MALDI PSD analysis on proteolytic (N-terminal) fragments. In MALDI experiments on a methionine-containing enolase, Larsen and Roepstorff (2000) showed that the facile loss of 64 mass units can be attributed to fragmentation of methanesulfonic acid ($CH_3SOH$) from an oxidized methionine residue in the peptide. This loss is also diagnostic for oxidized methionine under electrospray MS-MS conditions (Xiangyu et al., 1996). The MH+−64 ion is recognized as diagnostic for methionine sulfoxide in current mass spectrometry software packages for peptide sequencing, such as ProteinProspector™ (http://prospector.ucsf.edu). Identification of oxidized methionine was consistent with that residue, rather than methionine or isoleucine, occurring at position 12 in variants of PA1b.

Spreadsheet calculations obtained for the 3757 peptide with methionine sulfoxide at position 12 showed that there were seven variant possibilities within the specified accurate mass range, all with serine at position 36 (FIG. 19). Ladder sequencing with aminopeptidase M showed alanine as the N-terminal amino acid. Hence, the sequences with isoleucine or valine at position 1 (group b) could be eliminated. Two sequences of group a were easily eliminated on examination of pronase digests. Not only was a C-terminal ladder fragment found at m/z 2733.1 corresponding to valine at position 25 but also fragments were observed at m/z 2362.7 and 1763.1, corresponding to endoproteolytic hydrolysis at the C-terminal side of arginine at position 21 (Table 16). These two sequences of group a would yield peptides of mass 2390.7 and 1734.0 Daltons which were not observed. Supporting evidence for the sequence of 3757 (FIG. 19, top) was obtained by PSD experiments on the fragments observed at m/z 2362.7 (y1 to y10, y11-64, y15, y20) and 1763.1 (y1 to y8, y10, y13, y14).

Endoproteinase Glu-C, also known as *Staphylococcus aureus* V8 protease, appeared to be a useful commercial enzyme to confirm the presence of glutamic acid at position 11 because it specifically cleaves at the carboxyl side of glutamic acid in ammonium bicarbonate buffer (pH 7.8). With the 3757 sequence, this would be expected to lead to fragments at m/z 1228.3 and 2897.4. In experiments with this enzyme, the latter ion was found in relatively small abundance but mostly a complex mixture of N- and C-terminal fragments were observed in 6 hour incubates (Table 16). A strong molecular ion was also present. It appeared that the Glu-C showed little selectivity towards cleavage at glutamic acid in this peptide. This could be related to steric hindrance from the adjacent methionine sulfoxide residue (FIG. 19). The substitution of methionine sulfoxide for methionine has also been shown to decrease the rate of proteolysis in methionine-containing proteins related to Alzheimer's disease (Rapala-Kozik et al., 1998). Nevertheless, the variety of fragments obtained from digestions with Glu-C helped to confirm the sequence of 3757. It should be noted that pronase at pH 4 gave an ion at m/z 3026, corresponding to cleavage at the N-terminal side of glutamic acid.

The fourteen sequence possibilities for the 3805 peptide are shown in FIG. 20. Those of group c were eliminated because of tyrosine at position 36. Evidence for the presence of serine at position 36 was obtained from the abundant pronase fragment at m/z 3798.4 (C-terminal loss of GSPN, Table 17). In addition, the smaller fragment (observed at m/z 1811.1) from pronase hydrolysis at the internal arginine (position 21) showed an immonium ion for phenylalanine but not alanine. Group b peptides did not have alanine at position 1. Like the 3757 peptide, two of the sequences of group a would yield peptides of mass 2390.7 and 1782.1 which were not observed in pronase digests. Instead, prominent ions were found at m/z 2362.7 and 1811.1 (Table 17). Hence, the sequence of the 3805 peptide was established (FIG. 20, top) and differed from 3757 only in the residues at position 28 (see FIG. 23).

Digestion of the 3805 peptide with endoproteinase Glu-C gave the expected (but small) fragments at m/z 1228.3 and 2945.5 and, like 3757, many other N- and C-terminal fragments were observed (Table 17), several of which had the same mass as those from aminopeptidase M and pronase. The molecular ion was also strong, even after 9 hours of incubation. Pronase at pH 4 gave an ion at m/z 3073, corresponding to cleavage at the N-terminal side of glutamic acid.

Carboxyl terminal cleavages of the arginine residues at positions 21 and 33 would lead to internal fragments of CIPVGLVIGYCR (m/z 1407.7) [SEQ ID NO:61] for the 3757 peptide and CIPVGLFIGYCR (m/z 1455.8) [SEQ ID NO:62] for the 3805 peptide. These ions were observed in pronase digests conducted at pH 4, providing additional evidence for the assigned sequences.

Example 23

Sequence of 3752 Peptide

The main pronase hydrolysis products occurred at m/z 2348.6 and 1772.1 (Table 18). Although 35 sequence possibilities with methionine sulfoxide at position 12 were found from the spreadsheet calculations (Table 13), these were unlikely candidates because none contained histidine. To derive other potential sequences, it was first necessary to locate the position of histidine. Immonium ion spectra from MALDI PSD experiments on the main pronase fragments showed that histidine was located in the 1772.1 fragment. Histidine was considered for replacing asparagine at the fourth residue from the carboxyl end because a y3 ion (at m/z 260.1) was found that supported histidine rather than asparagine at that position (position 34 in PA1b). This possible substitution was also deduced from the reported cDNA sequence of PA1b (Higgins et al., 1986) and the amino acid sequence of leginsulin (Watanabe et al., 1994). Additional support was obtained from the appearance of additional y ions (y4-y8, with tyrosine at position 31 and serine at position 36) during PSD analysis on the m/z 1772.1 fragment. Despite these considerations, sequences for the 3752 peptide could not be found from the published PA1b model that fit the masses of the two main pronase hydrolysis products.

C-terminal cleavages by pronase provided good evidence for the YCRH sequence at positions 31-34 (Table 18) but the remaining sequence (to position 22) of the 1772.1 fragment needed additional study. In this regard, a prominent ion at m/z 1245.4 was found in pH 8 pronase digests that was considered to represent positions 27-37, supported by the complimentary hydrolysis product at m/z 2875.3 representing the remainder of the 3752 peptide. The 1245.4 fragment was selected for MALDI PSD analysis and the appearance of y2-y8 ions helped to support the sequence from positions 30-37 (GY-CRHPSG). Valine was almost certainly present at position 28 because this fragment showed an immonium ion characteristic of valine, not phenylalanine. Positions 27-29 were therefore considered to be LVV (311 Daltons) although the isobaric LTP or LPT were remote possibilities. Support for the former sequence came from the b2 and b3 ions observed during PSD experiments on the m/z 1245.4 ion. PSD fragment ions corresponding to b4, b7, b8 and b10 were also observed.

Figure 22:
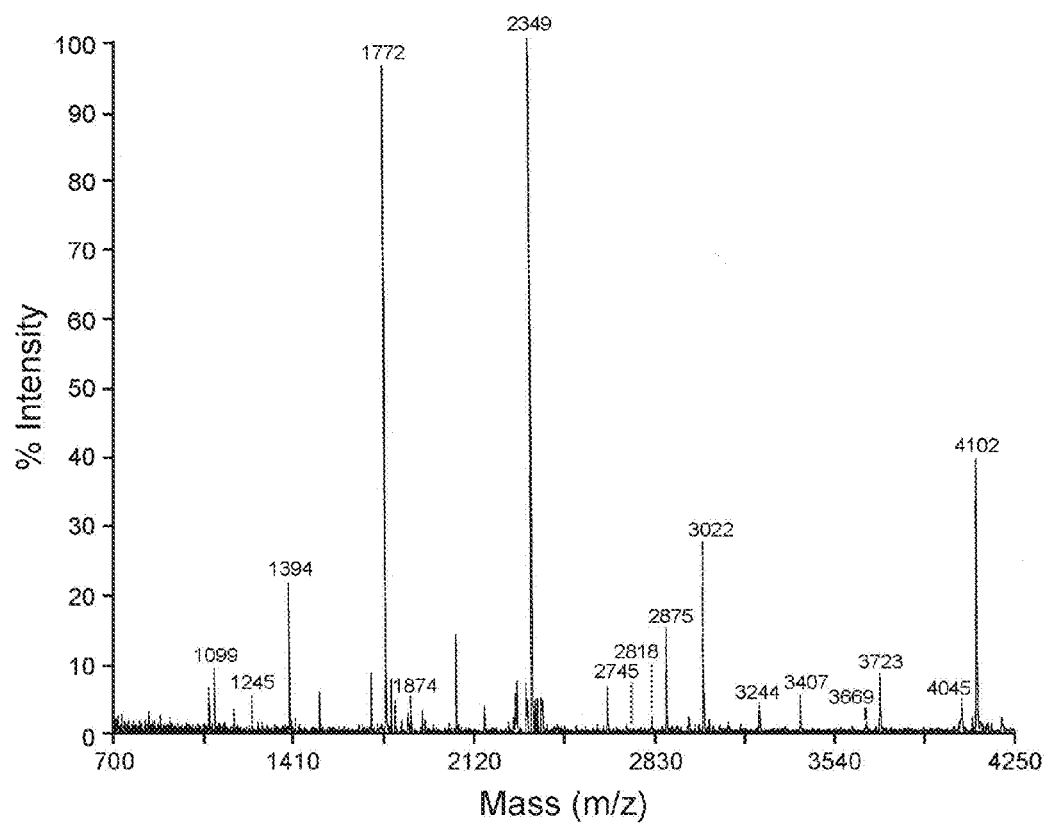
FIG. 22 shows a MALDI mass spectrum obtained from the analysis of a pronase digest from a 3752 peptide. The subsample for analysis was taken after 10 minutes at pH 4, with an enzyme to substrate ratio (w/w) of 1 to 10.

The remainder of the sequence (positions 22-26) for m/z 1772.1 was supported by b1-b5 ions corresponding to CIPVG. Additional PSD fragment ions attributed to b6-b10 and b13 were also found. Carboxyl terminal cleavages of the arginine residues at positions 21 and 33 would lead to an internal fragment of CIPVGLVVGYCR (m/z 1393.7). This ion was indeed observed in pronase digests conducted at pH 4 (FIG. 22), providing additional evidence for the assigned sequence. Valine at position 25 was conserved in all four peptide samples (see FIG. 23).

With residues at positions 22-37 established, spreadsheet calculations were performed as before using the allowed substitutions at positions 1, 11, 12, 17, 18 and 19 of PA1b. This resulted in 6 sequence possibilities for the 3752 peptide (FIG. 21). Those of group b were discounted because aminopeptidase M showed that alanine was at position 1. In group a, the third sequence had alanine at position 25. The second sequence with TSA at positions 17-19 (and Dm at 11-12) was excluded during PSD experiments on the main pronase fragment at m/z 2348.6. The C-terminal y and y-17 ions supported the SSA sequence, as evidenced by observing these ions (y1-y10) for the sequence of 3752 shown at the top of FIG. 21.

Endoproteinase Glu-C gave a small ion at m/z 2892.4, corresponding in mass to the larger fragment from cleavage at the C-terminal side of glutamic acid. A number of nonspecific but readily assigned fragments were detected (Table 18). The molecular ion was strong after 9 hours of incubation with this enzyme. Like the 3757 and 3805 peptides, pronase at pH 4 gave an ion at m/z 3021.5 (labeled 3022 in FIG. 22), corresponding to cleavage at the N-terminal side of glutamic acid.

Example 24

Peptide Interrelations

Sequences of the four peptides identified in C8 extracts are collected in FIG. 23. For comparison, FIG. 23 also shows the sequence (and variant possibilities) of PA1b from Higgins et al. (1986), the reported sequence of protéine PT, an insecticidal pea peptide isolated by Delobel et al. (1999) and the sequence of leginsulin, a related soybean peptide (Watanabe et al., 1994). The latter peptide provided a precedent for the occurrence of valine at position 29 and histidine at position 34, as was found for the 3752 peptide.

The reported sequence of protéine PT (3741 average mass) is the same as the deduced sequence of the major 3757 peptide, except for the state of oxidation of methionine at position 12. In that regard, one could sort most of the major and minor peptides of C8 extracts (see FIG. 17) into similar pairs, differing in mass by 16 Daltons (Table 19). Thus, the minor 3736 peptide likely represents the unoxidized form of the major 3752 peptide and the minor 3789 peptide likely represented the unoxidized form of the major 3805 peptide. The conversion of methionine to methionine sulfoxide is known to increase the hydrophilic properties of peptides (Schenck et al., 1996) and this was reflected by shorter retention times for the oxidized pea peptides during XTerra HPLC at pH 10.5 (Table 19 and FIG. 17). The peptide mixtures were never adequately resolved during Symmetry HPLC at pH 2 (see FIG. 8).

Oxidation of methionine to methionine sulfoxide can occur both in vitro and in vivo (Brot and Weissbach, 2000). Even atmospheric oxygen can oxidize methionine residues (Manning et al., 2002). In vivo, the oxidation may be promoted by reactive oxygen species (Sochaski et al., 2001) or other oxidizing agents normally produced by cells (Ciorba et al., 1997). The presence of methionine sulfoxide residues may lead to significant conformational changes in proteins (Gustavsson et al., 1999) and peptides (Schenck et al., 1996). The biological activities of a large number of proteins and peptides are affected by the state of oxidation of methionine residues and, frequently, the presence of methionine sulfoxide causes a loss of function (Brot and Weissbach, 2000). The oxidation of proteins and peptides can be reversed by the ubiquitous enzyme, methionine sulfoxide reductase.

Although chemical reagents such as hydrogen peroxide and t-butylhydroperoxide are capable of oxidizing methionine-containing proteins (Liu et al., 1998), including heat shock protein from plants (Gustavsson et al., 1999), it was unclear if laboratory processing of plant tissues could promote methionine sulfoxide formation. In the present work, all of the C8 extracts examined by XTerra HPLC showed a similar peptide profile, with the oxidized peptides appearing as the major components in each C8 sample. Although some aerial oxidation (Manning et al., 1989) may have occurred, for example during hot methanol extraction or C8 clean-up steps, one would have expected considerable between-sample variability in the peak area distribution of the oxidized and reduced peptides if the samples underwent partial aerial oxidation in the laboratory. Samples of C8 obtained from different batches of flour were remarkably similar (see Table 12, bottom). Furthermore, both Higgins et al. (1986) and Delobel et al. (1999) did not discuss any methionine sulfoxide-containing peptides, although their laboratory isolation and purification procedures were quite extensive. These authors performed the extractions (with 60% methanol or 0.1 M sodium acetate buffer) on whole or laboratory-ground peas, in contrast to the present work with air classified protein-rich pea flour from a commercial mill (Parrheim Foods Ltd). It was therefore reasonable to conclude that the oxidized peptides were formed in large part during the processing of peas in the mill. The significance of the oxidized peptides in purification of C8 peptides has been described (Example 17).

Example 25

Figure 24:
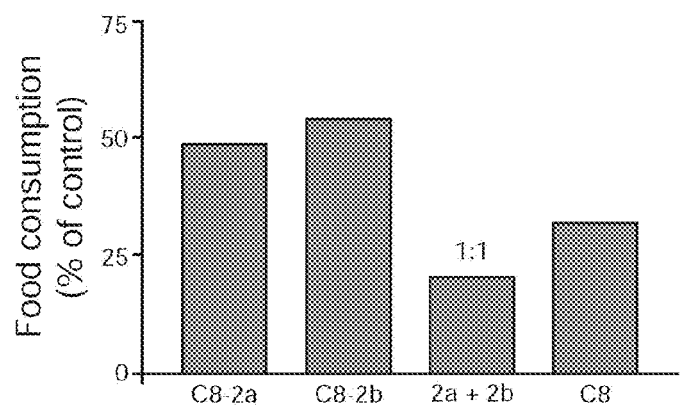
FIG. 24 shows antifeedant activity against *S. oryzae* of a saponin enriched fraction (C8-2a), a peptide fraction (C8-2b or system 1 peptide isolate), a 1:1 mixture by weight of C8-2a and C8-2b and crude C8. In each treatment, the dose was 1.6 mg/200 mg flour. Fractionation was achieved on C8 powder by silica flash chromatography with solvent system 1.

Enhancement of Antifeedant Activity on Mixing Saponin and Peptide Fractions Several examples of the present invention had already indicated that the highest antifeedant activity tended to be associated with mixtures containing soyasaponins, lysolecithins and peptides. To examine the possibility that the activity of the insecticidal peptides was increased by the presence of one or more of the inactive components, the experiment shown graphically in FIG. 24 was performed using extracts that were isolated from C8 by flash-chromatography with solvent system 1 (see Table 2). The two main fractions, C8-2a (composed of mostly soyasaponins) and C8-2b (a ninhydrin positive system 1 isolate shown to be a mixture of peptides), were tested after mixing equal amounts in 70% ethanol. This mixture, evaluated against S. oryzae at a total dose of 1.6 mg/200 grams of flour, was found to be more active compared to C8-2a, C8-2b and impure C8 in the same bioassay at the same dose. This meant that a synergistic interaction was occurring between the C8-2a and C8-2b extracts. Without wishing to be bound by theory, the synergistic interaction was probably between a saponin and a peptide component.

Example 26

Synergy Experiments with Purified Soyasaponin I

These bioassays were designed to check qualitatively for synergism with the main peptide isolates and soyasaponin I. Bioassays with S. oryzae were run with samples containing pea peptide isolates without soyasaponin I (1:0 peptide/soyasaponin I ratio), with samples prepared as mixtures of pea peptides and soyasaponin I (typically with ratios by weight of 9:1, 7:3, 1:1, 3:7 and 1:9) and with samples of only soyasaponin I (0:1 ratio). Soyasaponin I from defatted soybean flour had been purified by procedures a-d of Example 5.

System 1 and 2 peptide isolates were found to be synergized by soyasaponin I (FIG. 25). As the proportion of peptides decreased and the proportion of soyasaponin I increased in the test mixtures, the activity remained nearly constant up to a ratio of 1:9. As expected, food consumption increased dramatically when only soyasaponin I was present (0:1 ratio). In the absence of synergy, one would of course expect the curve to rise in a gradual way on progressing to higher concentrations of soyasaponin I (lower concentrations of peptides).

It should be noted that the system 1 peptide isolate appeared to be more strongly synergized than the system 2 peptide isolate. However, bioassays on these two isolates were performed on different days and some day-to-day variability was expected with insect bioassays of this type. Furthermore, the system 2 isolate by itself (1:0 ratio in FIG. 25) was somewhat less active than in previous experiments (see Table 8, fraction 3) when the material was tested alone at the standard dose (1.6 mg/200 g of flour). This reinforced the probability that the rice weevils were less sensitive to treatments during the tests with the system 2 peptide isolate.

It was also found that soyasaponin I enhanced the antifeedant activity of both the AIEX YM3 peptide and crude C8 isolates (FIG. 26). It could be concluded that this saponin, throughout a range of concentrations, acted as an effective synergist with the main isolates of pea peptides.

Figure 27:
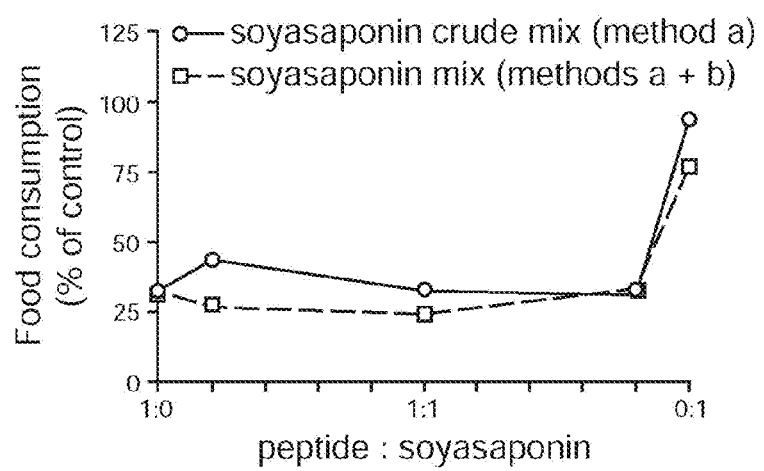
FIG. 27 shows antifeedant activity against *S. oryzae* of an anion exchange flowthrough isolate (AIEX YM3) when mixed at various proportions with a soyasaponin crude mixture neutralized with Dowex SOW (method b) and a soyasaponin mixture partially purified by Diaion HP 20 and neutralized with Dowex 50W (methods a+b). The total dose was 1.6 mg/200 mg flour.

Pure samples of soyasaponin I were obtained by time-consuming laboratory techniques so it was important to determine if impure samples of the soybean saponin isolate would synergize the pea peptides. Two soyasaponin samples, isolated as free acids, were obtained for testing from the sodium salt mixture isolated in the pilot plant (Example 5). These samples, when mixed with AIEX YM3 as the peptide source, gave a similar plot (FIG. 27) but the purer sample that had been treated with Diaion HP-20 and Dowex 50W was a slightly more effective synergist at low doses (9:1 and 1:1 peptide to soyasaponin ratios). This soyasaponin mixture appeared to be as effective as soyasaponin I in bioassays with the same peptide sample (see FIG. 26). With C8 as the peptide source, plots of the synergy tests comparing soyasaponin I to this soyasaponin mixture were nearly superimposable (FIG. 28). It is possible that minor saponins in this soybean isolate, such as soyasaponin II and III and dehydrosoyasaponin I, that were detected in the mixture by HPLC/MS, also contributed to the synergistic effect.

Figure 30:
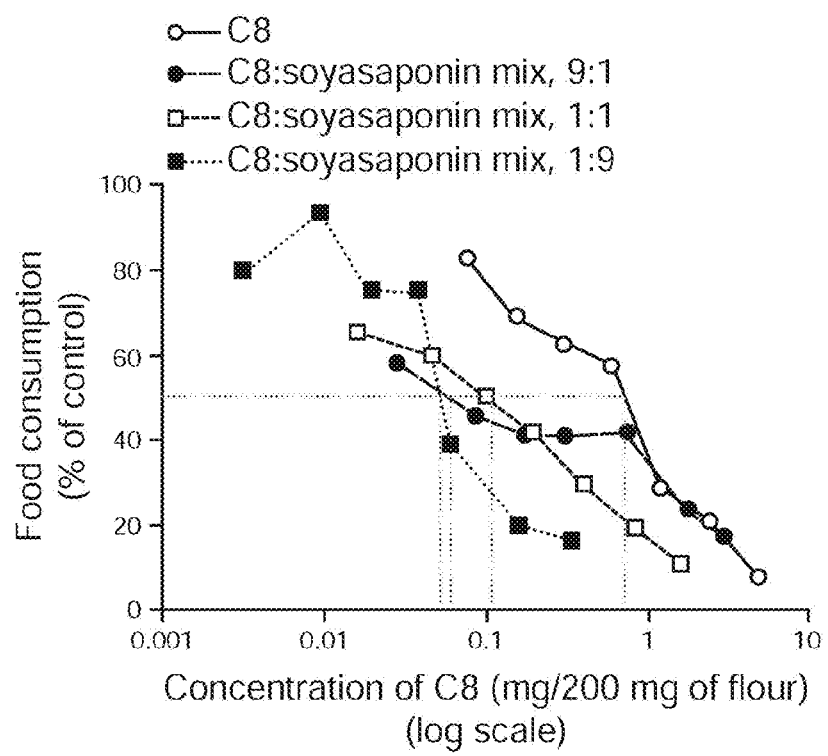
FIG. 30 shows a comparison of dose-response curves in antifeedant bioassays (*S. oryzae*) with a crude C8 isolate and the same C8 isolate mixed with a soyasaponin mixture partially purified by Diaion HP 20 and neutralized with Dowex SOW. The partially purified soyasaponin sample by itself gave food consumption values of 75-105% when tested over a wide concentration range (0.1-25.6 mg/200 mg flour).

Dose-response curves in antifeedant bioassays over a wide concentration range (approx. 0.01-10 mg/200 mg flour) comparing a C8 isolate alone against a combination of C8 isolate and a soyasaponin mixture (that is, Diaion HP-20 and Dowex 50W) demonstrated that the combination was synergistic (FIG. 30). The partially purified soyasaponin sample by itself gave food consumption values of 75-105% when tested over a wide concentration range (0.1-25.6 mg/200 mg flour).

Example 27

Bioassay Experiments with Other Triterpenoid Saponins

Figure 29:
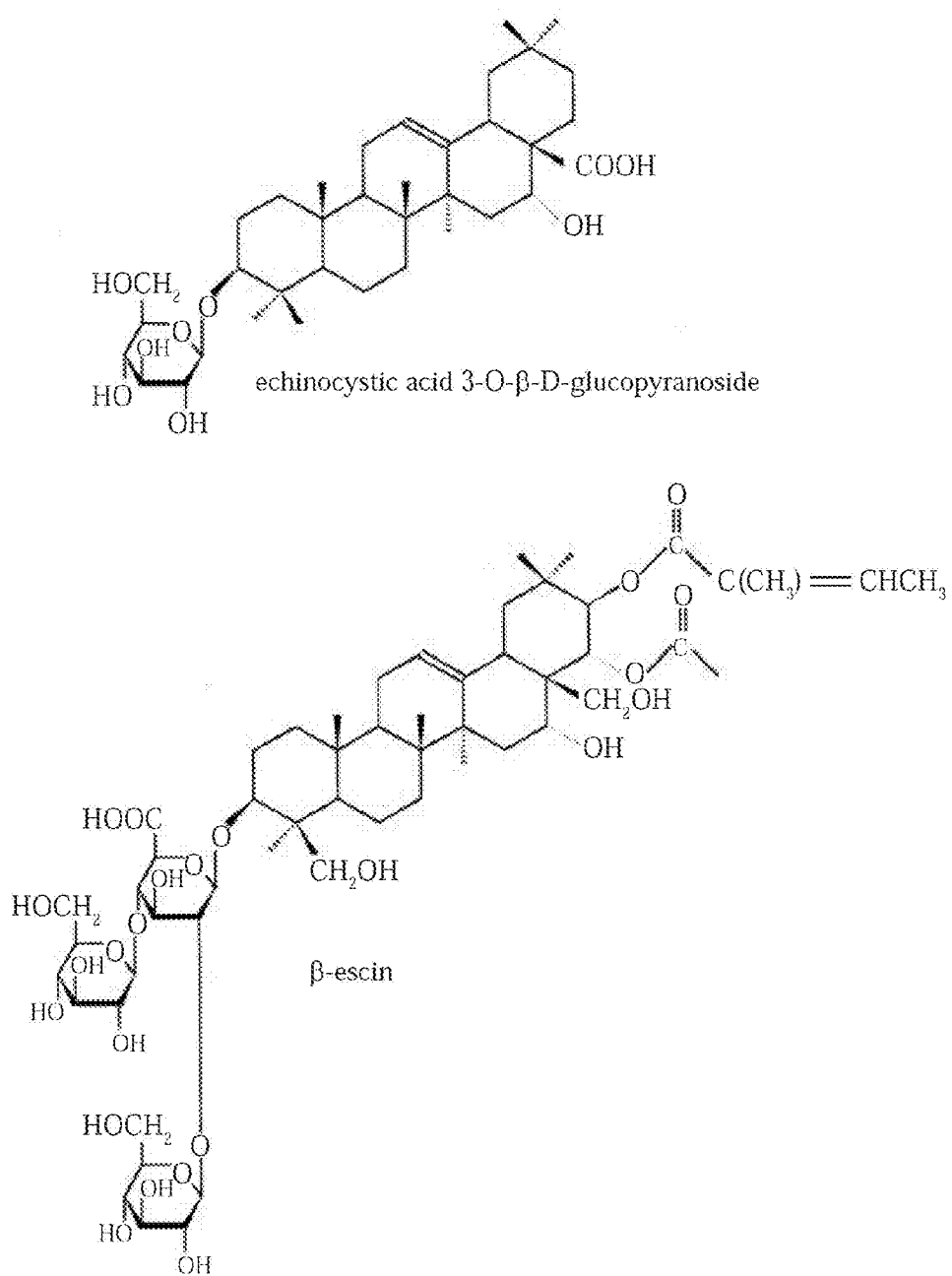
FIG. 29 shows structures of exemplary triterpenoid saponins.
Figure 29:
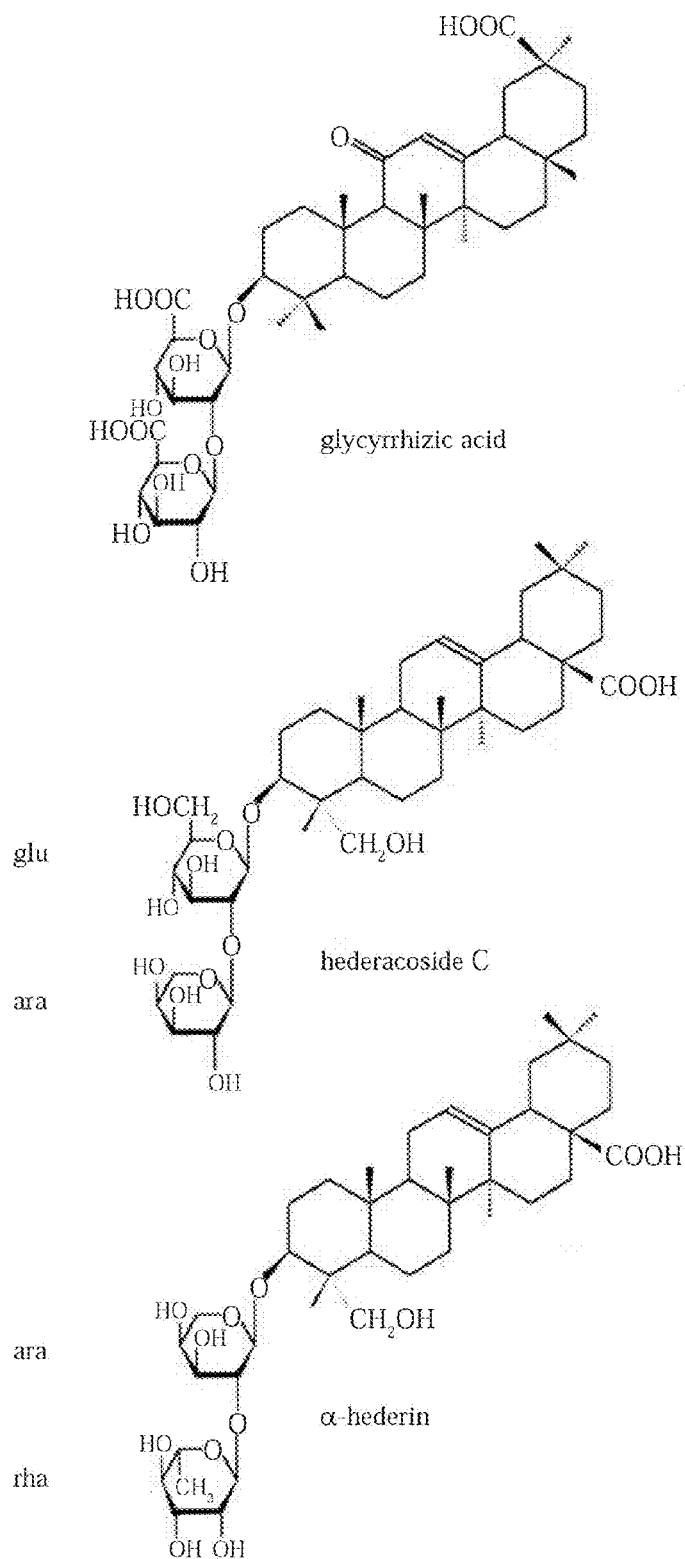

Dehydrosoyasaponin I (Example 9) plus five commercially available triterpenoid saponins (FIG. 29) were selected for antifeedant test and compared to isolated samples of soyasaponin I (Table 20). In initial treatments with the purified saponins alone, β-escin showed the best activity against rice weevils, followed by α-hederin, echinocystic acid 3-glucoside and dehydrosoyasaponin I. Hederacoside C, glycyrrhizic acid and soyasaponin I were inactive in these tests.

In single dose tests for synergy, utilizing pea peptide to saponin treatment ratios of 9:1, 1:1 and 1:9, it appeared that glycyrrhizic acid, hederacoside C and dehydrosoyasaponin I were clearly synergistic, but not as effective as soyasaponin I.

Example 28

Bioassay Experiments with Mixtures Containing Lysolecithins

Although the three identified lysolecithins (Example 7) were inactive antifeedants by themselves, it was of interest to test these compounds on mixing with the pea peptides and soyasaponins. Mixtures containing 90% lysolecithin and 10% peptides (AIEX YM3) were prepared and tested in flour disk antifeedant bioassays with rice weevils. The total dose ranged from 0.016-1.6 mg/200 mg of flour. Food consumption, expressed as % of untreated control, ranged from 71-115% (L-16:0), 67-134% (L-18:1) and 70-110% (L-18:2). Similar experiments, conducted with lysolecithin-saponin (soyasaponin I) mixtures, gave food consumption values of 84-102% (L-16:0), 87-92% (L-18:1) and 82-98% (L-18:2). These results suggested that the phospholipid compounds by themselves did not affect the peptide activity or soyasaponin I activity. However, lysolecithins were observed to enhance dehydryosoyasaponin I activity. Other saponin activities may be enhanced by the presence of lysolecithins.

Example 29

Exemplification of Methods Used to Isolate and Detect Insecticidal Activity

Bioassays.

Insect antifeedant activity was assessed with a flour disk bioassay (Xie et al., 1996) using rice weevils (*Sitophilus oryzae* L.). A test insecticidal compound is incorporated into flour disks. Typically 70% ethanol is used as a solvent with exemplary doses ranging from 0.01-25.6 milligram/200 milligram flour. A typical dose in many of the above examples is 1.6 milligram/200 milligram flour. Wheat flour is typically used.

There is a positive correlation between antifeedant activity and insecticidal compound toxicity. Reduction in feeding activity elicited by the experimental samples was compared to food consumption of untreated controls, obtained by weighing the disks before and after exposure to insects and expressed as percent feeding relative to the control. Bioassay can also include insecticidal measurements (lethality with rice weevil).

High Performance Liquid Chromatography (HPLC).

Samples were prepared in 80% methanol at 1-4 mg/ml and syringe filtered (0.45 µm pore size, nylon membrane type, Chromatographic Specialties, Brockville, Ontario) into 0.25 ml glass autosampler vial inserts (Fisher no. 03-375-3A). The solutions were maintained at 15° C. before injection (10 µl volume).

The instrument consisted of an Alliance 2690 separations module (Waters Canada, Mississauga, Ontario) equipped with vacuum solvent degassing, a Waters 996 photodiode array detector (PDA) and a PL-EMD-960 evaporative light scattering detector (ELSD) (Polymer Laboratories, Amherst, Mass.) controlled by Waters Millennium software. The PDA was operated at 195400 nm with resolution of 3.6 nm. Chromatograms were typically plotted with 210, 280 and 295 nm outputs. Settings for the ELSD were attenuation=1, time constant=1 second, temperature=90°, PMT level=6 and airflow-4 liters/min.

A reversed phase C-18 Symmetry™ column (3.0×150 mm, 5 µM particle size) purchased from Waters Canada and maintained at 30° C. was used for separations at acidic pH. The mobile phase consisted of 0.05% trifluoroacetic acid (TFA) in water (solvent A) and 0.05% TFA in acetonitrile (solvent B), delivered at a flow rate of 0.4 ml/min. The gradient elution program consisted of 95% A and 5% B at time 0. After 30 minutes, the composition was 5% A and 95% B (linear, curve 6 gradient), maintained at that proportion for 5 minutes. The gradient changed back to 95% A and 5% B from 35 to 43 minutes. Total run time was 45 minutes.

In later experiments with a Symmetry column, the above gradient was modified to give a composition of 65% A and 35% B after 10 minutes. At that time, the linear gradient progressed to 50% A and 50% B over 15 minutes and to 5% A–95% B over 5 minutes before reverting to 95% A and 5% B from 35 to 43 minutes. This gradient resulted in baseline separation of soyasaponin VI and dehydrosoyasaponin I.

HPLC experiments under alkaline conditions, employed for analytical separation of peptide mixtures (see Table 12), were performed with Waters XTerra™ C-18 columns (3.0× 150 mm, 5 or 3.5 µm particle size) maintained at 50° C. The mobile phases were 10 mM (0.035%) ammonium hydroxide in water (solvent A) and 10 mM ammonium hydroxide in 80% acetonitrile (solvent B), delivered at a flow rate of 0.4 ml/min. The gradient elution program consisted of 60% A and 40% B at time 0. After 35 minutes, the composition was 40% A and 60% B (5 µm column) or 55% A and 45% B (3 µm column) (linear, curve 6 gradient), maintained at those proportions for 5 minutes. The gradient changed back to 60% A and 40% B from 40 to 43 minutes. Total run time was 45 minutes.

Electrospray Ionization Mass Spectrometry (ESI-MS).

Positive ion electrospray ionization mass spectra were obtained with a benchtop tandem quadrupole mass spectrometer (Quattro LC, Micromass UK Limited) equipped with an atmospheric pressure electrospray ionization source interfaced directly to a Waters Alliance 2690 separations module. Nitrogen gas was used for nebulization and desolvation. The instrument was controlled by Micromass MassLynx software (version 3.3) running under Microsoft Windows NT. Micromass deconvolution software (MaxEnt) was used to process the spectra of peptide samples. The instrument was calibrated to unit resolution with myoglobin. Cone voltage was typically set at 20 V, capillary voltage at 3.5 kV and the mass range scanned was 300-2000 atomic mass units. Source block and desolvation temperatures were 110° C. and 350° C. respectively.

For HPLC/MS, a reversed phase C-18 Symmetry™ column (2.1×150 mm, 5 µm particle size) held at 30° C. was used. The mobile phase (flow of 0.2 ml/minute) consisted of water containing 0.1% formic acid (solvent A) and acetonitrile containing 0.1% formic acid (solvent B). The starting mixture was 95% solvent A–5% solvent B. A 20 minute linear gradient was applied, ending with 5% solvent A–95% solvent B and held for 5 minutes before recycling back to the original conditions. Samples were dissolved in 0.1% aqueous formic acid-acetonitrile (1:1) at a concentration of 1 mg/ml and 10 µl were injected with the autosampler. Some HPLC/MS experiments were also performed with the modified gradient (65% A and 35% B after 10 minutes, 50% A and 50% B over 15 minutes and 5% A–95% B over 5 minutes).

HPLC/MS experiments under basic conditions were performed with a Waters XTerra™ C-18 column (2.1×150 mm, 3.5 µm particle size) at 50° C. using the HPLC gradient already described for the 3.5 µm XTerra column. Samples dissolved in 80% methanol were diluted with an equivolume mixture of solvents A and B (1:1) to give a concentration of 0.5-1 mg/ml. The flow rate was 0.2 ml/minute.

Collision induced dissociation (CID) experiments were also conducted on the Quattro LC in the positive ion mode with argon as the collision gas with collision energies of 30-35 eV. For experiments with saponins, the Waters Alliance 2690 module was used for sample introduction (as above) but with a union replacing the C-18 Symmetry™ column. Solvent A and solvent B were delivered isocratically (0.2 ml/min) at a constant 1:1 ratio. Peptide samples were dissolved in 80% methanol at 10-20 pmole/µl and delivered to the ion source with an infusion pump. Formic acid (0.1%) was introduced with the 2690 and mixed with the peptides at the ion source. The rate of infusion was 10-20 µl/minute. Quasi-molecular ions (MH+) were used to generate daughter ion spectra.

Matrix-Assisted Laser Desorption/Ionization (MALDI) Mass Spectrometry.

Measurements were initially made with Voyager Elite and Voyageur DE-STR time-of-flight mass spectrometers (Perseptive Biosystems Framingham, Mass.) in positive ion linear (unit resolution) and reflector (high resolution) modes, both equipped with a nitrogen laser. The matrix solution consisted of α-cyano-4-hydroxycinnamic acid (20 µg/µl) in 90% acetonitrile, 10% water and 0.1% acetic acid. The instruments were calibrated with adrenocorticotropic hormone (ACTH fragment 7-38; average mass of 3659.16; monoisotopic or exact mass of 3656.92). Upper and lower mass to charge (m/z) gates were typically set at 2000-8000 atomic mass units (Daltons) (500-20000 Da in the linear mode). Processing of the spectra was performed with the Perseptive GRAMS 386 software.

All of the peptide sequencing experiments were performed on the Voyager DE-STR instrument equipped with updated acquisition (Voyager Instrument Control Panel, ver. 5.1) and processing (Data Explorer ver. 4.0) software. The instrument was operated in linear mode (typically from 800-5000 mass units) and was externally calibrated with angiotensin I, ACTH (1-17), ACTH (7-38) and bovine insulin. This instrument was also used for postsource decay (PSD) experiments.

Infrared (IR) and Nuclear Magnetic Resonance (NMR) Spectra

IR spectra were recorded on an ATI Mattson Genesis series FT-IR spectrometer, using potassium bromide disks. FT-NMR spectra were obtained (in pyridine-d5) with a Bruker AVANCE 400 spectrometer operating at 100 MHz (for carbon-13 spectra).

Reverse Phase Chromatography (RPC).

The medium pressure liquid chromatograph was an AKTAExplorer 100 instrument (Amersham Pharmacia Biotech Inc., Umeå, Sweden) operated with dual P-901 pumps, a UV-900 absorption monitor with a 2 mm (3 µl) flow cell and a fraction collector (Frac-901). The system was controlled by Unicorn software (version 3.00). Separations were achieved at ambient temperature with a 3 ml (6.4×100 mm) reversed phase column packed with 15 µm polystyrene/divinyl benzene beads (Resource 15 RPC, Amersham Pharmacia Biotech). The mobile phase delivered at a flow rate of 3 ml/minute consisted of (A) 0.035% (10 mM) ammonium hydroxide (prepared by dilution with water of a 100 mM analytical concentrate from J. T. Baker Chemical Co.) and (B) 0.018% ammonium hydroxide plus 50% acetonitrile (prepared by dilution of eluent A with an equal volume of acetonitrile). The initial conditions were 90% A and 10% B (5% acetonitrile) for 5 minutes. A linear gradient was applied by increasing the acetonitrile to 25% over 13.3 minutes (13.3 column volumes). Another shallower gradient to 35% acetonitrile was applied during the next 35 minutes. Thereafter, a 50% acetonitrile concentration was achieved during 7 minutes and maintained for 5 minutes before recycling to the initial conditions.

Samples for RPC were dissolved in 80% methanol (typically at a concentration of 15 mg/ml), filtered and about 0.225 ml (3.5 mg) was directed with a peristaltic pump (model P-910) to a sample loop (0.5 ml) and the column. Fractions (1 ml) were collected, combined as appropriate and bubbled with nitrogen gas before transferring to preweighed tubes for Savant evaporation at 43° C. These conditions were employed for purification of peptides and saponins.

Ion Exchange Chromatography.

Both anion exchange chromatography (AIEX) and cation exchange chromatography (CIEX) were performed with the AKTAExplorer 100 instrument described above for RPC, utilizing in addition a conductivity flowcell (2 mm, 3 µl) and monitor (pH/C-900, Amersham Pharmacia Biotech).

Peptide Sequencing Experiments.

Samples (50 µg) of the peptides, purified by RPC, were dissolved in 40 µl of 100 mM Tris HCl buffer (pH 8.5) containing 60 mM dithiothreitol (Sigma) as reducing agent. The mixture was heated at 45° C. for 1 hour. Iodoacetamide (in 5 µl Tris) was added to a final concentration of 190 mM and the mixture was heated in the dark at 37° C. for 1 hour. The reaction was quenched by addition of dithiothreitol (150 mM) followed by heating at 37° C. for 1 hour. The mixture was acidified with 2.5% trifluoroacetic acid (TFA) (50 µl). Sample cleanup and concentration were performed on the acidified solution, using 10 µl portions for each pipette tip containing C18 silica (ZipTip C18, Millipore Corp.). The ZipTip procedures followed those of the manufacturer, using a final elution solvent of 0.1% TFA in 50% acetonitrile (101 per ZipTip). The solvent from six ZipTips was combined (60 µl), evaporated with nitrogen (N-Evap) and the residue was redissolved in 20 µl of an appropriate buffer (see footnotes of Tables 14-18). At 100% recovery from the reduction, alkylation and ZipTip procedures, the peptide concentration was approximately 1.5 µg/µl (415 picomoles/µl). For incubation, 3 µl (4.5 µg) was transferred to a 0.6 ml microcentrifuge tube (Rose Scientific, Edmonton, AB).

Solutions of the various peptidases were prepared at appropriate concentrations in the same buffer as the peptide sample and 2 µl were delivered to the microcentrifuge tube to initiate the reactions (5 µl total volume). Incubations at room temperature were conducted with different enzyme to substrate ratios (1:1 to 1:500, depending on the peptidase), with incubation times typically ranging from 0.5-120 minutes. Control tubes with substrate plus buffer (enzyme-depleted) and enzyme plus buffer (substrate-depleted) were included for comparisons.

At a specified incubation time, a portion (0.5 µl) of the incubate was transferred to the MALDI plate and the reaction was quenched with a solution (0.5 µl) of the matrix (α-cyano-4-hydroxycinnamic acid at 5 mg/ml in 75% acetonitrile containing 0.1% TFA). In experiments with endoproteinase Asp N in phosphate buffer and in a few experiments with carboxypeptidase A and Y in ammonium citrate buffer, the incubate (0.5 µl) was added to 0.1% TFA (5-10 µl) before desalting by the usual ZipTip procedure, using a final elution mixture of α-cyano-4-hydroxycinnamic acid at 5 mg/ml in 75% acetonitrile containing 0.1% TFA. The desalted mixture (1-2 µl) was transferred to the MALDI plate for analysis.

Example 30

Quantitative Assessments of Synergism of Pea Isolates by Various Triterpenoid Saponins Pea Isolates.

Insecticidal extracts (C8) in powder form were isolated from protein-rich pea flour (Parrheim Foods, Saskatoon, SK) as previously described (U.S. Pat. No. 5,955,082, Bodnaryk et al., 1999). C8 extracts contain several compounds: several soyasaponins, lysolecithins and peptides. Small amounts of dehydrosoyasaponin I, a minor component in pea extracts, was purified from samples of the C8 powder by flash and reversed phase chromatography, as described in Example 9. A mixture of insecticidal pea peptides of the pea albumin (PA1b) type was obtained from C8 extracts by anion exchange chromatography (Q Sepharose, Amersham Biosciences) followed by ultrafiltration (YM3 membrane, Millipore Corp.). This pea peptide mixture, referred to here as AIEX, was free of soyasaponin and phospholipid components found in C8 extracts. An additional crude extract (unoxidized C8 extract) for comparative testing was obtained from field peas as described (Taylor et al., 2004c). C8 extracts were shown by HPLC to contain primarily PA1b-like peptides with the methionine residues oxidized to methionine sulfoxide, whereas unoxidized C8 extracts were enriched in PA1b variants with methionine residues in the natural (unoxidized) state (Taylor et al., 2004c).

Other Chemicals.

Soyasaponin I (free acid) was isolated from soybean meal and purified to 85-95% purity by methods described in Taylor et al., (2004a). Echinocystic acid 3-glucoside and hederacoside C of HPLC grade were purchased from Apin Chemicals Limited (Abingdon, Oxon, U.K.), whereas α-hederin was obtained from Indofine Chemical Company Inc. (Hillsborough, N.J., U.S.A.). β-escin (90-95%) and the monoammonium salt of glycyrrhizic acid (~75%) were purchased from Sigma-Aldrich Canada Limited (Oakville, ON, Canada). Comparative studies were conducted with commercially available detergents, namely Tween 20 and liquid dish soap. Tween 20 is polyoxyethylene(20)sorbitan monolaurate (a non-ionic surfactant), and the dish soap brand was Sunlight.

Bioassays.

Antifeedant activity was assessed with a flour disk bioassay (Xie et al., 1996) with 70% ethanol as solvent Twenty-five adult *S. oryzae* (1-2 weeks old) were held on five wheat flour disks for 3 days at 30° C., 70% relative humidity. Flour disks (ca. 0.1 g/disk) were weighed before and after exposure to the insects. After weighing the disks, insects and flour disks were returned to the Petri dishes, and the mortality noted each day, until the insects had been on the disks for a total of 14 days. Antifeedant activity was determined by expressing consumption of treated disks as a percentage of control disks (70% ethanol). Positive controls using the same C8 extract were run with each bioassay.

Data Analysis.

The amount of compound required to reduce feeding by 50 and 900% of control insects and their confidence limits was estimated in a manner similar to Sokal & Rohlf (1969), but considering $Y_o$ as a population mean rather than a single observation. The estimate and confidence limits are the values of X where the line $Y=Y_o$ crosses the regression line and its upper and lower confidence curves, respectively. The formulae can be expressed in terms of outputs from the regression analysis. Let a and b be the estimates of the intercept and slope, MSE the mean square error, n the number of observations, t the (2-sided) critical value of t with n−2 degrees of freedom, V(b) the variance (standard error squared) of b and $D=b^2-t^2V(b)$). Then the estimate of X is $X_o=(Y_o-a)/b$ and the confidence limits for X are $X_0+t^2V(b)(Y_0-\bar{Y})/bD\pm H$ where $H^2=t^2[D\cdot MSE/n+V(b)(Y_0-\bar{Y})^2]/D^2$. The interval is not symmetric about $X_o$.

Probit analysis (Polo-PC, LeOra Software, Berkeley, Calif., U.S.A.) was used to estimate the concentrations required to kill 50 and 90% of the population after seven days. For the experiments that used a single dose, the mean survival time was estimated using Kaplan-Meier survival analysis (SigmaStat 3.0, SPSS Inc, Chicago, Ill., U.S.A.). The co-toxicity coefficient was calculated using equations from Sun & Johnson (1960). To estimate the $EC_{50}$ for feeding reduction and the $LD_{50}$ the following concentrations were used (by weight in flour): C8; 0.016, 0.048, 0.096, 0.192, 0.4, 0.8, 1.6 and 3.2%; AIEX and β-escin; 0.024, 0.048, 0.096, 0.192, 0.4, 0.8 and 1.6%; soysaponin I; 0.48, 0.096, 0.192, 0.4, 0.8, 1.6, 3.2, 6.4 and 12.8% (Tables 2 and 4 had additional concentration 25.6%), mixtures of soyasaponin I and C8; 0.016, 0.048, 0.096, 0.192, 0.4, 0.8 and 1.6%; mixtures of β-escin with C8, β-escin with AIEX peptides and soysaponin I with AIEX peptides; 0.008, 0.024, 0.048, 0.096, 0.192, 0.04 and 0.8%.

The protein sources, AIEX or C8, mixed in the diet without additional saponins, reduced feeding of *S. oryzae* to between 32 and 55% (Table 21). Although the feeding bioassays were not replicated, the positive controls using C8 run with each bioassay over the interval that bioassays were conducted, causing a mean feeding reduction of 25% (N=17), standard deviation of 11%, minimum of 9.8%, maximum of 43% and 95% confidence interval of 5.6%. With the AIEX or C8 in the food, the mean survival time was reduced to approximately 7 days, whereas there was no mortality in the controls. For the saponins; hederacoside C, glycyrrhizic acid and soyasaponin I, used alone there was no significant reduction in feeding, and with soyasaponin I there was no increase in mortality compared to the controls. The other saponins tested reduced feeding. Adding 10% AIEX or C8 to the non-toxic saponins reduced feeding and survival. The mixtures of dehydrosoyasaponin I and AIEX, soyasaponin I and C8 as well as β-escin and C8 were slightly more effective than the either of the two compounds used alone. Neither Tween or dish soap were toxic to the rice weevil. Unlike soyasaponin I, dehydrosoyasaponin I and β-escin, the mixture of soap and C8 was not better than the C8 used alone.

In order to better estimate the differences between the mixtures, experiments were conducted at a range of concentrations for each mixture (Tables 22-25). Concentrations of approximately 0.1% of C8 or 0.5% of AIEX, without the added saponins, reduced feeding by 50% (Table 22). As seen in other Examples, soyasaponin I used alone did not significantly reduce feeding. At the highest concentration tested, 12.8%, feeding was reduced to 75% of the control. The mixture of soyasaponin I (90%) and purified peptides (10%) had a similar reduction in feeding as the purified peptides used alone. Similar trends to those seen with the feeding were seen with the mortality (Table 23). AIEX or C8 at 0.4% killed half the population after seven days. Soyasaponin I caused no mortality.

Some of the mixtures tested were highly synergistic. ↑-escin was as toxic as the peptide sources (Table 25). However, when β-escin was mixed with C8, the mixture caused more feeding reduction and was more toxic than either of d-escin or C8 alone. Similar trends were seen with the β-escin-AIEX mixtures. Most of the mixtures of saponins and peptides were considered to be synergistic, having a co-toxicity coefficient greater than 120 (Table 26).

Example 31

Alcohol Extraction of Insecticidal Components from Non-Defatted Pea Flour

C8 extracts from field peas provide an interesting mixture of insecticidal natural products. The extraction processes described in this Example were aimed at producing a crude pea extract with lowered costs than the process described in U.S. Pat. No. 5,955,082 (Bodnaryk et al, 1999). The development of these extraction processes was aided by identification of the insecticidally-active components and synergists of pea extracts and development of specific analytical techniques for their detection as described in other examples, such as Examples 29 and 30.

According to U.S. Pat. No. 5,955,082, the protein-rich pea flour is first defatted with chloroform. In the present work it was found that the defatting step could be avoided completely. With the simplified procedure, the insect bioassays could not demonstrate any benefits from defatting so this step and the filtration step that followed could be circumvented.

Additionally, it was important to establish a suitable solvent to solid ratio because U.S. Pat. No. 5,955,082 specifies a high ratio (25:1) contributing to additional solvent costs. The present work establishes that a 10:1 (ml:g) solvent to solid ratio gave crude extracts that were as active as those from 25:1 experiments.

During investigations on the isolation, purification and identification of the insecticidal components from field peas, purified samples of the soyasaponins, peptides and lysolecithins were found to be soluble in aqueous alcohol mixtures, for example mixtures containing >60% methanol (or ethanol). In fact, hundreds of active samples were readily dissolved in 80% methanol for chromatographic analyses.

The simplified extraction process of the present invention is exemplified using solvent mixtures of 80% methanol or 80% ethanol, conducted with non-defatted protein-enriched pea flour in a magnetically-stirred vessel (Erlenmeyer flask) at room temperature (22-24° C.) at seven timed intervals (0.5, 1, 2, 4, 8, 16 and 24 hours) and under reflux (72-78° C. for 5 minutes, 0.5 and 3 hours). Experiments at room temperature were performed with a low (110:1) and high (25:1) solvent to flour ratio (ml:g). In addition, crude extracts were obtained with chloroform-defatted pea flour using hot 80% methanol (5 min reflux) and a 25:1 solvent to flour ratio, which was the preferred extraction procedure (prior to cleanup with a C8 silica cartridge) reported by U.S. Pat. No. 5,955,082 (Bodnaryk et al., 1999). For comparison, chloroform-defatted flour was also extracted with hot 80% ethanol (25:1 ratio, 5 min reflux). Three samples of C8 extracts (in powder form) were tested for comparison.

The concentration of active ingredients in pea flour would be expected to vary, depending on the pea variety, field location, year of growth and other factors. Since the source of pea flour was from a commercial mill (Parrheim Foods, Saskatoon), most of these genetic and environmental factors were not known. It was also possible that a mill effect could further complicate the distribution of natural products in a flour obtained by air fractionation. To compensate for these factors, the extraction experiments were performed on flour that had been milled in 2001 and in 2003. About 2.5 kilograms of pooled flour samples were prepared and stored in a closed container at room temperature. Extractions were performed during 2003 on 100 gram subsamples of the pea flour.

After extraction, the mixture was filtered and the off-white insoluble cake (a potentially valuable by-product) was washed with methanol. The brown alcoholic filtrate was transferred to a round bottom flask and evaporated to dryness by rotary evaporation (bath temp $\leq$35° C.). After most of the solvent had been removed, small portions of methanol (or ethanol) were added to the semisolid or liquid contained in the evaporation flask. Continued rotary evaporation (bath temp $\leq$ 50° C.) gave a semi-solid or solid material which was dried under vacuum in a desiccator. A light to dark brown insecticidal powder was removed from the evaporation flask with a spatula and weighed. Starting with 100 grains of protein-rich flour, the yield of insecticidal powder, equivalent to the extractable material weight (EMW), varied from 10-20% (10-20 grams) depending on conditions. The nonextractable material (representing 80-90% of the starting flour mass) could easily be recovered during the filtration step. It did not exhibit significant insecticidal activity.

After evaporation and drying, the crude insecticidal powders isolated from pea flours were studied by the following techniques: (1) HPLC under acidic conditions with a conventional C18 silica column, an evaporative light scattering detector and an internal standard (alpha-hederin) to obtain peak areas of insecticidal peptides (sum of peak areas from partially resolved mixtures) and soyasaponins (well resolved peaks for soyasaponins I and VI), expressed as peak area ratio of total peptides to internal standard and total saponins (soyasaponin I plus soyasaponin VI) to internal standard; (2) LC-MS under basic conditions with a modified C18 column attached to an electrospray ionization mass spectrometer to confirm the occurrence of the major insecticidal peptides; (3) bioassays with the rice weevil, assessing antifeedant activity (food consumption) of each powder and $EC_{50}/LC_{50}$ determinations on selected extracts.

Extraction times were considered to be optimized when the HPLC peak area ratios of total peptides and total saponins were at or very close to their maximum values. Although insecticidal dehydrosoyasaponin I could be detected in low concentrations by mass spectrometry, its concentrations were too low for detection by HPLC and therefore it did not contribute to the total saponin values.

The data in Tables 27 and 28 show, among other things, that:

(1) the defatting step with chloroform can be avoided completely.
(2) a solvent to flour ratio of 10:1 (ml:g) can be substituted for a 25:1 ratio, thereby significantly reducing solvent consumption.
(3) the optimum time of extraction at room temperature (22-24° C.) is 16 hours with 80% methanol, 2 hours with 80% ethanol.
(4) at room temperature, 80% methanol (16 h) gives a peptide to soyasaponin ratio of 1.5:1 whereas this ratio with 80% ethanol (2 h) is 0.5:1. These ratios did not show a year effect and both are well within the range for synergism.
(5) at room temperature, the yield of total extractable material is greater with 80% methanol (15%) than with 80% ethanol (10%). Excess solvent (2.5 liters/100 g flour) increases the yield by an additional 34%.
(6) under hot reflux conditions (5-30 min) with a solvent to flour ratio of 10:1 (ml:g), 80% ethanol (16% total extractable material) and 80% methanol (18% total extractable material) are excellent solvents for extraction of insecticidal peptides whereas saponin levels are similar to levels observed in extracts obtained at room temperature.
(7) peptide to soyasaponin ratios ranged from 2.7-5.1:1 in experiments with refluxing ethanol and from 2.2-4.7:1 with refluxing methanol (5 and 30 minutes). With defatted pea flour, the type of flour used to produce C8 extracts, these ratios tended to be higher, especially with methanol as solvent in 2003 (9.6:1).
(8) extended periods of reflux (3 hours) with both methanol and ethanol gave extracts of greatly reduced peptide content and of low insecticidal activity.
(9) all extracts examined by mass spectrometry contained small but detectable quantities of insecticidal dehydrosoyasaponin I. Lysolecithins, which enhance the activity of dehydrosoyasaponin I, were detected by thin layer chromatography. Peak areas from HPLC showed that soyasaponins I and VI were the major saponins observed in the extracts.
(10) relative concentrations of soyasaponins I and VI, estimated by comparison of HPLC peak areas to those of the internal standard, were variable, without any specific trend being apparent. Soyasaponin VI is unstable in solution (Hu et al., 2002) and is known to be converted to soyasaponin I (and maltol). This variability may be related to the duration of rotary evaporation (to obtain the extract in powder form). However, soyasaponin VI was usually the major saponin component in products from extractions at room temperature and under reflux.
(11) apart from the variability in soyasaponins I and VI ratios, the sum of HPLC peak areas for these saponins was stable and seldom showed significant differences among the various treatments.

The technology described here is an improvement to the extraction technology described in U.S. Pat. No. 5,955,082 (Bodnaryk et al., 1999). Furthermore, at room temperature, 80% ethanol showed remarkable selectivity for the extraction of oxidized peptides (3752, 3757, 3805 Da) with both the high and low solvent to flour ratios. Methanol (80%) and hot ethanol (80%) were shown to extract both the oxidized and unoxidized (3736, 3741, 3789 Da) peptides. Therefore, temperature-controlled experiments with ethanol will provide opportunities for selectively extracting the oxidized peptides in quantity for certain applications.

Example 32

Precipitation of Insecticidal Components with an Organic Acid

Crude extracts (1 g) from field peas, obtained after extraction of the 2003 milled flour for 5 min with hot 80% ethanol, were magnetically stirred with 1 M or 3 M acetic acid (50 ml) for 20 min at room temperature (about 22-24° C.). After centrifugation at 4000 rpm for 20 min, the supernatant was decanted and the yellow sludge that remained was centrifuged again. Residual acetic acid was removed with a pipette. In some experiments, the precipitate was additionally washed with 1 M or 0.1 M acetic acid (2×10 ml), centrifuging and decanting as before. The precipitate that remained was dissolved with vortex mixing in 80% methanol (50 ml). After centrifugation (4000 rpm for 20 min), the solution was rotary evaporated under reduced pressure at $\leq 40°$ C. and then Savant evaporated to dryness at 43° C. A brown powder or oil was obtained in yields of 8-20% (from the crude isolate, see Table 29). In a 1 M acetic acid precipitation experiment with 2003 flour extracted for 5 min with hot 80% methanol, the yield of precipitate (unwashed) was 28% (a brown viscous oil).

These experiments demonstrated that crude pea extracts could be further purified without incurring the costs of a chromatographic purification step. The precipitates, especially those derived from 1 M acetic acid treatment of crude ethanol extracts, demonstrated good activity. The activity was predictable because not only insecticidal peptides but also synergistic soyasaponins (and lysolecithins) precipitated from solution, as judged by HPLC and HPLC/MS analyses. It was also significant that the precipitate contained peptides of the methionine sulfoxide type, namely those generated during mill processing of pea flour (masses of 3805, 3757 and 3752 Da). Thus, this acid precipitation process appears to be readily applicable to extracts derived from legume plant material.

Example 33

Insecticidal Isolates from Lentils

Mature seeds of lentils (*Lens culnaris*, var. *Eston*), obtained from the Crop Development Centre, University of Saskatchewan in Saskatoon, were ground with a Wiley mill equipped with a 40 mesh screen. With a procedure from Bodnaryk et al. (1999), the lentil flour (100 g) after defatting with chloroform was extracted with refluxing 80% methanol for 5 minutes, filtered and the filtrate was concentrated by rotary evaporation (bath temperature <40° C.) until 25% methanol remained. The concentrated solution was diluted with water (200 ml) and was partially purified by stirring for 24 h with water-washed Diaion™ HP 20 beads (particle size 250-600 µM; porosity 300-600D) from a 180 ml cartridge (Biotage Inc., Charlottesville, Va.). After collecting the beads by filtration, the beads were washed with 30% methanol (500 ml). This wash was discarded. The beads were re-washed with 100% methanol (500 ml). The methanol was removed by rotary evaporation and the residue remaining in the flask transferred to a test tube. Evaporation was completed at 43° C. with a centrifugal evaporator (model SC 110A Savant SpeedVac Plus) and the brown powder that remained, designated as an HP-20 MeOH fraction, was dried under vacuum in a desiccator (470 mg, 0.47% yield) before testing and analysis. At a dose of 1.6 mg/200 mg flour, this crude extract was active against the rice weevil, giving a food consumption value of 32.6% and a mean survival time of 7.0 days.

Analysis by HPLC/MS (electrospray ionization) and by HPLC with an evaporative light scattering detector showed several features in lentil extracts (HP-20 MeOH fraction) that were common to the C8 extracts of peas. This included the detection of a PA1b-related peptide (3881 Da, 9.8% of the mixture), soyasaponin I (942 Da, 25.8%) and soyasaponin VI (1068 Da, 22.0%). Lentils also contained a glycoside of the flavonoid kaempferol (902 Da, 42.4%), which was isolated by flash chromatography and shown to be inactive in the rice weevil bioassay (food consumption of 101.2% at 1.6 mg/200 mg flour). Following anion exchange experiments with Q Sepharose (pH of 10.5) and ultrafiltration of the flowthrough fraction with a YM3 membrane (see example 13), the 3881 peptide of lentils was isolated. Peptides of this mass have not previously been reported from lentils. A purified sample of this new peptide was shown to be active against the rice weevil, giving a food consumption value of 42.4% and a mean survival time of 7.0 days. After reduction with dithiothreitol and alkylation with iodoacetamide, MALDI mass spectrometry (see Example 29) showed a prominent molecular ion at m/z 4229, indicative of six cysteine residues (3 disulfide bonds) from a gain of 348 mass units. This indicated that the insecticidal peptide of lentils was closely related to the insecticidal PA1b peptides of peas. Recent literature (Louis et al., 2004) indicates that soybean (*Glycine max*) and French bean (*Phaseolus vulgaris*) also contain insect-toxic peptides related to pea albumins. Insecticidal activity of the peptide from lentils (and other legume seeds in addition to peas) might also be enhanced by the presence of soyasaponin I.

Tables 1 through 29 referred to throughout the Examples are consecutively presented as follows:

TABLE 1

Fractionation of a blank sample and a C8 mixture (130 mg) by column chromatography with silica gel and antifeedant activity of resulting fractions.

| eluent composition | | | isolated fractions | | | |
|---|---|---|---|---|---|---|
| | | | blank[1] | | C8 | |
| chloroform (%) | methanol (%) | volume (ml) | weight (mg) | f.c.[2] (%) | weight (mg) | f.c.[2] (%) |
| 100 | 0 | 75 | <1 | 123 | 18 | 99 |
| 98 | 2 | 75 | <2 | 109 | 2 | 100 |
| 95 | 5 | 75 | <2 | 104 | 2 | 76 |
| 90 | 10 | 75 | <1 | 94 | 4 | 56 |
| 80 | 20 | 75 | 1 | 106 | 3 | 119 |
| 60 | 40 | 75 | <1 | 106 | 8 | 113 |
| 40 | 60 | 75 | <2 | 116 | 12 | 15[3] |
| 20 | 80 | 75 | <1 | 117 | 12 | 45 |
| 0 | 100 | 75 | <1 | 117 | 6 | 42 |
| 0 | 100 | 75 | 1 | 110 | 5 | 36 |
| 0 | 100 | 250 | 2 | 101 | 6 | 24[3] |
| 0 | 100 | 250 | 1 | 106 | 3 | 42 |

[1]Chromatography was performed without the C8 sample.
[2]Food consumption in the rice weevil antifeedant bioassay, expressed as % of control.
[3]Dose-response experiments were performed on these active fractions, designated C8-1a and C8-1b respectively (see FIG. 2).

TABLE 2

Fractionation of C8 material (250 mg) by flash chromatography with a Biotage silica cartridge (90 grams) and solvent system 1.

| fraction | $R_f^1$ | weight | f.c.[2] | relative polarity |
|---|---|---|---|---|
| 1 | >0.5 | 65 mg | 109 | low |
| 2 (C8-2a) | 0.25-0.5 | 48 mg | 39 | intermediate |
| 3 | <0.25 | 7 mg | 71 | high |
| 4 (C8-2b)[3] | <0.25 | 28 mg | 52 | high |

[1] With silica gel TLC plates and solvent system 1. Detection techniques are discussed in the text.
[2] Food consumption, expressed as % of control. Experimental samples were tested in the rice weevil antifeedant bioassay at a concentration of 1.6 mg/200 mg flour (1.2 mg for fraction 3).
[3] This end fraction was obtained by elution with methanol (250 ml).

TABLE 3

Comparison of activity in the rice weevil antifeedant bioassay of soyasaponin mixtures and purified soyasaponin 1 obtained from defatted soybean meal.

| sample description[1] | purification methods[1] | food consumption (% of control)[2] |
|---|---|---|
| crude mix (sodium salts) | pilot plant isolate | 91 |
| crude mix (free acids) | (b) | 93 |
| soyasaponin mix (free acids) | (a) and (b) | 92 |
| soyasaponin I (free acid)[3] | (a), (c), (b) and (d) | 83 |
| soyasaponin I (free acid)[3,4] | (a), (c), (b) and (d) | 114 |

[1] See FIG. 4.
[2] The dose was 1.6 mg/200 mg flour.
[3] The purity was 95% by HPLC.
[4] A replicate of the sample in entry 4, isolated by repeating the four purification steps.

TABLE 4

Fractionation of cold methanol extracted and freeze dried material (130 mg) by flash chromatography with a Biotage silica cartridge (9 g) and solvent system 1.

| | | | soyasaponins[1] | | |
|---|---|---|---|---|---|
| fraction | elution volume | weight | I | VI | f.c.[2] |
| 1 | 0-42 ml | 32 mg | − | − | 99 |
| 2 | 43-57 ml | 8 mg | − | − | 112 |
| 3 | 58-72 ml | 9 mg | − | − | 111 |
| 4 | 73-87 ml | 9 mg | + | + | 78 |
| 5 | 88-102 ml | 7 mg | +[3] | +[3] | 55 |
| 6 | 103-500 ml | 9 mg[4] | + | + | 28 |
| maltol | | | | | 110 |

[1] The presence (+) or absence (−) of saponins as shown by TLC and HPLC.
[2] Food consumption, expressed as % of control, in the rice weevil antifeedant bioassay. Experimental samples were tested at a concentration of 1.6 mg/200 mg of flour.
[3] Also detected by HPLC/MS.
[4] This sample contained primarily ninhydrin-positive components by TLC.

TABLE 5

HPLC and electrospray ionization mass spectral data on identified components of active fraction C8-2a (fraction 2 of Table 2).

| retention time (min) | relative peak areas[1] (%) | quasimolecular ion[2] (m/z of MH$^+$) | designated structure in FIG. 5 |
|---|---|---|---|
| 17.9 | 93.2 | 943 | S-I |
| 19.4 | 1.7 | 941 | D-I |
| 19.4 | [3] | 1069 | S-VI |
| 24.1 | 1.6 | 520 | L-18:2 |
| 25.9 | 1.0 | 496 | L-16:0 |
| 26.5 | 2.5 | 522 | L-18:1 |

[1] Obtained by integration of HPLC peaks from a representative evaporative light scattering detector chromatogram (see FIG. 3B) by (peak area of indicated component/sum of peak areas × 100).
[2] These are mass-to-charge (m/z) values for protonated molecular ions found in the corresponding peaks of the total ion chromatogram during HPLC/MS analysis.
[3] Compounds D-I and S-VI coeluted during conditions used for HPLC so the area of these two components represented 1.7% of the mixture. During HPLC/MS, the leading edge of this peak showed predominantly the ion at m/z 941 whereas the trailing edge showed predominantly the m/z 1069 ion.

TABLE 6

Fractionation of extract C8-2a by liquid chromatography with MCI gel.

| | | | soyasaponins[1] | | lysolecithins[1] | | | |
|---|---|---|---|---|---|---|---|---|
| fraction | elution solvent (volume) | weight | S-I | D-1 | L-18:2 | L-16:0 | L-18:1 | f.c.[2] |
| 1 | 80-90% methanol (100 ml) | 4.2 mg | + | − | − | − | − | 82 |
| 2 | methanol (0-35 ml) | 8.2 mg | + | − | + | + | ± | 85 |
| 3 | methanol (36-70 ml) | 13.7 mg | + | +[3] | + | + | − | 35 |
| 4 | methanol (71-125 ml) | 7.6 mg | − | +[4] | + | + | + | 45 |

[1] The indicated compounds were detected (+), were probably detected at trace concentrations (±) or were undetectable (−) as determined by TLC and HPLC.
[2] Food consumption, expressed as % of control, in the rice weevil antifeedant bioassay. Experimental samples were tested at a concentration of 1.6 mg/200 mg of flour.
[3] D-1 (but not S-VI) was detected by HPLC/MS. The major component was S-1 (see FIG. 6).
[4] Although D-1 was the only saponin detected, the major components were lysolecithins.

TABLE 7

Prominent daughter ions observed during collision-induced dissociation (CID) experiments on purified samples of soyasaponin I (S-I) and dehydrosoyasaponin I (D-I).[1]

| sample | MH$^+$ | (M-rha + H)$^+$ | (M-rha-gal + H)$^+$ | (M-rha-gal-H$_2$O + H)$^+$ | (M-rha-gal-2H$_2$O + H)$^+$ | (aglycone[2] + H)$^+$ | (aglycone-OH)$^+$ | (aglycone-OH—H$_2$O)$^+$ |
|---|---|---|---|---|---|---|---|---|
| S-I[3] | 943 (100) | 797 (35) | 635 (20) | 617 (15) | 599 (20) | 459 (5) | 441 (55) | 423 (30) |
| D-I | 941 (100) | 795 (25) | 633 (15) | 615 (5) | 597 (15) | 457 (5) | 439 (40) | 421 (10) |

[1] The collision energy was set at 30 eV. Numbers shown are m/z values, with the relative intensities of the ions in brackets.
[2] The aglycone of S-I is soyasapogenol B (molecular weight of 458). The aglycone of D-I is soyasapogenol E (molecular weight of 456). See also FIG. 5.
[3] The indicated fragmentation pathways for S-I have been published (Lee et al., 1999).

TABLE 8

Fractionation of C8 (150 mg) by flash chromatography with a Biotage silica cartridge (8 g) and solvent system 2.

| fraction | weight | ninhydrin-positive TLC spot of R$_F$ 0.50[1] | 0.35[2] | 0.28[3] | soyasaponins | lysolecithins | f.c.[4] |
|---|---|---|---|---|---|---|---|
| 1 | 13 mg | −[5] | − | − | − | − | 76 |
| 2 | 36 mg | +[5] | + | + | + | + | 14 |
| 3[6] | 37 mg | ±[5] | + | + | ± | − | 24 |
| 4[6] | 7 mg | ± | + | + | − | − | 16 |
| 5 | 6 mg | ± | ± | + | − | − | 38 |
| C8[7] | | + | + | + | + | + | 19 |

[1] The HPLC retention time was 14.4 minutes.
[2] The HPLC retention time was 15.4 minutes.
[3] The HPLC retention time was 14.9 minutes.
[4] Food consumption, expressed as % of control, in the rice weevil antifeedant bioassay. Each fraction was tested at a concentration of 1.6 mg/200 mg of flour.
[5] The indicated compounds were detected (+), were probably detected in trace concentrations (±) or were undetectable (−) as determined by TLC (solvent system 2) and HPLC.
[6] These fractions are considered as the system 2 peptide isolate.
[7] The same batch of C8 powder used for fractionation.

TABLE 9

Antifeedant properties of peptide fractions isolated by ion exchange chromatography.

| sample | ninhydrin-positive TLC spot of R$_F$ 0.50[1] | 0.35[1] | 0.28[1] | soyasaponins | lysolecithins | f.c.[2] |
|---|---|---|---|---|---|---|
| AIEX YM3 | +[3] | ±[3] | + | −[3] | − | 31 |
| AIEX YM1 | + | ± | + | − | − | 31 |
| AIEX NaCl | ± | ± | ± | + | + | 77[4] |
| AIEX NaCl YM3 | ± | ± | + | ± | + | 35 |
| AIEX NaCl NaOH[5] | + | + | + | + | + | 13 |
| AIEX NaCl NaOH[6] | + | + | + | + | − | 21 |
| CIEX fraction 1 | − | − | − | − | − | 70 |
| CIEX fraction 2 | + | − | + | − | − | 33 |
| CIEX fraction 3 | ± | ± | + | − | − | 41 |
| C8[7] | + | + | + | + | + | 24 |

[1] With silica gel plates and solvent system 2.
[2] Food consumption, expressed as % of control, in the rice weevil antifeedant bioassay. The experimental samples were tested at a concentration of 1.6 mg/200 mg of flour.
[3] The indicated compounds were detected (+), were probably detected in trace concentrations (±) or were undetectable (−) as determined by TLC (solvent systems 1 and 2) and HPLC.
[4] A freeze-dried sample (methanol-soluble portion) contaminated with salt. Higher doses of 7.4 mg, 14.7 mg and 29.5 mg (per 200 mg of flour) gave f.c. values of 58%, 39% and 32% respectively.
[5] A freeze-dried sample (methanol-soluble portion) was treated with 25 mM sodium hydroxide in methanol.
[6] A freeze-dried sample (methanol-soluble portion) was treated with 250 mM sodium hydroxide in methanol.
[7] From the same batch of C8 powder used for anion exchange chromatography.

TABLE 10

Quasimolecular ions of isolated peptides and of their S-carbamidomethyl derivatives found during electrospray ionization mass spectrometry.[1]

| sample | m/z of MH$^+$ (native peptides) | | | | | | | | | | |
|---|---|---|---|---|---|---|---|---|---|---|---|
| | 3732 | 3737[2] | 3742[2] | 3753 | 3758 | 3789[3] | 3790 | 3806 | 3842 | 3858 | 3942[2] | 3958 |
| C8 | +[4] | + | + | + | + | + | + | + | + | + | −[4] | + |
| sys. 1 isolate | + | ±[4] | − | − | ± | + | − | ± | ± | + | − | − |
| sys. 2 isolate | − | + | + | + | + | ± | + | + | − | + | − | ± |
| AIEX YM3 | ± | + | + | + | + | + | + | + | + | + | ± | ± |
| AIEX NaCl[5] | − | − | − | ± | + | ± | + | ± | + | ± | ± | ± |
| CIEX fr. 1 | − | − | − | ± | ± | ± | ± | ± | − | − | − | − |
| CIEX fr. 2 | ± | − | ± | − | + | − | + | − | − | − | − | − |
| CIEX fr. 3 | − | ± | − | + | ± | + | + | ± | ± | − | − | ± |

TABLE 10-continued

Quasimolecular ions of isolated peptides and of their S-carbamidomethyl derivatives found during electrospray ionization mass spectrometry.[1]

| derivatized sample | m/z of MH⁺ (S-carbamidomethyl derivatives)[6] | | | | | | | | | | | |
|---|---|---|---|---|---|---|---|---|---|---|---|---|
| | 4080 | 4085 | 4090 | 4101 | 4105 | 4137 | 4138 | 4154 | 4190 | 4205 | 4290 | 4305 |
| C8 | + | + | − | + | + | + | + | + | − | + | − | + |
| AIEX YM3 | + | + | + | + | + | + | + | + | ± | + | − | + |
| CIEX fr. 2 | − | − | + | − | + | − | + | + | − | + | − | − |
| CIEX fr. 3 | + | + | − | + | ± | + | + | − | − | − | − | ± |

[1]Samples were analyzed by HPLC/MS without complete separation of the various peptides or their derivatives.
[2]Peptides of these masses were reported to occur in the albumin fraction of peas grown in France (Delobel et al., 1999).
[3]A peptide (pea albumin 1b or PA1b) of this mass was first described by Higgins et al. (1986) although average molecular mass (reported as 3742) was incorrectly calculated. From their reported 37 amino acid sequence of PA1b, the calculated average mass is 3788.4 (MH⁺ of 3789 expected under our reported HPLC/MS conditions) and the calculated exact mass is 3785.7. High resolution MALDI/MS on the system 1 isolate gave a quasimolecular ion at 3786.7, which corresponded precisely to the calculated exact mass of 3785.7.
[4]The indicated peptides and their derivatives were detected (+), were probably present in trace concentrations (±) or were undetectable (−) by searching for the appropriate quasimolecular ions following HPLC/MS. Peptides that showed prominent quasimolecular ions during HPLC/MS were also detected by MALDI/MS.
[5]This sample had been treated with 25 mM sodium hydroxide (see footnote 5 of Table 9).
[6]These derivatives corresponded in molecular mass to the alkylation of six cysteine residues with iodoacetamide (addition of 348 mass units).

TABLE 11

Some chemical features of pea albumin (PA1) described by Higgins et al. (1986).[1]

| | leader[2] | PA1b | spacer | PA1a | carboxyl end |
|---|---|---|---|---|---|
| chain length | 26 | 37 | 5 | 53 | 8 |
| number of cysteines | 0 | 6 | 0 | 4 | 0 |
| variant possibilities | 0 | 3456[3] | 0 | 2 | 0 |
| molecular mass | 2696 | 3618-4023 | 634 | 5927-6018 | 817 |

[1]According to Higgins et al. (1986), PA1 is first synthesized as a preprotein (molecular weight ≈ 13,900) consisting of a leader sequence (≈2,700) at the amino terminal end and a proprotein (≈11,200) which contains the sequences of both PA1a (≈6,000) and PA1b (≈3,800).
[2]The leader sequence, which has the characteristics of a signal sequence of proteins destined for transmembrane transport, consists of a nine and seventeen amino acid peptide linked by an intron (in the gene sequence). The leader sequence is presumably removed co-translationally and the proprotein is thought to be cleaved post-translationally (endoproteolytically) to yield two polypeptides which, after removal of some carboxyl-terminal amino acids, represent the mature forms of PA1a and PA1b.
[3]Determined in the present work.

TABLE 12

Peak area distribution (%) determined by XTerra HPLC of ten pea peptides found in experimental samples.[1]

| sample[2] | 3752[3] | 3757 | 3736 | 3857 | 3805 | 3741 | 3841 | 3789 | 3731 | 3788 |
|---|---|---|---|---|---|---|---|---|---|---|
| system 1 isolate | 9.8 | 7.3 | 6.9[4] | | 11.0 | 1.1[5] | | 8.5 | 55.3[6] | |
| system 2 isolate | 18.7 | 18.8 | 12.5 | | 25.5 | 10.7[5] | | 13.7 | 0.2[6] | |
| AIEX YM3 | 24.9 | 18.9 | 15.3 | | 16.3 | 7.6 | 1.2 | 5.3 | 2.1 | 8.3 |
| AIEX YM1 | 25.5 | 22.1 | 14.6 | | 21.7 | 6.3 | 1.1 | 5.9 | 0.1 | 2.6 |
| AIEX NaCl YM3 | 10.9 | 22.7 | 3.2 | | 52.5 | 2.2[5] | | 3.2 | 0.3[6] | |
| AIEX NaCl NaOH[7] | 6.6 | 18.9 | 7.6 | | 57.1 | 2.3[5] | | 5.8 | 1.6[6] | |
| CIEX fraction 2 | 6.9 | 47.6 | — | | 37.9 | 5.8[5] | | 1.5 | 0.2[6] | |
| CIEX fraction 3 | 68.5 | 2.6 | 9.5 | | 5.0 | 0.8[5] | | 2.2 | 11.4[6] | |
| C8[8] | 22.4 | 29.5 | 8.6 | | 24.0 | 5.7 | 0.4 | 5.4 | 1.0 | 3.0 |
| C8[8] | 21.8 | 28.6 | 9.0 | | 23.3 | 6.3 | 0.4 | 6.4 | 1.1 | 3.1 |
| C8[8] | 24.7 | 25.8 | 7.0 | | 28.1 | 4.3 | 0.5 | 5.8 | 0.7 | 2.9 |

[1]At 210 nm. Peak area distribution was calculated by (peak area of indicated peptide/sum of the peptide peak areas × 100).
[2]See Table 9 and FIG. 15.
[3]The peptides are listed in order of their elution from the column. Assignments were confirmed in most cases by electrospray HPLC/MS with an XTerra column (see FIG. 17).
[4]Peak areas obtained for this data column represent an unresolved mixture of the 3736 and 3857 peptides. These peptides remained unseparated on a 3.5 or 5 μm particle size HPLC column.
[5]These peak areas represent a mixture of the 3741 and 3841 peptides (5 μm particles).
[6]These peak areas represent a mixture of the 3731 and 3788 peptides (5 μm particles).
[7]This sample had been treated with 25 mM sodium hydroxide (see footnote 5 of Table 9).
[8]These extracts were obtained from different commercial batches of air classified pea flour.

TABLE 13

Quasimolecular ions of four purified peptide samples found during MALDI mass spectrometry and sequence variant possibilities derived from the pea albumin1b model of Higgins et al.

| sample designate[1] (average mass) | m/z[2] of MH+ (monoisotopic) | molecular mass[3] (monoisotopic) | PA1b (M) | variants[4] (m) |
|---|---|---|---|---|
| 3752 | 3750.5 | 3749.5 | 10 | 35 |
| 3757[5] | 3755.6 | 3754.6 | 10 | 7 |
| 3805[6] | 3803.6 | 3802.6 | 4 | 14 |
| 3788[7,8] | 3786.7 | 3785.7 | 30 | —[9] |

[1]The peptides are listed in order of their elution during RPC and correspond to molecular masses derived from electrospray ionization data (see table 10, top). These average masses were confirmed by MALDI experiments (low resolution, linear mode). The 3788 peptide corresponded in molecular weight to PA1b of Higgins et al. (1986).
[2]These measurements were determined with the use of ACTH fragment 7-38 (monoisotopic mass of 3656.9) and bovine insulin (monoisotopic mass of 5729.6) as calibrants for the MALDI mass spectrometer (reflection mode). Accuracy of the peptide masses was estimated at ±0.2 units. Monoisotopic masses of these peptides were about 2.8 mass units less than average masses
[3]Masses that matched these values were calculated with the aid of a computer batch file and spreadsheet (Microsoft Excel ™) as described for the 3788 peptide (Taylor et al., 2001).
[4]Values in these columns represented the number of variants (isoforms) that were found in the spreadsheet calculations to have identical or very similar masses (within ±0.2 mass units) to those determined by reflection MALDI mass spectrometry, considering either methionine (M) or methionine sulfoxide (m) as a possible residue at position 12.
[5]Another source (AIEX NaCl YM3, FIG. 15) of the 3757 peptide gave an MH+ of 3755.5.
[6]Another source (AIEX NaCl YM3, FIG. 15) of the 3805 peptide gave an MH+ of 3803.4.
[7]The 3788 peptide isolated from a different sample of the system 1 isolate (FIG. 15) gave an MH+ of 3786.8.
[8]An unstable peptide of average mass 3789 (MH+ 3787.6 Da) was also isolated. This is believed to be identical to the 3805 peptide but containing M rather than m at position 12.
[9]Variant possibilities are irrelevant because the 3788 peptide had isoleucine at position 12.

TABLE 14

C-terminal fragments detected by MALDI mass spectrometry on reduced and alkylated peptide 3788.

| amino acid | average mass | CPA[1] | CPP[2] | CPY[3] | CPP[4] | PRO[5] | PRO[6] |
|---|---|---|---|---|---|---|---|
|  | 4136.9 | +[7] | + | + | + | + | + |
| -G | 4079.8 | + | + | + | + | + | + |
| -Y | 3916.6 | + |  | + | + |  | + |
| -P | 3819.5 |  |  |  | + |  |  |
| -N | 3705.4 | + |  |  |  | + | + |
| -R | 3549.2 |  |  |  | + |  |  |
| -C | 3389.0 | + | + |  |  | + | + |
| -K | 3260.9 |  | + |  | + |  |  |
| -G | 3203.8 |  | + |  |  |  |  |
| -I | 3090.6 |  |  |  | + |  |  |
| -V | 2991.5 | + |  |  |  |  |  |
| -L | 2878.4 | + |  |  |  | + | + |
| -G | 2821.3 | + | + |  |  | + | + |
| -V | 2722.2 |  |  | + | + |  |  |
| -P | 2625.1 |  |  |  |  |  |  |
| -I | 2511.9 |  |  | + |  |  |  |
| -C | 2351.7 | + |  |  | + | + | + |
| -R | 2195.5 |  |  |  |  |  |  |
| -C | 2035.3 |  |  |  |  |  |  |
| -L | 1922.2 |  |  | + |  |  |  |
| -P | 1825.0 |  |  |  |  |  |  |
| -S | 1738.0 |  |  |  |  |  |  |
| -G | 1690.9 |  |  |  |  |  |  |
| -C | 1520.7 |  |  |  |  |  |  |
| -P | 1423.6 |  |  |  |  |  |  |
| -P | 1326.5 |  |  |  |  |  |  |
| -I | 1213.3 |  |  |  |  |  |  |
| -D | 1098.2 |  |  |  |  |  |  |
| -F | 951.0 |  |  |  |  |  |  |
| -P | 853.9 |  |  |  |  |  |  |
| -S | 766.9 |  |  |  |  |  |  |
| -C | 606.7 |  |  |  |  |  |  |
| -V | 507.5 |  |  |  |  |  |  |
| -G | 450.5 |  |  |  |  |  |  |
| -N | 336.4 |  |  |  |  |  |  |
| -C | 176.2 |  |  |  |  |  |  |
| -S | 89.1[8] |  |  |  |  |  |  |

[1]Carboxypeptidase A (purchased as an aqueous suspension from Sigma-Aldrich Canada Limited, Oakville, Ontario) in 25 mM ammonium citrate (pH 6) and incubated for 10-360 minutes at room temperature with an enzyme to substrate ratio of 1:10 (by weight). After 360 minutes, a portion (0.5 μl) of the incubate was desalted with a C18 Zip-Tip before mass spectral analysis.
[2]Carboxypeptidase P (Roche Diagnostics, Laval, Quebec) in 25 mM ammonium citrate (pH 6) and incubated for 10-120 minutes at room temperature with an enzyme to substrate ratio of 1:10 (by weight).
[3]Carboxypeptidase Y (Sigma) in 25 mM ammonium citrate (pH 6) and incubated for 10-120 minutes at room temperature with an enzyme to substrate ratio of 1:10 (by weight).
[4]Carboxypeptidase P (Roche) in 25 mM ammonium citrate (pH 4) and incubated for 10-120 minutes at room temperature with an enzyme to substrate ratio of 1:10 (by weight).
[5]Pronase containing 20% calcium acetate (Roche) in 25 mM ammonium bicarbonate buffer (pH 8) and incubated for 0.25-10 minutes at room temperature with an enzyme to substrate ratio of 1:500 (by weight).
[6]Pronase containing 20% calcium acetate (Roche) in 25 mM ammonium citrate buffer (pH 4) and incubated for 0.25-10 minutes at room temperature with an enzyme to substrate ratio of 1:10 (by weight).
[7]The + indicates that a M + 1 ion corresponding to the indicated mass was detected during linear MALDI analysis.
[8]This mass corresponded to the average molecular weight of alanine, the N-terminal amino acid of this peptide (see FIG. 18).

TABLE 15

N-terminal fragments detected by MALDI mass spectrometry on reduced and alkylated peptide 3788.

| amino acid | average mass | APM[1] | APM[2] | PRO[3] | PRO[4] | ASP[5] |
|---|---|---|---|---|---|---|
|  | 4136.9 | +[6] | + | + | + |  |
| -A | 4065.8 | + |  | + | + |  |
| -S | 3978.7 |  |  | + |  |  |
| -C | 3818.5 |  |  |  |  |  |
| -N | 3704.4 |  |  |  |  |  |
| -G | 3647.4 |  |  |  | + |  |
| -V | 3548.2 |  |  |  |  |  |
| -C | 3388.0 | + | + |  |  |  |
| -S | 3300.9 |  |  |  |  |  |
| -P | 3203.8 |  |  |  |  |  |
| -F | 3056.7 |  |  |  | + | + |
| -D | 2941.6 |  |  |  |  |  |
| -I | 2828.4 |  |  |  |  |  |
| -P | 2731.3 |  |  |  |  |  |
| -P | 2634.2 |  |  |  |  |  |
| -C | 2474.0 |  |  |  |  |  |
| -G | 2416.9 | + | + |  |  |  |
| -S | 2329.8 |  |  |  |  |  |
| -P | 2232.7 |  |  | + |  |  |
| -L | 2119.6 |  |  | + | + |  |
| -C | 1959.4 | + |  |  |  |  |
| -R | 1803.2 | + |  | + | + |  |
| -C | 1643.0 | + | + |  |  |  |
| -I | 1529.8 |  |  |  |  |  |
| -P | 1432.7 |  |  |  |  |  |
| -V | 1333.6 |  |  |  |  |  |
| -G | 1276.5 | + |  | + | + |  |
| -L | 1163.7 | + |  |  |  |  |
| -V | 1064.2 | + | + |  |  |  |
| -I | 951.1 | + | + |  |  |  |
| -G | 894.0 |  |  |  | + |  |
| -K | 765.8 | + |  |  |  |  |
| -C | 605.7 |  |  |  |  |  |
| -R | 449.5 |  |  |  |  |  |
| -N | 335.4 |  |  |  |  |  |

TABLE 15-continued

N-terminal fragments detected by MALDI mass spectrometry on reduced and alkylated peptide 3788.

| amino acid | average mass | APM[1] | APM[2] | PRO[3] | PRO[4] | ASP[5] |
|---|---|---|---|---|---|---|
| -P | 238.2 | | | | | |
| -Y | 75.1[7] | | | | | |

[1]Aminopeptidase M (purchased from Roche as a suspension in ammonium sulfate) in 10 mM Tris hydrochloride buffer (pH 7.5) and incubated for 10-120 minutes at room temperature with an enzyme to substrate ratio of 1:1 (by weight).
[2]Aminopeptidase M (Roche) in 25 mM ammonium bicarbonate buffer (pH 8) and incubated for 30-120 minutes at room temperature with an enzyme to substrate ratio of 1:1 (by weight).
[3]Pronase containing 20% calcium acetate (Roche) in 25 mM ammonium bicarbonate buffer (pH 8) and incubated for 0.5-10 minutes at room temperature with an enzyme to substrate ratio of 1:500 (by weight).
[4]Pronase containing 20% calcium acetate (Roche) in 25 mM ammonium citrate buffer (pH 4) and incubated for 0.5-10 minutes at room temperature with an enzyme to substrate ratio of 1:10 (by weight).
[5]Endoproteinase Asp-N (Sigma) in 100 mM sodium phosphate buffer (pH 7.8) and incubated for 120-240 minutes at room temperature with an enzyme to substrate ratio of 1:10 (by weight). A portion (0.5 μl) of the incubate was desalted with a C18 Zip-Tip before mass spectral analysis.
[6]The + indicates that an M + 1 ion corresponding to the indicated mass was detected during linear MALDI analysis.
[7]This mass corresponded to the average molecular weight of glycine, the C-terminal amino acid of this peptide (see FIG. 18).

TABLE 16

N- and C-terminal fragments detected by MALDI mass spectrometry on reduced and alkylated peptide 3757.

| N-terminal amino acid | average mass | APM[1] | PRO[2] | PRO[3] | Glu-C[4] | average mass | C-terminal amino acid |
|---|---|---|---|---|---|---|---|
| | 4105.7 | +[5] | + | + | + | | |
| | | + | + | + | + | 4105.7 | |
| -A | 4034.7 | + | | | | | |
| | | | + | + | + | 4048.7 | -G |
| -S | 3947.6 | + | | | | | |
| | | | | | | 3961.6 | -S |
| -C | 3787.4 | | | | | | |
| | | | | | | 3864.5 | -P |
| -N | 3673.3 | | | | + | | |
| | | | + | + | | 3750.4 | -N |
| -G | 3616.2 | | + | | | | |
| | | | | | | 3594.2 | -R |
| -V | 3517.1 | | | | | | |
| | | | + | + | + | 3434.0 | -C |
| -C | 3356.9 | + | | | | | |
| | | | + | + | + | 3270.8 | -Y |
| -S | 3269.8 | | | | | | |
| | | | | | | 3213.8 | -G |
| -P | 3172.7 | | | | | | |
| | | | | + | | 3100.6 | -I |
| -F | 3025.5 | | | + | | | |
| | | | | | | 3001.5 | -V |
| -E | 2896.4 | | | | + | | |
| | | | + | + | | 2888.3 | -L |
| -m | 2749.2 | + | | + | + | | |
| | | | + | | | 2831.3 | -G |
| -P | 2652.1 | | | | | | |
| | | | + | | | 2732.1 | -V |
| -P | 2555.0 | | | | | | |
| | | | | | | 2635.0 | -P |
| -C | 2394.8 | | | | | | |
| | | | | | | 2521.9 | -I |
| -G | 2337.7 | | | | | | |
| | | | | | | 2361.7 | -C |
| -T | 2236.6 | | | | | | |
| | | | + | | | 2205.5 | -R |
| -S | 2149.5 | | | | + | | |
| | | | | | | 2045.3 | -C |
| -A | 2078.5 | | | | | | |
| | | | + | | | 1974.2 | -A |
| -C | 1918.3 | | | | | | |
| | | | | | | 1887.1 | -S |

TABLE 16-continued

N- and C-terminal fragments detected by MALDI mass spectrometry on reduced and alkylated peptide 3757.

| N-terminal amino acid | average mass | APM[1] | PRO[2] | PRO[3] | Glu-C[4] | average mass | C-terminal amino acid |
|---|---|---|---|---|---|---|---|
| -R | 1762.1 | | + | + | + | | |
| | | | | | | 1786.0 | -T |
| -C | 1601.9 | + | | | | | |
| | | | | | | 1729.0 | -G |
| -I | 1488.7 | | | | | | |
| | | | | | | 1568.8 | -C |
| -P | 1391.6 | | | | | | |
| | | | | | | 1471.7 | -P |
| -V | 1292.5 | | | | | | |
| | | | | | | 1374.5 | -P |
| -G | 1235.4 | | + | | | | |
| | | | | | | 1227.3 | -m |
| -L | 1122.3 | | | | | | |
| | | | | | | 1098.2 | -E |
| -V | 1023.1 | | | + | | | |
| | | | | | | 951.0 | -F |
| -I | 910.0 | | | | | | |
| | | | | | | 853.9 | -P |
| -G | 852.9 | | | | | | |
| | | | | | | 766.9 | -S |
| -Y | 689.7 | | | | | | |
| | | | | | | 606.7 | -C |
| -C | 529.6 | | | | | | |
| | | | | | | 507.5 | -V |
| -R | 373.4 | | | | | | |
| | | | | | | 450.5 | -G |
| -N | 259.3 | | | | | | |
| | | | | | | 336.4 | -N |
| -P | 162.1 | | | | | | |
| | | | | | | 176.2 | -C |
| -S | 75.1[6] | | | | | | |
| | | | | | | 89.1[7] | -S |

[1]Aminopeptidase M (Roche) in 25 mM ammonium bicarbonate buffer (pH 8) and incubated for 5-220 minutes at room temperature with an enzyme to substrate ratio of 1:1 (by weight).
[2]Pronase containing 20% calcium acetate (Roche) in 25 mM ammonium bicarbonate buffer (pH 8) and incubated for 0.5-30 minutes at room temperature with an enzyme to substrate ratio of 1:50 (by weight) and for 0.5-140 minutes with an enzyme to substrate ratio of 1:500 (by weight).
[3]Pronase containing 20% calcium acetate (Roche) in 25 mM ammonium citrate buffer (pH 4) and incubated for 0.5-30 minutes at room temperature with an enzyme to substrate ratio of 1:10 (by weight).
[4]Endoproteinase Glu-C (Sigma, from Staphylococus aureus strain V8) in 100 mM ammonium bicarbonate buffer (pH 7.8) and incubated or 1-6 hours at 37° C. with an enzyme to substrate ratio of 1:20 (by weight).
[5]The + indicates that an M + 1 ion corresponding to the indicated mass was detected during linear MALDI analysis.
[6]This mass corresponded to the average molecular weight of glycine, the C-terminal amino acid of this peptide (see FIG. 19).
[7]This mass corresponded to the average molecular weight of alanine, the N-terminal amino acid.

TABLE 17

N- and C-terminal fragments detected by MALDI mass spectrometry on reduced and alkylated peptide 3805

| N-terminal amino acid | average mass | APM[1] | PRO[2] | PRO[3] | Glu-C[4] | average mass | C-terminal amino acid |
|---|---|---|---|---|---|---|---|
| | 4153.8 | +[5] | + | + | + | | |
| | | + | + | + | + | 4153.8 | |
| -A | 4082.7 | + | | | | | |
| | | | + | + | + | 4096.7 | -G |
| -S | 3995.6 | + | | | | | |
| | | | | | | 4009.6 | -S |
| -C | 3835.4 | | | | | | |
| | | | | | | 3912.5 | -P |
| -N | 3721.3 | | | | + | | |
| | | | | | | 3798.4 | -N |
| -G | 3664.4 | | + | + | | | |

TABLE 17-continued

N- and C-terminal fragments detected by MALDI mass spectrometry on reduced and alkylated peptide 3805

| N-terminal | | | | | | C-terminal | |
|---|---|---|---|---|---|---|---|
| amino acid | average mass | APM[1] | PRO[2] | PRO[3] | Glu-C[4] | average mass | amino acid |
|  |  |  |  |  | + | 3642.2 | -R |
| -V | 3565.1 |  |  |  |  |  |  |
|  |  |  |  | + | + | 3482.0 | -C |
| -C | 3404.9 | + |  |  |  |  |  |
|  |  |  | + | + | + | 3318.9 | -Y |
| -S | 3317.9 | + |  |  |  |  |  |
|  |  |  |  |  |  | 3261.8 | -G |
| -P | 3220.7 |  |  |  |  |  |  |
|  |  |  | + | + | + | 3148.7 | -I |
| -F | 3073.6 |  |  | + |  |  |  |
|  |  |  | + | + | + | 3001.5 | -F |
| -E | 2944.5 |  |  |  | + |  |  |
|  |  |  | + | + | + | 2888.3 | -L |
| -m | 2797.3 | + |  | + | + |  |  |
|  |  |  |  |  | + | 2831.3 | -G |
| -P | 2700.1 |  |  |  |  |  |  |
|  |  |  |  | + |  | 2732.1 | -V |
| -P | 2603.0 |  |  |  |  |  |  |
|  |  |  |  |  |  | 2635.0 | -P |
| -C | 2442.8 | + |  |  |  |  |  |
|  |  |  |  |  |  | 2521.9 | -I |
| -G | 2385.8 |  |  |  | + |  |  |
|  |  |  | + | + | + | 2361.7 | -C |
| -T | 2284.7 |  |  |  | + |  |  |
|  |  |  |  | + |  | 2205.5 | -R |
| -S | 2197.6 |  |  |  | + |  |  |
|  |  |  |  |  |  | 2045.3 | -C |
| -A | 2126.5 |  |  |  | + |  |  |
|  |  |  |  |  |  | 1974.2 | -A |
| -C | 1966.3 |  |  |  | + |  |  |
|  |  |  |  |  |  | 1887.1 | -S |
| -R | 1810.1 |  | + | + | + |  |  |
|  |  |  |  |  |  | 1786.0 | -T |
| -C | 1649.9 | + |  |  |  |  |  |
|  |  |  |  |  |  | 1729.0 | -G |
| -I | 1536.8 |  |  |  |  |  |  |
|  |  |  |  |  |  | 1568.7 | -C |
| -P | 1439.7 |  |  |  |  |  |  |
|  |  |  |  |  | + | 1471.7 | -P |
| -V | 1340.5 |  |  |  | + |  |  |
|  |  |  |  |  | + | 1374.5 | -P |
| -G | 1283.5 |  | + | + | + |  |  |
|  |  |  |  |  | + | 1227.3 | -m |
| -L | 1170.3 | + | + | + | + |  |  |
|  |  |  |  |  | + | 1098.2 | -E |
| -F | 1023.1 | + | + | + |  |  |  |
|  |  |  |  |  |  | 951.0 | -F |
| -I | 910.0 |  |  |  |  |  |  |
|  |  |  |  |  |  | 853.9 | -P |
| -G | 852.9 |  |  |  |  |  |  |
|  |  |  |  |  |  | 766.9 | -S |
| -Y | 689.7 |  |  |  |  |  |  |
|  |  |  |  |  |  | 606.7 | -C |
| -C | 529.6 |  |  |  |  |  |  |
|  |  |  |  |  |  | 507.5 | -V |
| -R | 373.4 |  |  |  |  |  |  |
|  |  |  |  |  |  | 450.5 | -G |
| -N | 259.3 |  |  |  |  |  |  |
|  |  |  |  |  |  | 336.4 | -N |
| -P | 162.1 |  |  |  |  |  |  |
|  |  |  |  |  |  | 176.2 | -C |

TABLE 17-continued

N- and C-terminal fragments detected by MALDI mass spectrometry on reduced and alkylated peptide 3805

| N-terminal | | | | | | C-terminal | |
|---|---|---|---|---|---|---|---|
| amino acid | average mass | APM[1] | PRO[2] | PRO[3] | Glu-C[4] | average mass | amino acid |
| -S | 75.1[6] |  |  |  |  |  |  |
|  |  |  |  |  |  | 89.1[7] | -S |

[1]Aminopeptidase M (Roche) in 25 mM ammonium bicarbonate buffer (pH 8) and incubated for 5-60 minutes at room temperature with an enzyme to substrate ratio of 1:1 (by weight).
[2]Pronase containing 20% calcium acetate (Roche) in 25 mM ammonium bicarbonate buffer (pH 8) and incubated for 0.5-30 minutes at room temperature with an enzyme to substrate ratio of 1:50 (by weight) and for 0.5-10 minutes with an enzyme to substrate ratio of 1:500 (by weight).
[3]Pronase containing 20% calcium acetate (Roche) in 25 mM ammonium citrate buffer (pH 4) and incubated for 0.5-60 minutes at room temperature with an enzyme to substrate ratio of 1:10 (by weight).
[4]Endoproteinase Glu-C (Sigma, from *Staphylococus aureus* strain V8) in 100 mM ammonium bicarbonate buffer (pH 7.8) and incubated for 10 minutes to 9 hours at 37° C. with an enzyme to substrate ratio of 1:20 (by weight).
[5]The + indicates that an M + 1 ion corresponding to the indicated mass was detected during linear MALDI analysis.
[6]This mass corresponded to the average molecular weight of glycine, the C-terminal amino acid of this peptide (see FIG. 20).
[7]This mass corresponded to the average molecular weight of alanine, the N-terminal amino acid.

TABLE 18

N- and C-terminal fragments detected by MALDI mass spectrometry on reduced and alkylated peptide 3752.

| N-terminal | | | | | | C-terminal | |
|---|---|---|---|---|---|---|---|
| amino acid | average mass | APM[1] | PRO[2] | PRO[3] | Glu-C[4] | average mass | amino acid |
|  | 4100.7 | +[5] | + | + | + |  |  |
|  |  | + | + | + | + | 4100.7 |  |
| -A | 4029.6 | + |  |  |  |  |  |
|  |  |  |  | + | + | 4043.7 | -G |
| -S | 3942.6 | + |  |  |  |  |  |
|  |  |  |  |  |  | 3956.6 | -S |
| -C | 3782.4 |  |  |  |  |  |  |
|  |  |  |  |  |  | 3859.5 | -P |
| -N | 3668.3 |  |  | + | + |  |  |
|  |  |  |  |  |  | 3722.4 | -H |
| -G | 3611.2 |  |  | + | + |  |  |
|  |  |  |  |  | + | 3566.1 | -R |
| -V | 3512.1 |  |  |  |  |  |  |
|  |  |  |  | + | + | 3406.0 | -C |
| -C | 3351.9 | + |  |  |  |  |  |
|  |  |  |  | + | + | 3242.8 | -Y |
| -S | 3264.8 |  |  |  |  |  |  |
|  |  |  |  |  |  | 3185.7 | -G |
| -P | 3167.7 |  |  |  |  |  |  |
|  |  |  |  | + |  | 3086.6 | -V |
| -F | 3020.5 |  |  | + |  |  |  |
|  |  |  |  |  | + | 2987.5 | -V |
| -E | 2891.4 |  |  |  | + |  |  |
|  |  |  |  | + | + | 2874.3 | -L |
| -m | 2744.2 | + |  | + | + |  |  |
|  |  |  |  |  | + | 2817.2 | -G |
| -P | 2647.1 |  |  |  |  |  |  |
|  |  |  |  | + |  | 2718.1 | -V |
| -P | 2550.0 |  |  |  | + |  |  |
|  |  |  |  |  |  | 2621.0 | -P |
| -C | 2389.8 |  |  |  |  |  |  |
|  |  |  |  |  |  | 2507.8 | -I |
| -G | 2332.7 |  |  |  |  |  |  |
|  |  |  |  | + | + | 2347.6 | -C |
| -S | 2245.6 |  |  |  | + |  |  |
|  |  |  |  |  |  | 2191.5 | -R |
| -S | 2158.6 |  |  |  | + |  |  |
|  |  |  |  |  |  | 2031.3 | -C |
| -A | 2087.5 |  |  |  |  |  |  |
|  |  |  |  |  |  | 1960.2 | -A |
| -C | 1927.3 |  |  |  |  |  |  |

TABLE 18-continued

N- and C-terminal fragments detected by MALDI mass spectrometry on reduced and alkylated peptide 3752.

| N-terminal | | | | | | C-terminal | |
|---|---|---|---|---|---|---|---|
| amino acid | average mass | peptidase | | | | average mass | amino acid |
| | | APM[1] | PRO[2] | PRO[3] | Glu-C[4] | | |
| -R | 1771.1 | | + | + | + | | |
| | | | | | | 1786.0 | -S |
| -C | 1610.9 | + | | | | | |
| | | | | | | 1729.0 | -G |
| -I | 1497.7 | | | | | | |
| | | | | | | 1568.8 | -C |
| -P | 1400.6 | | | | | | |
| | | | | | | 1471.7 | -P |
| -V | 1301.5 | | | | | | |
| | | | | | | 1374.5 | -P |
| -G | 1244.4 | | + | + | | | |
| | | | | | | 1227.4 | -m |
| -L | 1131.3 | + | | | + | | |
| | | | | | + | 1098.2 | -E |
| -V | 1032.1 | | | | | | |
| | | | | | | 951.0 | -F |
| -V | 933.0 | | | | | | |
| | | | | | | 853.9 | -P |
| -G | 876.0 | | + | | | | |
| | | | | | | 766.9 | -S |
| -Y | 712.8 | | | | | | |
| | | | | | | 606.7 | -C |
| -C | 552.6 | | | | | | |
| | | | | | | 507.5 | -V |
| -R | 396.4 | | | | | | |
| | | | | | | 450.5 | -G |
| -H | 259.3 | | | | | | |
| | | | | | | 336.4 | -N |
| -P | 162.1 | | | | | | |
| | | | | | | 176.2 | -C |
| -S | 75.1[6] | | | | | | |
| | | | | | | 89.1[7] | -S |

[1]Aminopeptidase M (Roche) in 25 mM ammonium bicarbonate buffer (pH 8) and incubated for 5-120 minutes at room temperature with an enzyme to substrate ratio of 1:1 (by weight).
[2]Pronase containing 20% calcium acetate (Roche) in 25 mM ammonium bicarbonate buffer (pH 8) and incubated for 0.5-30 minutes at room temperature with an enzyme to substrate ratio of 1:50 (by weight) and for 0.5-120 minutes with an enzyme to substrate ratio of 1:500 (by weight).
[3]Pronase containing 20% calcium acetate (Roche) in 25 mM ammonium citrate buffer (pH 4) and incubated for 0.5-30 minutes at room temperature with an enzyme to substrate ratio of 1:10 (by weight). See FIG. 22 for the mass spectrum from a 10 minute incubate.
[4]Endoproteinase Glu-C (Sigma, from Staphylococus aureus strain V8) in 100 mM ammonium bicarbonate buffer (pH 7.8) and incubated for 1-9 hours at 37° C. with an enzyme to substrate ratio of 1:20 (by weight).
[5]The + indicates that an M + 1 ion corresponding to the indicated mass was detected during linear MALDI analysis.
[6]This mass corresponded to the average molecular weight of glycine, the C-terminal amino acid of this peptide (see FIG. 21).
[7]This mass corresponded to the average molecular weight of alanine, the N-terminal amino acid.

TABLE 19

Probable interrelationships of peptides detected in C8 extracts containing methionine (M) and methionine sulfoxide (m) and their HPLC properties.[1]

| M containing | | | m containing | | |
|---|---|---|---|---|---|
| molecular weight (Da) | retention time (min) | relative peak area (%) | molecular weight (Da) | retention time (min) | relative peak area (%) |
| 3736[2] | 22.7 | 4.3[3] | 3752 | 17.9 | 22.4 |
| 3741 | 28.9 | 5.7 | 3757 | 22.0 | 29.5 |
| 3789 | 31.6 | 5.4 | 3805 | 23.9 | 24.0 |
| 3841[2] | 29.8 | 0.4 | 3857 | 22.7 | 4.3[3] |
| 3941[2,4] | | <0.1 | 3957[4] | | <0.1 |

[1]XTerra HPLC (see Table 12). The 3731 (1.1%) and 3788 (3.2%) peptides did not contain methionine or methionine sulfoxide.
[2]Peptides of these masses were reported to occur in the albumin fraction of peas grown in France (Delobel et al., 1999).
[3]Since these peptides coeluted during HPLC (see FIG. 17), the peak areas were assumed to be equal.
[4]These peptides were not detected with certainty during XTerra HPLC and XTerra HPLC/MS (also see Table 10).

TABLE 20

Antifeedant properties against rice weevils of additional triterpenoid saponins and potentially synergistic mixtures of pea peptides and these saponins.[1]

| Saponin | initial treatment[3] | peptide to saponin treatment ratios[2] | | |
|---|---|---|---|---|
| | | 9:1 | 1:1 | 1:9 |
| Dehydrosoyasaponin I (D-I) | 65 | 32 (17) | 34 | —[4] |
| Echinocyatic acid 3-glucoside | 41 | 40 | 39 | 48 |
| β-Escin | 18[5] | 17 (14) | 17 (15) | 18 (16) |
| Glycyrrhizic acid | 96 | 33 | 45 | 39 |
| Hederacoside C | 117 | 44 | 47 | 58 |
| α-Hederin | 36 | 24 | 26 | 26 |
| Soyasaponin I (S-I)[6] | 98 | 24 (29) (44)[7] | 23 (27) (33)[7] | 16 (26) (42)[7] |

[1]Antifeedant activity in terms of food consumption, expressed as % of control.
[2]The source of peptide was AIEX YM3, representing the flowthrough (unretained) fraction obtained-from C8 extracts by anion exchange chromatography with Q-Sepharose. Values in brackets were obtained with C8 material representing the peptide source. The total dose (peptide or C8 plus saponin) was 1.6 mg/200 mg of flour. Experiments with D-I utilized a total dose of 0.8 mg/100 mg of flour.
[3]The dose was 1.6 mg of the indicated saponin/200 mg of flour, except for D-I (0.64 mg/100 mg of flour, equivalent to 1.28 mg/200 mg of flour). Food consumption with an experimental sample of soyasaponin VI was 80%.
[4]D-I was not tested at this ratio.
[5]Food consumption was 30% in a separate experiment.
[6]For comparison. See Table 3 and FIGS. 25-26
[7]Results from a separate experiment, using a different batch of C8 material.

TABLE 21

The effect of mixing saponins and insecticidal pea peptides on the feeding and survival of *Sitophilus oryzae*.

| Saponin or soap Source | Peptide source | Feeding as a percent of control (%)[a] Saponin:peptide ratio | | | | | Mean survival time (days ± SE)[b] Saponin:peptide ratio | | | | |
|---|---|---|---|---|---|---|---|---|---|---|---|
| | | 1:0 | 9:1 | 1:1 | 1:9 | 0:1 | 1:0 | 9:1 | 1:1 | 1:9 | 0:1 |
| Dehydrosoyasaponin I[c] | AIEX | 65 | — | 34 | 32 | 50 | 13.8 ± 0.2 a | — | 5.4 ± 0.3 c | 5.3 ± 0.2 c | 7.5 ± 0.5 b |
| Soyasaponin I | AIEX | 98 | 16 | 23 | 24 | 55 | | | | | |
| Soyasaponin I | C8 | 92 | 20 | 19 | 24 | 49 | 13.8 a | 5.7 ± 0.3 bc | 6.1 ± 0.4 bc | 5.0 ± 0.3 c | 6.7 ± 0.5 b |
| Hederacoside C | AIEX | 117 | 59 | 47 | 45 | 50 | 13.9 a | 8.7 ± 0.5 b | 7.6 ± 0.4 b | 7.6 ± 0.4 b | 7.5 ± 0.5 b |
| Glycyrrhizic acid | AIEX | 96 | 39 | 45 | 33 | 32 | | | | | |
| Echinocystic acid 3-glucoside | AIEX | 41 | 48 | 39 | 40 | 50 | 13.4 ± 0.3 a | 8.3 ± 0.5 b | 7.2 ± 0.5 b | 6.7 ± 0.4 b | 7.5 ± 0.5 b |
| α-hederin | AIEX | 36 | 26 | 26 | 24 | 32 | | | | | |
| β-escin | AIEX | 18 | 18 | 17 | 17 | 32 | | | | | |
| β-escin | C8 | 30 | 16 | 16 | 14 | 49 | 6.3 ± 0.2 a | 4.8 ± 0.3 b | 4.1 ± 0.2 c | 5.1 ± 0.2 b | 7.6 ± 0.5 a |
| Tween | C8[d] | 106 | | 52 | | 17 | 13.7 a | | 8.1 ± 0.5 b | | 6.9 ± 0.4 b |
| Dish soap | C8 | 104 | | 53 | | 17 | >14 a | | 8.5 ± 0.6 b | | 6.9 ± 0.4 b |

[a]Food consumption, expressed as % of control, in the rice weevil bioassay. Concentration of single compounds or total of mixture was 0.8%.
[b]Kaplan-Meier survival analysis was used to estimate mean survival, Holm-Sidak method was used for the multiple comparison, P = 0.05. Within a given row, means followed by different letters are significantly different. There was no mortality in the controls.
[c]Instead of 0.8% used in other tests, only 0.6% was used in this test because of the limited quantity of sample that was available.
[d]In a separate test, C8 at 0.4% had a feeding rate of 62% and mean survival time of 7.1 ± 0.4 days.

TABLE 22

The effective concentration (EC %) to reduce feeding by 50 or 90% of *Sitophilus oryzae* adults held for three days on wafers treated with different concentrations of compounds based on the concentration the combined weight of the compounds or on the weight of either the C8 or the peptide.

| Saponin Source | Peptide source | Variable | Saponin:peptide ratio | | | | |
|---|---|---|---|---|---|---|---|
| | | | 1:0 | 9:1 | 1:1 | 1:9 | 0:1 |
| Soyasaponin I | AIEX oxidized | $EC_{50}$ (%) | >12 | 0.19 | — | — | 0.51 |
| | | 95% CI (%) | — | 0.12-0.35 | — | — | 0.34-0.84 |
| | | $EC_{90}$ (%) | >>12 | 2 | — | — | 79 |
| | | 95% CI (%) | — | 1-9 | — | — | 22- |
| Soyasaponin I | C8 oxidized | $EC_{50}$ (%) | 81 | 0.24 | 0.12 | 0.18 | 0.12 |
| | | 95% CI (%) | 16- | 0.15-0.43 | 0.05-0.25 | 0.10-0.29 | 0.08-0.16 |
| | | $EC_{90}$ (%) | — | 1.4 | 1.3 | 3.4 | 2.9 |
| | | 95% CI (%) | — | 0.71-4.6 | 0.50-8.5 | 1.5-16 | 1.6-6.0 |
| Soyasaponin I | C8 unoxidized | $EC_{50}$ (%) | 27 | 0.32 | 0.13 | 0.12 | 0.13 |
| | | 95% CI (%) | 11- | 0.20-5.1 | 0.08-0.20 | 0.09-0.17 | 0.09-0.18 |
| | | $EC_{90}$ (%) | — | 2.1 | 2.1 | 4.1 | 15 |
| | | 95% CI (%) | — | 1.1-6.5 | 1.1-6.3 | 2.4-9.2 | 7.2-39 |

TABLE 23

The lethal dose for 50 and 90% of the population of the *Sitophilus oryzae* adults held for three days on wafers treated with different concentrations of compounds at 7 days.

| Saponin Source | Peptide source | Variable | Saponin:peptide ratio | | | | |
|---|---|---|---|---|---|---|---|
| | | | 1:0 | 9:1 | 1:1 | 1:9 | 0:1 |
| Soyasaponin I | AIEX oxidized | $LD_{50}$ (%) | >12[a] | 03.35 | — | — | 0.36 |
| | | 95% CI (%) | — | 0.25-0.46[b] | — | — | 0.24-0.55 |
| | | $LD_{90}$ (%) | >>12 | 0.64 | — | — | 3.85 |
| | | 95% CI (%) | — | 0.44-1.12[b] | — | — | 1.84-14 |
| | | Chi2 | — | 12.8 | — | — | 3.7 |
| | | Slope | — | 5.9 | — | — | 1.2 |
| | | Slope SE | — | 1.0 | — | — | 0.2 |
| Soyasaponin I | C8 oxidized | $LD_{50}$ (%) | 47 | 0.26 | 0.09 | 0.17 | 0.05 |
| | | 95% CI (%) | 18- | 0.15-0.43 | 0.04-0.15 | 0.10-0.26 | 0.03-0.08 |
| | | $LD_{90}$ (%) | — | 0.75 | 0.44 | 1.2 | 0.24 |
| | | 95% CI (%) | — | 0.45-2.5 | 0.24-1.5 | 0.65-4.2 | 0.14-0.68 |
| | | Chi2 | 5.8 | 11.5 | 8.7 | 5.3 | 8.9 |
| | | Slope | 1.3 | 2.8 | 1.8 | 1.5 | 1.9 |
| | | Slope SE | 0.4 | 0.4 | 0.2 | 0.2 | 0.3 |
| Soyasaponin I | C8 unoxidized | $LD_{50}$ (%) | 30 | 0.25 | 0.19 | 0.13 | 0.21 |
| | | 95% CI (%) | 15- | 0.15-0.44 | 0.10-0.32 | 0.20-0.17 | 0.12-0.33 |
| | | $LD_{90}$ (%) | — | 0.60 | 0.65 | 0.63 | 1.3 |

TABLE 23-continued

The lethal dose for 50 and 90% of the population of the *Sitophilus oryzae* adults held for three days on wafers treated with different concentrations of compounds at 7 days.

| Saponin Source | Peptide source | Variable | Saponin:peptide ratio | | | | |
|---|---|---|---|---|---|---|---|
| | | | 1:0 | 9:1 | 1:1 | 1:9 | 0:1 |
| | | 95% CI (%) | — | 0.37-2.3 | 0.36-2.7 | 0.43-1.1 | 0.72-3.7 |
| | | Chi2 | 2.4 | 14.7 | 13.1 | 0.9 | 8.9 |
| | | Slope | 1.6 | 3.5 | 2.3 | 1.9 | 1.6 |
| | | Slope SE | 0.5 | 0.5 | 0.3 | 0.2 | 0.2 |

TABLE 24

The effective concentration (EC %) to reduce feeding by 50 or 90% of *Sitophilus oryzae* adults held for three days on wafers treated with different concentrations of compounds based on the concentration of the combined weight of the compounds or on the weight of either the C8 or the peptide.

| Saponin Source | Peptide source | Variable | Saponin:peptide ratio | | | | |
|---|---|---|---|---|---|---|---|
| | | | 1:0 | 9:1 | 1:1 | 1:9 | 0:1 |
| β-escin | C8 oxidized | $EC_{50}$ (%) | 0.19 | 0.08 | 0.08 | 0.10 | 0.12 |
| | | 95% CI (%) | 0.15-0.25 | 0.04-0.12 | 0.05-0.15 | 0.06-0.16 | 0.04-0.28 |
| | | $EC_{90}$ (%) | 1.5 | 1.5 | 0.51 | 1.5 | 21 |
| | | 95% CI (%) | 1-3 | 0.5-6 | 0.35-2.9 | 0.7-8 | 5- |
| β-escin | AIEX oxidized | $EC_{50}$ (%) | 0.19 | 0.08 | — | — | 0.51 |
| | | 95% CI (%) | 0.15-0.25 | 0.04-0.13 | — | — | 0.34-0.84 |
| | | $EC_{90}$ (%) | 1.5 | 1 | — | — | 79 |
| | | 95% CI (%) | 1-3 | 0.5-4 | — | — | 22- |

TABLE 25

The lethal dose for 50 and 90% of the population of the *Sitophilus oryzae* adults held for three days on wafers treated with different concentrations of compounds at 7 days.

| Saponin source | Peptide source | Variable | Saponin:peptide ratio | | | | |
|---|---|---|---|---|---|---|---|
| | | | 1:0 | 9:1 | 1:1 | 1:9 | 0:1 |
| β-escin | C8 oxidized | $LD_{50}$ (%) | 0.45 | 0.20 | 0.13 | 0.19 | 0.47 |
| | | 95% CI (%) | | | 0.11-0.16 | 0.15-0.25 | 0.37-0.60 |
| | | $LD_{90}$ (%) | 1.74 | 0.7 | 0.31 | 0.64 | 1.50 |
| | | 95% CI (%) | | | 0.22-0.47 | 0.45-1.11 | 1.11-2.45 |
| | | Chi2 | 224 | 911 | 4.0 | 3.2 | 5.5 |
| | | Slope | 2.7 | 2.8 | 3.4 | 2.4 | 2.5 |
| | | Slope SE | 0.3 | 0.4 | 0.5 | 0.3 | 0.3 |
| β-escin | AIEX oxidized | $LD_{50}$ (%) | 0.45 | 0.15 | — | — | 0.36 |
| | | 95% CI (%) | | 0.08-0.30 | — | — | 0.24-0.55 |
| | | $LD_{90}$ (%) | 1.74 | 0.36 | — | — | 3.85 |
| | | 95% CI (%) | | 0.20-2.28 | — | — | 1.84-14 |
| | | Chi2 | 224 | 18.8 | — | — | 3.7 |
| | | Slope | 2.7 | 3.4 | — | — | 1.2 |
| | | Slope SE | 0.3 | 0.4 | — | — | 0.2 |

[a] t 12.8% soyasaponin I, the highest concentration tested, there was 4% mortality.
[b] 90% CI used.

TABLE 26

The co-toxicity coefficient for the various mixtures[a], for values above 120, the mixture is considered to work synergistically, between 120 and 80 to be additive, below 80 to be antagonistic.

| Index | Saponin source | Peptide Source | Saponin:peptide ratio 9:1 | 1:1 | 1:9 |
|---|---|---|---|---|---|
| Feeding | Soyasaponin I | C8 oxidized | 493 | 210 | 74 |
|  | Soyasaponin I | C8 unoxidized | 389 | 216 | 120 |
|  | β-escin | C8 oxidized | 346 | — | — |
|  | β-escin | AIEX | 2294 | — | — |
| Mortality | Soyasaponin I | C8 oxidized | 190 | 110 | 33 |
|  | Soyasaponin I | C8 unoxidized | 790 | 219 | 179 |
|  | β-escin | C8 oxidized | 226 | 354 | 246 |
|  | β-escin | AIEX | 293 | — | — |
|  | Soyasaponin I | AIEX | 928 | — | — |

[a]Feeding data from Tables 22 and 24, mortality data from Tables 23 and 25, using $EC_{50}$ $LD_{50}$ values respectively. For the calculation of the mixture of soyasaponin I and AIEX peptide, an $EC_{50}$ of 27% and $LD_{50}$ of 30% were used for soyasaponin I.

TABLE 27

Properties of crude extracts obtained by extraction of commercial pea flour from 2001 and 2003 with 80% methanol and 80% ethanol at room temperature (22-24° C.).

| year | solvent/ extraction time (h) | 10:1 solvent to flour ratio peptides to internal standard ratio[a] | Saponins to internal standard ratio[b] | EMW, g/100 g of flour[c] | rice weevil f.c. (%)[d] | $EC_{50}$ (%)[e] | $LC_{50}$ (%)[f] | 25:1 solvent to flour ratio peptides to internal standard ratio[a] | saponins to internal standard ratio[b] | EMW, g/100 g of flour[c] | rice weevil f.c. (%)[d] | $EC_{50}$ (%)[e] | $LC_{50}$ (%)[f] |
|---|---|---|---|---|---|---|---|---|---|---|---|---|---|
| 2001 | MeOH | | | | | | | | | | | | |
|  | 0.5 | 0.09 | 0.16 | 13.2 | 60 | | | | | | | | |
|  | 1.0 | 0.08 | 0.15 | 12.6 | 61 | | | 0.08 | 0.12 | 18.6 | 54 | | |
|  | 2.0 | 0.12 | 0.15 | 14.3 | 56 | | | | | | | | |
|  | 4.0 | 0.18 | 0.16 | 13.4 | 56 | | | 0.07 | 0.13 | 18.6 | 46 | | |
|  | 8.0 | 0.19 | 0.17 | 14.4 | 46 | | | | | | | | |
|  | 16 | 0.22 | 0.16 | 14.9 | 52 | 3.3 | 3.2 | 0.09 | 0.12 | 18.2 | 59 | | |
|  | 24 | 0.17 | 0.12 | 14.5 | 61 | | | | | | | | |
| 2001 | EtOH | | | | | | | | | | | | |
|  | 0.5 | 0.03 | 0.21 | 8.4 | 62 | | | | | | | | |
|  | 1.0 | 0.08 | 0.22 | 10.3 | 54 | | | 0.03 | 0.14 | 13.2 | 69 | | |
|  | 2.0 | 0.12 | 0.24 | 9.9 | 53 | 6.9 | 2.5 | | | | | | |
|  | 4.0 | 0.10 | 0.24 | 10.0 | 58 | | | 0.07 | 0.17 | 13.5 | 60 | | |
|  | 8.0 | 0.10 | 0.21 | 11.1 | 65 | | | | | | | | |
|  | 16 | 0.10 | 0.18 | 11.6 | 57 | | | 0.07 | 0.16 | 13.4 | 63 | | |
|  | 24 | 0.12 | 0.17 | 12.0 | 53 | | | | | | | | |
|  | Reference C8 extract[g] | | | | | | | 16.10 | 0.54 | | 20 | 0.2 | 0.1 |
| 2003 | MeOH | | | | | | | | | | | | |
|  | 0.5 | 0.03 | 0.11 | 13.5 | 85 | | | 0.06 | 0.09 | 18.2 | 58 | | |
|  | 1.0 | 0.05 | 0.08 | 14.7 | 57 | | | 0.06 | 0.08 | 18.0 | 54 | | |
|  | 2.0 | 0.13 | 0.09 | 14.3 | 58 | | | | | | | | |
|  | 4.0 | 0.11 | 0.08 | 15.3 | 54 | | | 0.20 | 0.07 | 19.1 | 58 | | |
|  | 8.0 | 0.13 | 0.12 | 15.1 | 54 | | | | | | | | |
|  | 16 | 0.16 | 0.12 | 16.9 | 59 | 6.6 | 2.2 | 0.09 | 0.08 | 18.3 | 53 | | |
|  | 24 | 0.11 | 0.08 | 14.7 | 60 | | | | | | | | |
| 2003 | EtOH | | | | | | | | | | | | |
|  | 0.5 | 0.07 | 0.16 | 10.4 | 60 | | | | | | | | |
|  | 1.0 | 0.07 | 0.19 | 10.4 | 56 | | | 0.05 | 0.15 | 12.8 | 60 | | |
|  | 2.0 | 0.12 | 0.19 | 11.0 | 53 | inactive | 4.0 | | | | | | |
|  | 4.0 | 0.07 | 0.16 | 9.7 | 57 | | | 0.04 | 0.15 | 12.7 | 63 | | |
|  | 8.0 | 0.09 | 0.20 | 11.4 | 69 | | | | | | | | |
|  | 16 | 0.07 | 0.16 | 11.4 | 63 | | | 0.04 | 0.18 | 13.8 | 61 | | |
|  | 24 | 0.04 | 0.10 | 10.6 | 52 | | | | | | | | |
|  | Reference C8 extract[g] | | | | | | | 17.7 | 0.41 | | 27 | 0.1 | 0.4 |

[a]Ratio determined by C-18 HPLC from integrated peak areas of the peptides (eluting at 14.7-17.2 min) to the internal standard of α-hederin (25.9 min).
[b]Ratio determined by C-18 HPLC from integrated peak areas of soyasaponin I (21.2 min) plus soyasaponin VI (25.2 min) to α-hederin.
[c]Extractable material weight (as a brown or beige solid) from 100 g of pea flour, the amount of flour used in each extraction experiment.
[d]Food consumption in the rice weevil (*Sitophilus oryzae*) antifeedant disk bioassay with 70% ethanol as solvent. Antifeedant activity was assessed by expressing consumption of treated disks (treated at a dose of 1.6 mg per 100 mg of wheat flour) as a percentage of control disks (70% ethanol).
[e]Effective concentration (in mg/100 mg wheat flour) required to reduce feeding to 50% of feeding in the control disks.
[f]Lethal concentration (in mg/100 mg wheat flour) required to kill 50% of the population after exposure of insects to disks for 7 days.
[g]Obtained in powder form from defatted pea flour by hot 80% methanol extraction and C8 SepPak cartridges (Bodnaryk et al., 1999).

TABLE 28

Properties of crude extracts obtained by extraction of commercial pea flour from 2001 and 2003 with 80% methanol and 80% ethanol at reflux temperature (71-72° C. and 78-79° C.).

| | | 10:1 solvent to flour ratio | | | | | | 25:1 solvent to defatted flour ratio | | | | | |
|---|---|---|---|---|---|---|---|---|---|---|---|---|---|
| solvent/ extraction | | Peptides to internal | saponins to internal | EMW, g/100 g | rice weevil | | | Peptides to internal | saponins to internal | EMW, | rice weevil | | |
| Year | time (h) | standard ratio[a] | standard ratio[b] | of flour[c] | f.c. (%)[d] | $EC_{50}$ (%)[e] | $LC_{50}$ (%)[f] | standard ratio[a] | standard ratio[b] | g/100 g of flour[c] | f.c. (%)[d] | $EC_{50}$ (%)[e] | $LC_{50}$ (%)[f] |
| 2001 | MeOH 0.083 | 0.45 | 0.10 | 17.9 | 58 | 4.4 | 1.4 | 0.51 | 0.11 | 20.1 | 56 | 2.1 | 2.0 |
| 2001 | EtOH 0.083 | 0.51 | 0.19 | 14.4 | 48 | 2.6 | 1.2 | 0.70 | 0.17 | 17.3 | 58 | 2.7 | 1.8 |
| 2003 | MeOH 0.083[g] | 0.35 | 0.07 | 17.4 | 48 | 1.5 | 3.3 | 0.49 | 0.05 | 20.3 | 51 | 2.0 | 1.5 |
| | 0.5[g] | 0.35 | 0.16 | 16.8 | 48 | 2.4 | 7.4 | | | | | | |
| | 3.0[g] | <0.005 | 0.03 | 16.7 | 66 | 51 | 11.9 | | | | | | |
| 2003 | EtOH 0.083 | 0.55 | 0.11 | 16.1 | 43 | 0.8 | 5.1 | 0.66 | 0.11 | 17.9 | 52 | 1.6 | 1.0 |
| | 0.083[g] | 0.53 | 0.10 | 16.6 | 51 | 1.7 | 3.5 | | | | | | |
| | 0.5[g] | 0.39 | 0.11 | 14.6 | 48 | 1.6 | 3.6 | | | | | | |
| | 0.3[g] | <0.005 | 0.04 | 16.3 | 64 | 17 | 5.5 | | | | | | |
| | Reference C8 extract[h] | | | | | | | 15.40 | 0.37 | | 26 | 0.1 | 0.6 |

[a-f]See the corresponding footnotes of Table 27.
[g]A second 2003 batch of commercial pea flour, milled in July 2003, was utilized for these experiments.
[h]Obtained in powder form from defatted pea flour by hot 80% methanol extraction and C8 SepPak cartridges (Bodnaryk et al., 1999).

TABLE 29

Properties of precipitates from treatment of crude pea extracts from 2003 flour with an organic acid.

| crude extract (1 g) | HOAc (50 ml) | wash step | color | yield[a] (%) | peptide:saponin[b] | rice weevil[c] | | |
|---|---|---|---|---|---|---|---|---|
| | | | | | | f.c. (%) | $EC_{50}$ (%) | $LD_{50}$ (%) |
| EtOH, 5 min. reflux[d] | 1 M | none | brown powder | 8 | 3.1 to 1 | 39 | 0.8 | 0.7 |
| EtOH, 5 min. reflux[e] | 1 M | 1 M HOAc (20 ml) | viscous brown oil | 9 | 0.3 to 1 | 28 | 0.5 | 0.9 |
| EtOH, 5 min. reflux[d] | 3 M | 0.1 M HOAc (20 ml) | viscous brown oil | 20 | 0.25 to 1 | 46 | 1.3 | 1.0 |
| MeOH, 5 min. reflux[f] | 1 M | none | brown semi-solid | 28 | 1.8 to 1 | 45 | 0.9 | 1.3 |
| C8 Extract | | | | | | 23 | 0.4 | 0.2 |

[a]Isolated yield of (washed) precipitate from 1 g of crude extract.
[b]Ratio determined from the sum of HPLC peak areas for all detected peptides and all detected soyasaponins (C18 Symmetry column and evaporative light scattering detector). Electrospray LC/MS under acidic conditions with a C18 Symmetry column indicated that the precipitated peptides were of the methionine sulfoxide type (3805, 3757 and 3752 Da) whereas the main saponin was soyasaponin I. Late eluting phospholipids (lysolecithins) with molecular masses of 495, 519 and 521 Daltons were also found in quantity in the precipitate. Trace quantities of soyasaponin VI and dehydrosoyasaponin I were present.
[c]Bioassay conditions are described in the footnotes of Table 27.
[d]These extracts corresponded to the second entry under 2003 EtOH in Table 28.
[e]This extract corresponded to the first entry under 2003 EtOH in Table 28.
[f]This extract corresponded to the first entry under 2003 MeOH in Table 28.

All citations are hereby incorporated by reference.

The present invention has been described with regard to one or more embodiments. However, it will be apparent to persons skilled in the art that a number of variations and modifications can be made without departing from the scope of the invention as defined in the claims.

REFERENCES

Agilent Technologies. 2000. High pH stability with the resolution of silica PEAK, no. 1, p. 12.

Ahamed, A., S. Tsurumi, M. Ozaki and T. Amakawa. 2000. Chromosaponin I stimulates the sugar taste receptor of the blowfly, Phormia regina. Comp. Biochem. Physiol. A-Molecular and Integrative Physiology 125: 343-349.

Bodnaryk, R. P., P. G. Fields, Y. Xie and K. A. Fulcher. 1999. Insecticidal factor from field peas. U.S. Pat. No. 5,955,082 (filed Jan. 29, 1997).

Bonetto, V., A.-C. Bergman, H. Jornvall and R. Sillard. 1997. C-Terminal sequence analysis of peptides and proteins using carboxypeptidases and mass spectrometry after derivatization of lys and cys residues. Anal. Chem. 69: 1315-1319.

Brot, N. and H. Weissbach. 2000. Peptide methionine sulfoxide reductase: biochemistry and physiological role. Biopolymers 55: 288-296.

Brown, R. S. and J. J. Lennon. 1995. Sequence-specific fragmentation of matrix-assisted laser-desorbed protein/peptide ions. Anal. Chem. 67: 3990-3999.

Cammue, B. P. A., M. F.-C. De Bolle, F. R. G. Terras, P. Proost, J. Van Damme, S. B. Rees, J. Vanderleyden and W. F. Broekaert. 1992. Isolation and characterization of a novel class of plant antimicrobial peptides from *Mirabilis jalapa* L. seeds. J. Biol. Chem. 267: 2228-2233.

Ciorba, M. A., S. H. Heinemann, H. Weissbach, N. Brot and T. Hoshi. 1997. Modulation of potassium channel function by methionine oxidation and reduction. Proc. Natl. Acad. Sci. USA 94: 9932-9937.

Creighton, T. E. 1989. Disulphide bonds between cysteine residues in "Protein Structure, A Practical Approach" T. E. Creighton, ed., IRL Press, Oxford, p. 157.

Daveby, Y. D., P. Aman, J. M. Betz, S. M. Musser and W. R. Obermeyer. 1997. The variation in content and changes during development of soyasaponin I in dehulled Swedish peas (*Pisum sativum* L). J. Sci. Food Agric. 73: 391-395.

Daveby, Y. D., P. Aman, J. M. Betz and S. M. Musser. 1998. Effect of storage and extraction on ratio of soyasaponin I to 2,3-dihydro-2,5-dihydroxy-6-methyl-4-pyrone-conjugated soyasaponin I in dehulled peas (*Pisum sativum* L). J. Sci. Food Agric. 78: 141-146.

Delobel, B., A. Grenier, J. Gueguen, E. Ferrasson and M. Mbailao. 1999. Use of a polypeptide derived from PA1b legume albumin as insecticide. PCT WO99/58695 (filed May 7, 1998).

Ding, Y., T. Takeshita, L Yokoyama, J. Kinjo and T. Nohara. 1992. Triterpenoid glycosides from Sophorae subprostratae Radix. Chem. Pharm. Bull. 40: 139-142.

Dzwolak W, Ravindra R, and Winter R. 2004. Hydration and structure—the two sides of the insulin aggregation process. Phys. Chem. Chem. Phys. 6: 1938-1943.

Fried, B. and J. Sherma. 1994. "Thin-Layer Chromatography. Techniques and Applications" Third Edition, Marcel Dekker, Inc., New York, N.Y., pp. 133-156.

Gerard, J., R. Lloyd, T. Barsby, P. Haden, M. T. Kelly and R. J. Andersen. 1997. Massetolides A-H, antimycobacterial cyclic depsipeptides produced by two pseudomonads isolated from marine habitats. J. Nat. Prod. 60:223-229.

Gevaert, K. and J. Vandekerckhove. 2000. Protein identification methods in proteomics. Electrophoresis 21: 1145-1154.

Gressent, F., Rahioui, I. & Rahbe, Y. 2003. Characterization of a high-affinity binding site for the pea albumin 1b entomotoxin in the weevil *Sitophilus*. European Journal of Biochemistry 270, 2429-2435.

Gustavsson, N., U. Hamdahl, A. Emanuelsson, P. Roepstorff and C. Sundby. 1999. Methionine sulfoxidation of the chloroplast small heat shock protein and conformational changes in the oligomer. Protein Science 8: 2506-2512.

Haq S. K and R. H. Khan. 2003. Characterization of a proteinase inhibitor from Cajanus cajan (L.). J. Protein Chem. 22: 543-554.

Higgins, T. J. V., P. M. Chandler, P. J. Randall, D. Spencer, L. R. Beach, R. J. Blagrove, A. A. Kortt, and A. S. Inglis. 1986. Gene structure, protein structure, and regulation of the synthesis of a sulfur-rich protein in pea seeds. J. Biol. Chem. 261: 11124-11130.

Hostettmann, K. and A. Marston. 1995. Saponins. Cambridge University Press, Cambridge, UK p. 124.

Hu, J., S. Lee, S. Hendrich and P. A. Murphy. 2002. Quantification of the group B soyasaponins by high-performance liquid chromatography. J. Agric. Food Chem. 50: 2587-2594.

Iida, T., Y. Yoshiki, T. Kahara, K Okubo and H. Ohrui. 1997. A saponin conjugated with 2,3-dihydro-2,5-dihydroxy-9-methyl-4H-pyran-4-one from *Vigna angularis*. Phytochemistry 45: 1507-1509.

Imoto, T. and H. Yamada. 1989. Chemical modification. In Protein Function. A practical approach. T. E. Creighton, ed., IRL Press, Oxford, UK, p. 263.

Keough, T., R. S. Youngquist and M. P. Lacey. 1999. A method for high-sensitivity peptide sequencing using post-source decay matrix-assisted laser desorption ionization mass spectrometry. Proc. Natl. Acad. Sci. USA 96: 7131-7136.

Khaselev, N. and R. C. Murphy. 2000. Electrospray ionization mass spectrometry of lysoglycerophosphocholine lipid subclasses. J. Am. Soc. Mass Spectrom. 11: 283-291.

Kitagawa, I., M. Yoshikawa, Y. Imakura, and I. Yosioka. 1974. Saponin and Sapogenol. VIII. Photochemical Cleavage of Glycoside Linkage in Saponin. Photolysis of Some Saponins and Their Structural Features. Chem. Pharm. Bull. 22: 1339-1347.

Kitagawa, I., M. Yoshikawa, and 1. Yosioka. 1976. Saponin and Sapogenol. XIII. Structures of Three Soybean Saponins: Soyasaponin I, Soyasaponin II, and Soyasaponin III. Chem. Pharm. Bull. 24:121-129.

Kitagawa, I., T. Taniyama, T. Murakami, M. Yoshihara and M. Yoshikawa. 1988. Saponin and Sapogenol. XLVI. On the constituents in aerial part of American alfalfa, *Medicago sativa* L. The structure of dehydrosoyasaponin I. Yakugaku Zasshi 108: 547-554.

Konoshima, T., M. Kozuka, M. Haruna and K. Ito. 1991. Constituents of leguminous plants, XIII. New triterpenoid saponins from *Wistaria brachybotrys*. J. Nat. Prod. 54: 830-836.

Kubo, T., S. Hamada, T. Nohara, Z. Wang, H. Hirayama, K. Ikegami, K. Yasukawa, and M. Takido. 1989. Study on the Constituents of *Desmodium* styracifolium. Chem. Pharm. Bull. 37: 2229-2231.

Kudou, S., M. Tonomura, C. Tsukamoto, M. Shimoyamada, T. Uchida, and K. Okubo. 1992. Isolation and Structural Elucidation of the Major Genuine Soybean Saponin. Biosci. Biotech. Biochem. 56: 142-143.

Kudou, S., M. Tonomura, C. Tsukamoto, T. Uchida, T. Sakabe, N. Tamura, and K. Okubo. 1993. Isolation and Structural Elucidation of DDMP-Conjugated Soyasaponins as Genuine Saponins from Soybean Seeds. Biosci. Biotech. Biochem. 57: 546-550.

Larsen, M. R. and P. Roepstorff. 2000. Mass spectrometric identification of proteins and characterization of their post-translational modifications in proteome analysis. J. Anal. Chem. 366: 677-690.

Lee, M. R., C. M. Chen, B. H. Hwang and L. M. Hsu. 1999. Analysis of saponins from black bean by electrospray ionization and fast atom bombardment tandem mass spectrometry. J. Mass Spectrom. 34: 804-812.

Liu, J. L., K. V. Lu, T. Eris, V. Katta, K. R. Westcott, L. O, Narhi and H. S. Lu. 1998. In vitro methionine oxidation of recombinant human leptin. Pharm. Res. 15: 632-640.

Louis, S., B. Delobel, F. Gressent, I. Rahioui, L. Quillien, A. Vallier and Y. Rahbe. 2004. Molecular and biological screening for insect-toxic seed albumins from four legume species. Plant Science 167: 705-714.

Macko, S. A., M. E. Uhle, M. H. Engel and V. Andrusevich. 1997. Stable nitrogen isotope analysis of amino acid enantiomers by gas chromatography/combustion/isotope ratio mass spectrometry. Anal. Chem. 69: 926-929.

Manning, M. C., K. Patel and R. T. Borchardt. 1989. Stability of protein pharmaceuticals. Pharm. Res. 6: 903-918.

Marzilli, L. A., T. R. Golden, R. J. Cotter and A. S. Woods. 2000. Peptide sequence information derived by pronase digestion and ammonium sulfate in-source decay matrix-assisted laser desorption/ionization time-of-flight mass spectrometry. J. Am. Soc. Mass Spectrom. 11: 1000-1008.

Massiot, G., C. LaVaudi M. Benkhaled, and L. Le Men-Olivier. 1992. Soyasaponin V I, A New Maltol Conjugate from Alfalfa and Soybean. J. Nat. Prod. 55: 1339-1342.

McManus, O. B., G. H. Harris, K. M. Giangiacomo, P. Feigenbaum, J. P. Reuben, M. E. Addy, J. F. Burka, G. J. Kaczorowski, and M. L. Garcia 1993. An activator of calcium-dependent potassium channels isolated from a medicinal herb. Biochemistry 3: 6128-6133.

McManus, O. B., L. M. H. Helms, L. Pallanck, B. Ganetzky, R. Swanson and R. J. Leonard. 1995. Functional role of the β subunit of high conductance calcium-activated potassium channels. Neuron 14: 645-650.

Miyao, H., Y. Sakai, T. Takeshita, J. Kinjo and T. Nohara. 1996. Triterpene saponins from *Abrus cantoniensis* (Leguminosae). 1. Isolation and characterization of four new saponins and a new sapogenol. Chem. Pharm. Bull. 44: 1222-1227.

Muramoto, K. and H. Kamiya. 1987. Measurement of tryptophan in peptides by acid hydrolysis in the presence of phenol and its application to the amino acid sequence of a sea anemone toxin. Agr. Biol. Chem. 51: 1607-1616.

Pivec, V., J. Lachman and V. Rebakova. 1993. Flavonoids and saccharides in the seeds of lentil (*Lens esculenta* Moench.). Rostlinna Vyroba (Prague) 55: 65-72.

Rapala-Kozik, M., A. Kozik and J. Travis. 1998. Effect of oxidation of beta-amyloid precursor protein on its beta-secretase cleavage. A model study with synthetic peptides and candidate beta-secretases. J. Pept. Res. 52: 315-320.

Ruiz, R. G., K. R Price, A. E. Arthur, M. E. Rose, M. J. C. Rhodes and R. G. Fenwick. 1996. Effect of soaking and cooking on the saponin content and composition of chickpeas (*Cicer arietinum*) and lentils (*Lens culinaris*). J. Agric. Food Chem. 44: 1526-1530.

Schenck, H., G. P. Dado and S. H. Gellman. 1996. Redox-triggered secondary structure change in the aggregated states of a designed methionine-rich peptide. J. Am. Chem. Soc. 118: 12487-12494.

Schlittler, E. and J. Hohl. 1952. The alkaloids from *Strychnos meliononiana*. Helv. Chim. Acta 35: 29-45.

Sochaski, M. A., A. J. Jenkins, T. J. Lyons, S. R. Thorpe and J. W. Baynes. 2001. Isotope dilution gas chromatography/mass spectrometry method for the determination of methionine sulfoxide in protein. Anal. Chem. 73: 4662-4667.

Stahl, E. 1969. Thin Layer Chromatography. A Laboratory Handbook, 2nd ed., Springer-Verlag, New York, pp. 568-577.

Still, W. C., M. Kahn and A. Mitra. 1978. Rapid chromatographic technique for preparative separations with moderate resolution. J. Org. Chem. 43: 2923-2925.

Sun, Y. P. & Johnson, E. R. 1960. Analysis of joint action of insecticides against house flies. Journal of Economic Entomology 53, 887-892.

Taylor, W. G., Fields, P. G. & Sutherland, D. H. (2004a) Insecticidal components from field pea extracts: Soyasaponins and lysolecithins. Journal of Agricultural and Food Chemistry 52, 7484-7490.

Taylor, W. G., Fields, P. G. & Elder, J. E. (2004b) Insecticidal components from field pea extracts: Isolation and separation of peptide mixtures related to pea albumin 1b. Journal of Agricultural and Food Chemistry 52, 7491-7498.

Taylor, W. G., Sutherland, D. H., Olson, D. J. H., Ross, A. R. S. & Fields, P. G. (2004c) Insecticidal components from field pea extracts: Sequences of some variants of pea albumin 1b. Journal of Agricultural and Food Chemistry 52, 7499-7506.

Taylor, W. G., D. J. H. Olson, D. Sutherland, A. R. S. Ross and P. G. Fields. 2001. Differentiating 3788 Da Isoforms of Pea Albumin by Peptidase Digestion, MALDI-TOF MS and PSD Sequencing. Proceedings of the 49th ASMS Conference on Mass Spectrometry and Allied Topics.

Terras, F. R. G., H. M. E. Schoofs, M. F. C. DeBolle, F. Van Leuven, S. B. Rees, J. Vanderleyden, B. P. A. Cammue and W. F. Broekaert. 1992. Analysis of two novel classes of plant antifungal proteins from radish (*Raphanus sativus* L.) Seeds. J. Biol. Chem. 267: 15301-15309.

Tsurumi, S., T. Takagi, and T. Hashimoto. 1992. A γ-Pyronyl-triterpenoid Saponin from *Pisum sativum*. Phytochemistry 31: 2435-2438.

Tyler, R. T., C. G. Youngs and F. W. Sosulski. 1981. Air classification of legumes. 1. Separation efficiency, yield and composition of the starch and protein fractions. Cereal Chem. 58: 144-148.

Watanabe, Y., S. F. Barbashov, S. Komatsu, A. M. Hemmings, M. Miyagi, S. Tsunasawa and H. Hirano. 1994. A peptide that stimulates phosphorylation of the plant insulin-binding protein. Isolation, primary structure and cDNA cloning. Eur. J. Biochem. 224: 167-172.

Xiangyu, J., J. B. Smith and E. C. Abraham. 1996. Identification of a MS-MS fragment diagnostic for methionine sulfoxide. J. Mass Spectrom. 31: 1309-1310.

Xie, Y. S., R. P. Bodnaryk and P. G. Fields. 1996. A rapid and simple flour-disk bioassay for testing substances active against stored-product insects. The Canadian Entomologist 128: 865-875.

Yoshiki, Y., J. H. Kim and K. Okubo. 1994. Saponins conjugated with 2,3-dihydro-2,5-dihydroxy-6-methyl-4H-pyran-4-one from *Phaseolus coccineus*. Phytochemistry 36: 1009-1012.

What is claimed is:

1. A method of preparing acetic acid precipitated insecticidal components comprising:
   extracting a non-defatted or defatted legume seed material from *Pisum sativum* with an ethanol solution to obtain an insecticidal alcohol soluble legume extract;
   removing said ethanol from the insecticidal alcohol soluble legume extract;
   mixing the insecticidal alcohol soluble legume extract with an aqueous solution of acetic acid to reduce the pH and precipitate the insecticidal components; and
   isolating the acetic acid precipitated insecticidal components.

2. The method of claim 1, wherein the ethanol solution is an about 50-98% aqueous solution of the ethanol.

3. The method of claim 2, wherein the ethanol solution is an about 60-95% aqueous solution of the ethanol.

4. The method of claim 3, wherein the temperature of the aqueous ethanol is from 20° C. to 80° C.

5. The method of claim 1, wherein the mixing the insecticidal alcohol soluble legume extract with the acetic acid comprises mixing in a precipitation vessel containing said alcohol soluble legume extract with said acetic acid, wherein the concentration of the acetic acid in the vessel is 1-3M acetic acid.

6. The method of claim 4, wherein the temperature of the aqueous ethanol is from 40° C. to 80° C.

7. The method of claim 6, wherein the ethanol solution is about 80% ethanol.

8. The method of claim 7, further comprising re-extracting, evaporating, centrifuging, and/or drying the acetic acid precipitated insecticidal components.

* * * * *

SEQUENCE LISTING

```
<160> NUMBER OF SEQ ID NOS: 67

<210> SEQ ID NO 1
<211> LENGTH: 37
<212> TYPE: PRT
<213> ORGANISM: Pisum sativum
```

```
<400> SEQUENCE: 1

Ile Ser Cys Asn Gly Val Cys Ser Pro Phe Asp Ile Pro Pro Cys Gly
 1               5                  10                  15

Ser Pro Leu Cys Arg Cys Ile Pro Ala Gly Leu Val Ile Gly Asn Cys
                20                  25                  30

Arg Asn Pro Tyr Gly
            35

<210> SEQ ID NO 2
<211> LENGTH: 37
<212> TYPE: PRT
<213> ORGANISM: Pisum sativum

<400> SEQUENCE: 2

Ala Ser Cys Asn Gly Val Cys Ser Pro Phe Glu Met Pro Pro Cys Gly
 1               5                  10                  15

Thr Ser Ala Cys Arg Cys Ile Pro Tyr Gly Leu Phe Ile Gly Tyr Cys
                20                  25                  30

Arg Asn Pro Ser Gly
            35

<210> SEQ ID NO 3
<211> LENGTH: 37
<212> TYPE: PRT
<213> ORGANISM: Pisum sativum

<400> SEQUENCE: 3

Val Ser Cys Asn Gly Val Cys Ser Pro Phe Asp Ile Pro Pro Cys Gly
 1               5                  10                  15

Ser Pro Leu Cys Arg Cys Ile Pro Ala Gly Leu Val Ile Gly Lys Cys
                20                  25                  30

Arg Asn Pro Tyr Gly
            35

<210> SEQ ID NO 4
<211> LENGTH: 37
<212> TYPE: PRT
<213> ORGANISM: Pisum sativum

<400> SEQUENCE: 4

Ala Ser Cys Asn Gly Val Cys Ser Pro Phe Asp Ile Pro Pro Cys Gly
 1               5                  10                  15

Ser Pro Leu Cys Arg Cys Ile Pro Val Gly Leu Val Ile Gly Lys Cys
                20                  25                  30

Arg Asn Pro Tyr Gly
            35

<210> SEQ ID NO 5
<211> LENGTH: 37
<212> TYPE: PRT
<213> ORGANISM: Pisum sativum
<220> FEATURE:
<221> NAME/KEY: misc_feature
<222> LOCATION: (12)..(12)
<223> OTHER INFORMATION: Xaa is methionine sulfoxide

<400> SEQUENCE: 5

Ala Ser Cys Asn Gly Val Cys Ser Pro Phe Glu Xaa Pro Pro Cys Gly
 1               5                  10                  15

Ser Ser Ala Cys Arg Cys Ile Pro Val Gly Leu Val Val Gly Tyr Cys
                20                  25                  30
```

Arg His Pro Ser Gly
        35

<210> SEQ ID NO 6
<211> LENGTH: 37
<212> TYPE: PRT
<213> ORGANISM: Pisum sativum
<220> FEATURE:
<221> NAME/KEY: misc_feature
<222> LOCATION: (12)..(12)
<223> OTHER INFORMATION: Xaa is methionine sulfoxide

<400> SEQUENCE: 6

Ala Ser Cys Asn Gly Val Cys Ser Pro Phe Glu Xaa Pro Pro Cys Gly
1               5                   10                  15

Thr Ser Ala Cys Arg Cys Ile Pro Val Gly Leu Val Ile Gly Tyr Cys
            20                  25                  30

Arg Asn Pro Ser Gly
        35

<210> SEQ ID NO 7
<211> LENGTH: 37
<212> TYPE: PRT
<213> ORGANISM: Pisum sativum
<220> FEATURE:
<221> NAME/KEY: misc_feature
<222> LOCATION: (12)..(12)
<223> OTHER INFORMATION: Xaa is methionine sulfoxide

<400> SEQUENCE: 7

Ala Ser Cys Asn Gly Val Cys Ser Pro Phe Glu Xaa Pro Pro Cys Gly
1               5                   10                  15

Thr Ser Ala Cys Arg Cys Ile Pro Val Gly Leu Phe Ile Gly Tyr Cys
            20                  25                  30

Arg Asn Pro Ser Gly
        35

<210> SEQ ID NO 8
<211> LENGTH: 37
<212> TYPE: PRT
<213> ORGANISM: Pisum sativum

<400> SEQUENCE: 8

Ala Ser Cys Asn Gly Val Cys Ser Pro Phe Glu Met Pro Pro Cys Gly
1               5                   10                  15

Thr Ser Ala Cys Arg Cys Ile Pro Val Gly Leu Val Ile Gly Tyr Cys
            20                  25                  30

Arg Asn Pro Ser Gly
        35

<210> SEQ ID NO 9
<211> LENGTH: 37
<212> TYPE: PRT
<213> ORGANISM: Glycine max

<400> SEQUENCE: 9

Ala Asp Cys Asn Gly Ala Cys Ser Pro Phe Glu Val Pro Pro Cys Arg
1               5                   10                  15

Ser Arg Asp Cys Arg Cys Val Pro Ile Gly Leu Phe Val Gly Phe Cys
            20                  25                  30

Ile His Pro Thr Gly
        35

```
<210> SEQ ID NO 10
<211> LENGTH: 37
<212> TYPE: PRT
<213> ORGANISM: Artificial
<220> FEATURE:
<223> OTHER INFORMATION: possible sequence for PA1b variant

<400> SEQUENCE: 10

Ala Ser Cys Asn Gly Val Cys Ser Pro Phe Asp Met Pro Pro Cys Gly
1               5                   10

<220> FEATURE:
<223> OTHER INFORMATION: possible sequence for PA1b variant

<400> SEQUENCE: 14

Val Ser Cys Asn Gly Val Cys Ser Pro Phe Asp Ile Pro Pro Cys Gly
1               5                   10                  15

Thr Pro Ala Cys Arg Cys Ile Pro Val Gly Leu Val Ile Gly Lys Cys
            20                  25                  30

Arg Asn Pro Tyr Gly
            35

<210> SEQ ID NO 15
<211> LENGTH: 37
<212> TYPE: PRT
<213> ORGANISM: artificial
<220> FEATURE:
<223> OTHER INFORMATION: possible sequence for PA1b variant

<400> SEQUENCE: 15

Ile Ser Cys Asn Gly Val Cys Ser Pro Phe Glu Ile Pro Pro Cys Gly
1               5                   10                  15

Thr Pro Ala Cys Arg Cys Ile Pro Ala Gly Leu Val Ile Gly Lys Cys
            20                  25                  30

Arg Asn Pro Tyr Gly
            35

<210> SEQ ID NO 16
<211> LENGTH: 37
<212> TYPE: PRT
<213> ORGANISM: artificial
<220> FEATURE:
<223> OTHER INFORMATION: possible sequence for PA1b variant

<400> SEQUENCE: 16

Val Ser Cys Asn Gly Val Cys Ser Pro Phe Glu Ile Pro Pro Cys Gly
1               5                   10                  15

Ser Pro Ala Cys Arg Cys Ile Pro Val Gly Leu Val Ile Gly Lys Cys
            20                  25                  30

Arg Asn Pro Tyr Gly
            35

<210> SEQ ID NO 17
<211> LENGTH: 37
<212> TYPE: PRT
<213> ORGANISM: artificial
<220> FEATURE:
<223> OTHER INFORMATION: possible sequence for PA1b variant

<400> SEQUENCE: 17

Ala Ser Cys Asn Gly Val Cys Ser Pro Phe Asp Met Pro Pro Cys Gly
1               5                   10                  15

Ser Ser Ala Cys Arg Cys Ile Pro Val Gly Leu Phe Ile Gly Asn Cys
            20                  25                  30

Arg Asn Pro Tyr Gly
            35

<210> SEQ ID NO 18
<211> LENGTH: 37
<212> TYPE: PRT
<213> ORGANISM: artificial
<220> FEATURE:
<223> OTHER INFORMATION: possible sequence for PA1b variant

<400> SEQUENCE: 18

```
Val Ser Cys Asn Gly Val Cys Ser Pro Phe Asp Met Pro Pro Cys Gly
1               5                   10                  15

Ser Ser Ala Cys Arg Cys Ile Pro Ala Gly Leu Phe Ile Gly Asn Cys
            20                  25                  30

Arg Asn Pro Tyr Gly
            35
```

<210> SEQ ID NO 19
<211> LENGTH: 37
<212> TYPE: PRT
<213> ORGANISM: artificial
<220> FEATURE:
<223> OTHER INFORMATION: possible sequence for PA1b variant

<400> SEQUENCE: 19

```
Ala Ser Cys Asn Gly Val Cys Ser Pro Phe Glu Met Pro Pro Cys Gly
1               5                   10                  15

Thr Ser Ala Cys Arg Cys Ile Pro Ala Gly Leu Phe Ile Gly Asn Cys
            20                  25                  30

Arg Asn Pro Tyr Gly
            35
```

<210> SEQ ID NO 20
<211> LENGTH: 37
<212> TYPE: PRT
<213> ORGANISM: artificial
<220> FEATURE:
<223> OTHER INFORMATION: possible sequence for PA1b variant

<400> SEQUENCE: 20

```
Ile Ser C

Thr Pro Leu Cys Arg Cys Ile Pro Ala Gly Leu Val Ile Gly Asn Cys
            20                  25                  30

Arg Asn Pro Tyr Gly
        35

<210> SEQ ID NO 23
<211> LENGTH: 37
<212> TYPE: PRT
<213> ORGANISM: artificial
<220> FEATURE:
<223> OTHER INFORMATION: possible sequence for PA1b variant

<400> SEQUENCE: 23

Ile Ser Cys Asn Gly Val Cys Ser Pro Phe Glu Ile Pro Pro Cys Gly
1               5                   10                  15

Ser Pro Ala Cys Arg Cys Ile Pro Val Gly Leu Val Ile Gly Asn Cys
            20                  25                  30

Arg Asn Pro Tyr Gly
        35

<210> SEQ ID NO 24
<211> LENGTH: 37
<212> TYPE: PRT
<213> ORGANISM: artificial
<220> FEATURE:
<223> OTHER INFORMATION: possible sequence for PA1b variant

<400> SEQUENCE: 24

Ala Ser Cys Asn Gly Val Cys Ser Pro Phe Glu Ile Pro Pro Cys Gly

-continued

<210> SEQ ID NO 27
<211> LENGTH: 37
<212> TYPE: PRT
<213> ORGANISM: artificial
<220> FEATURE:
<223> OTHER INFORMATION: possible sequence for PA1b variant

<400> SEQUENCE: 27

Ile Ser Cys Asn Gly Val Cys Ser Pro Phe Asp Ile Pro Pro Cys Gly
1               5                   10                  15

Ser Pro Leu Cys Arg Cys Ile Pro Val Gly Leu Phe Ile Gly Asn Cys
            20                  25                  30

Arg

```
<211> LENGTH: 37
<212> TYPE: PRT
<213> ORGANISM: artificial
<220> FEATURE:
<223> OTHER INFORMATION: possible sequence for PA1b variant

<400> SEQUENCE: 31

Ile Ser Cys Asn Gly Val Cys Ser Pro Phe Asp Ile Pro Pro Cys Gly
1               5                   10                  15

Thr Pro Leu Cys Arg Cys Ile Pro Ala Gly Leu Phe Ile Gly Lys Cys
            20                  25                  30

Arg Asn Pro Ser Gly
        35

<210> SEQ ID NO 32
<211> LENGTH: 37
<212> TYPE: PRT
<213> ORGANISM: artificial
<220> FEATURE:
<223> OTHER INFORMATION: possible sequence for PA1b variant

<400> SEQUENCE: 32

Val Ser Cys Asn Gly Val Cys Ser Pro Phe Asp Ile Pro Pro Cys Gly
1               5                   10                  15

Ser Pro Leu Cys Arg Cys Ile Pro Val Gly Leu Phe Ile Gly Lys Cys
            20                  25                  30

Arg Asn Pro Ser Gly
        35

<210> SEQ ID NO 33
<211> LENGTH: 37
<212> TYPE: PRT
<213> ORGANISM: artificial
<220> FEATURE:
<223> OTHER INFORMATION: possible sequence for PA1b variant

<400> SEQUENCE: 33

Ile Ser Cys Asn Gly Val Cys Ser Pro Phe Glu Ile Pro Pro Cys Gly
1               5                   10                  15

Ser Pro Leu Cys Arg Cys Ile Pro Ala Gly Leu Phe Ile Gly Lys Cys
            20                  25                  30

Arg Asn Pro Ser Gly
        35

<210> SEQ ID NO 34
<211> LENGTH: 37
<212> TYPE: PRT
<213> ORGANISM: artificial
<220> FEATURE:
<223> OTHER INFORMATION: possible sequence for PA1b variant

<400> SEQUENCE: 34

Ile Ser Cys Asn Gly Val Cys Ser Pro Phe Glu Ile Pro Pro Cys Gly
1               5                   10                  15

Thr Pro Ala Cys Arg Cys Ile Pro Val Gly Leu Phe Ile Gly Lys Cys
            20                  25                  30

Arg Asn Pro Ser Gly
        35

<210> SEQ ID NO 35
<211> LENGTH: 37
<212> TYPE: PRT
<213> ORGANISM: artificial
<220> FEATURE:
```

```
<223> OTHER INFORMATION: possible sequence for PA1b variant

<400> SEQUENCE: 35

Ala Ser Cys Asn Gly Val Cys Ser Pro Phe Glu Ile Pro Pro Cys Gly
1               5                   10                  15

Thr Pro Leu Cys Arg Cys Ile Pro Val Gly Leu Phe Ile Gly Lys Cys
            20                  25                  30

Arg Asn Pro Ser Gly
            35

<210> SEQ ID NO 36
<211> LENGTH: 37
<212> TYPE: PRT
<213> ORGANISM: artificial
<220> FEATURE:
<223> OTHER INFORMATION: possible sequence for PA1b variant

<400> SEQUENCE: 36

Val Ser Cys Asn Gly Val Cys Ser Pro Phe Glu Ile Pro Pro Cys Gly
1               5                   10                  15

Thr Pro Leu Cys Arg Cys Ile Pro Ala Gly Leu Phe Ile Gly Lys Cys
            20                  25                  30

Arg Asn Pro Ser Gly
            35

<210> SEQ ID NO 37
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 37

Ala Ser Cys Asn Gly Val Cys Ser Pro Phe Glu Xaa Pro Pro Cys Gly
1               5                   10                  15

Ser Ser Leu Cys Arg Cys Ile Pro Ala Gly Leu Val Ile Gly Tyr Cys
            20                  25                  30

Arg Asn Pro Ser Gly
            35

<210> SEQ ID NO 38
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 38

Ala Ser Cys Asn Gly Val Cys Ser Pro Phe Asp Xaa Pro Pro Cys Gly
1               5                   10                  15

Thr Ser Leu Cys Arg Cys Ile Pro Ala Gly Leu Val Ile Gly Tyr Cys
            20                  25                  30

Arg Asn Pro Ser Gly
            35

<210> SEQ ID NO 39
```

```
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 39

Ile Ser Cys Asn Gly Val Cys Ser Pro Phe Glu Xaa Pro Pro Cys Gly
1               5                   10                  15

Ser Ser Ala Cys Arg Cys Ile Pro Ala Gly Leu Val Ile Gly Tyr Cys
            20                  25                  30

Arg Asn Pro Ser Gly
        35

<210> SEQ ID NO 40
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 40

Val Ser Cys Asn Gly Val Cys Ser Pro Phe Glu Xaa Pro Pro Cys Gly
1               5                   10                  15

Thr Ser Ala Cys Arg Cys Ile Pro Ala Gly Leu Val Ile Gly Tyr Cys
            20                  25                  30

Arg Asn Pro Ser Gly
        35

<210> SEQ ID NO 41
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 41

Ile Ser Cys Asn Gly Val Cys Ser Pro Phe Asp Xaa Pro Pro Cys Gly
1               5                   10                  15

Thr Ser Ala Cys Arg Cys Ile Pro Ala Gly Leu Val Ile Gly Tyr Cys
            20                  25                  30

Arg Asn Pro Ser Gly
        35

<210> SEQ ID NO 42
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 42
```

Val Ser Cys Asn Gly Val Cys Ser Pro Phe Asp Xaa Pro Pro Cys Gly
1               5                   10                  15

Ser Ser Ala Cys Arg Cys Ile Pro Val Gly Leu Val Ile Gly Tyr Cys
            20                  25                  30

Arg Asn Pro Ser Gly
            35

<210> SEQ ID NO 43
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 43

Ala Ser Cys Asn Gly Val Cys Ser Pro Phe Glu Xaa Pro Pro Cys Gly
1               5                   10                  15

Ser Ser Leu Cys Arg Cys Ile Pro Ala Gly Leu Phe Ile Gly Tyr Cys
            20                  25                  30

Arg Asn Pro Ser Gly
            35

<210> SEQ ID NO 44
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 44

Ala Ser Cys Asn Gly Val Cys Ser Pro Phe Asp Xaa Pro Pro Cys Gly
1               5                   10                  15

Thr Ser Leu Cys Arg Cys Ile Pro Ala Gly Leu Phe Ile Gly Tyr Cys
            20                  25                  30

Arg Asn Pro Ser Gly
            35

<210> SEQ ID NO 45
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 45

Ile Ser Cys Asn Gly Val Cys Ser Pro Phe Glu Xaa Pro Pro Cys Gly
1               5                   10                  15

Ser Ser Ala Cys Arg Cys Ile Pro Ala Gly Leu Phe Ile Gly Tyr Cys
            20                  25                  30

Arg Asn Pro Ser Gly
            35

```
<210> SEQ ID NO 46
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 46

Val Ser Cys Asn Gly Val Cys Ser Pro Phe Glu Xaa Pro Pro Cys Gly
1               5                   10                  15

Thr Ser Ala Cys Arg Cys Ile Pro Ala Gly Leu Phe Ile Gly Tyr Cys
            20                  25                  30

Arg Asn Pro Ser Gly
            35

<210> SEQ ID NO 47
<211> LENGTH: 37
<212> TYPE: PRT
<213> ORGANISM: artificial
<220> FEATURE:
<223> OTHER INFORMATION: possible sequence for PA1b variant

<400> SEQUENCE: 47

Ile Ser Cys Asn Gly Val Cys Ser Pro Phe Glu Ile Pro Pro Cys Gly
1               5                   10                  15

Thr Pro Leu Cys Arg Cys Ile Pro Ala Gly Leu Val Ile Gly Tyr Cys
            20                  25                  30

Arg Asn Pro Ser Gly
            35

<210> SEQ ID NO 48
<211> LENGTH: 37
<212> TYPE: PRT
<213> ORGANISM: Artificial
<220> FEATURE:
<223> OTHER INFORMATION: possible sequence for PA1b variant

<400> SEQUENCE: 48

Val Ser Cys Asn Gly Val Cys Ser Pro Phe Glu Ile Pro Pro Cys Gly
1               5                   10                  15

Ser Pro Leu Cys Arg Cys Ile Pro Val Gly Leu Val Ile Gly Tyr Cys
            20                  25                  30

Arg Asn Pro Ser Gly
            35

<210> SEQ ID NO 49
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 49

Ile Ser Cys Asn Gly Val Cys Ser Pro Phe Asp Xaa Pro Pro Cys Gly
1               5                   10                  15

Thr Ser Ala Cys Arg Cys Ile Pro Ala Gly Leu Phe Ile Gly Tyr Cys
            20                  25                  30
```

Arg Asn Pro Ser Gly
        35

<210> SEQ ID NO 50
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 50

Val Ser Cys Asn Gly Val Cys Ser Pro Phe Asp Xaa Pro Pro Cys Gly
1               5                   10                  15

Ser Ser Ala Cys Arg Cys Ile Pro Val Gly Leu Phe Ile Gly Tyr Cys
            20                  25                  30

Arg Asn Pro Ser Gly
        35

<210> SEQ ID NO 51
<211> LENGTH: 37
<212> TYPE: PRT
<213> ORGANISM: Artificial
<220> FEATURE:
<223> OTHER INFORMATION: possible sequence for PA1b variant

<400> SEQUENCE: 51

Ile Ser Cys Asn Gly Val Cys Ser Pro Phe Asp Ile Pro Pro Cys Gly
1               5                   10                  15

Ser Pro Leu Cys Arg Cys Ile Pro Val Gly Leu Val Ile Gly Tyr Cys
            20                  25                  30

Arg Asn Pro Ser Gly
        35

<210> SEQ ID NO 52
<211> LENGTH: 37
<212> TYPE: PRT
<213> ORGANISM: Artificial
<220> FEATURE:
<223> OTHER INFORMATION: possible sequence for PA1b variant

<400> SEQUENCE: 52

Val Ser Cys Asn Gly Val Cys Ser Pro Phe Asp Ile Pro Pro Cys Gly
1               5                   10                  15

Thr Pro Leu Cys Arg Cys Ile Pro Val Gly Leu Val Ile Gly Tyr Cys
            20                  25                  30

Arg Asn Pro Ser Gly
        35

<210> SEQ ID NO 53
<211> LENGTH: 37
<212> TYPE: PRT
<213> ORGANISM: Artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 53

Ala Ser Cys Asn Gly Val Cys Ser Pro Phe Glu Xaa Pro Pro Cys Gly
1               5                   10                  15

Thr Ser Ala Cys Arg Cys Ile Pro Ala Gly Leu Val Ile Gly Tyr Cys
            20                  25                  30

Arg Asn Pro Tyr Gly
        35

<210> SEQ ID NO 54
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 54

Ala Ser Cys Asn Gly Val Cys Ser Pro Phe Asp Xaa Pro Pro Cys Gly
1               5                   10                  15

Ser Ser Ala Cys Arg Cys Ile Pro Val Gly Leu Val Ile Gly Tyr Cys
            20                  25                  30

Arg Asn Pro Tyr Gly
        35

<210> SEQ ID NO 55
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 55

Val Ser Cys Asn Gly Val Cys Ser Pro Phe Asp Xaa Pro Pro Cys Gly
1               5                   10                  15

Ser Ser Ala Cys Arg Cys Ile Pro Ala Gly Leu Val Ile Gly Tyr Cys
            20                  25                  30

Arg Asn Pro Tyr Gly
        35

<210> SEQ ID NO 56
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 56

Ala Ser Cys Asn Gly Val Cys Ser Pro Phe Asp Xaa Pro Pro Cys Gly
1               5                   10                  15

Thr Ser Ala Cys Arg Cys Ile Pro Val Gly Leu Val Val Gly Tyr Cys
            20                  25                  30

Arg His Pro Ser Gly
        35

<210> SEQ ID NO 57
<211> LENGTH: 37
<212> TYPE: PRT

-continued

```
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 57

Ala Ser Cys Asn Gly Val Cys Ser Pro Phe Asp Xaa Pro Pro Cys Gly
1               5                   10                  15

Ser Ser Leu Cys Arg Cys Ile Pro Ala Gly Leu Val Val Gly Tyr Cys
            20                  25                  30

Arg His Pro Ser Gly
        35

<210> SEQ ID NO 58
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 58

Val Ser Cys Asn Gly Val Cys Ser Pro Phe Glu Xaa Pro Pro Cys Gly
1               5                   10                  15

Ser Ser Ala Cys Arg Cys Ile Pro Ala Gly Leu Val Val Gly Tyr Cys
            20                  25                  30

Arg His Pro Ser Gly
        35

<210> SEQ ID NO 59
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 59

Val Ser Cys Asn Gly Val Cys Ser Pro Phe Asp Xaa Pro Pro Cys Gly
1               5                   10                  15

Thr Ser Ala Cys Arg Cys Ile Pro Ala Gly Leu Val Val Gly Tyr Cys
            20                  25                  30

Arg His Pro Ser Gly
        35

<210> SEQ ID NO 60
<211> LENGTH: 37
<212> TYPE: PRT
<213> ORGANISM: artificial
<220> FEATURE:
<223> OTHER INFORMATION: possible sequence for PA1b variant
<220> FEATURE:
<221> NAME/KEY: misc_feature
<222> LOCATION: (12)..(12)
<223> OTHER INFORMATION: Xaa is methionine sulfoxide

<400> SEQUENCE: 60

Ile Ser Cys Asn Gly Val Cys Ser Pro Phe Asp Xaa Pro Pro Cys Gly
```

-continued

```
               1               5                  10                 15
Ser Ser Ala Cys Arg Cys Ile Pro Ala Gly Leu Val Val Gly Tyr Cys
               20                 25                 30
Arg His Pro Ser Gly
               35

<210> SEQ ID NO 61
<211> LENGTH: 12
<212> TYPE: PRT
<213> ORGANISM: artificial
<220> FEATURE:
<223> OTHER INFORMATION: possible sequence for PA1b variant

<400> SEQUENCE: 61

Cys Ile Pro Val Gly Leu Val Ile Gly Tyr Cys Arg
1               5                  10

<210> SEQ ID NO 62
<211> LENGTH: 12
<212> TYPE: PRT
<213> ORGANISM: artificial
<220> FEATURE:
<223> OTHER INFORMATION: possible sequence for PA1b variant

<400> SEQUENCE: 62

Cys Ile Pro Val Gly Leu Phe Ile Gly Tyr Cys Arg
1               5                  10

<210> SEQ ID NO 63
<211> LENGTH: 21
<212> TYPE: PRT
<213> ORGANISM: artificial
<220> FEATURE:
<223> OTHER INFORMATION: concensus sequence
<220> FEATURE:
<221> NAME/KEY: misc_feature
<222> LOCATION: (2)..(2)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (3)..(3)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (5)..(5)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (7)..(7)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (8)..(8)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (11)..(11)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (12)..(12)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (14)..(14)
<223> OTHER INFORMATION: Xaa equals (X)n where each X is independently
``` selected from any amino acid and n equals 1, 2, 3, 4 or 5
<220> FEATURE:
<221> NAME/KEY: misc_feature
<222> LOCATION: (16)..(16)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (18)..(18)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (19)..(19)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (20)..(20)
<223> OTHER INFORMATION: Xaa equals (X)n where each X is independently
      selected from any amino acid and n equals 1, 2, 3, 4 or 5

<400> SEQUENCE: 63

Cys Xaa Xaa Cys Xaa Pro Xaa Xaa Pro Cys Xaa Xaa Cys Xaa Cys Xaa
1               5                  10                  15

Pro Xaa Xaa Xaa Cys
            20

<210> SEQ ID NO 64
<211> LENGTH: 24
<212> TYPE: PRT
<213> ORGANISM: artificial
<220> FEATURE:
<223> OTHER INFORMATION: concensus sequence
<220> FEATURE:
<221> NAME/KEY: misc_feature
<222> LOCATION: (2)..(2)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (3)..(3)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (5)..(5)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (7)..(7)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (8)..(8)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (12)..(12)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (13)..(13)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (15)..(15)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (17)..(17)

```
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (19)..(19)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (20)..(20)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (21)..(21)
<223> OTHER INFORMATION: Xaa equals (X)n where each X is independently
      selected from any amino acid and n equals 1, 2, 3, 4 or 5
<220> FEATURE:
<221> NAME/KEY: misc_feature
<222> LOCATION: (23)..(23)
<223> OTHER INFORMATION: Xaa equals (X)n where each X is independently
      selected from any amino acid and n equals 1, 2, 3, 4 or 5

<400> SEQUENCE: 64

Cys Xaa Xaa Cys Xaa Pro Xaa Xaa Pro Pro Cys Xaa Xaa Cys Xaa Cys
1               5                   10                  15

Xaa Pro Xaa Xaa Xaa Cys Xaa Pro
            20

<210> SEQ ID NO 65
<211> LENGTH: 30
<212> TYPE: PRT
<213> ORGANISM: artificial
<220> FEATURE:
<223> OTHER INFORMATION: concensus sequence
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (6)..(6)
<223> OTHER INFORMATION: Xaa can be any amino acid
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (11)..(11)
<223> OTHER INFORMATION: Xaa can be any amino acid
<220> FEATURE:
<221> NAME/KEY: misc_feature
<222> LOCATION: (14)..(14)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
```

```
<220> FEATURE:
<221> NAME/KEY: misc_feature
<222> LOCATION: (16)..(16)
<223> OTHER INFORMATION: Xaa can be any amino acid
<220> FEATURE:
<221> NAME/KEY: misc_feature
<222> LOCATION: (17)..(17)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (19)..(19)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (23)..(23)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (25)..(25)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature
<222> LOCATION: (29)..(29)
<223> OTHER INFORMATION: Xaa equals (X)n where each X is independently
      selected from any amino acid and n equals 0, 1, 2, 3, or 4

<400> SEQUENCE: 65

Cys Xaa Xaa Xaa Cys Xaa Pro Xaa Xaa Xaa Xaa Pro Cys Xaa Xaa Xaa
1               5                   10                  15

Xaa Cys Xaa Cys Xaa Pro Xaa Xaa Xaa Xaa Xaa Xaa Cys
            20                  25                  30

<210> SEQ ID NO 66
<211> LENGTH: 33
<212> TYPE: PRT
<213> ORGANISM: artificial
<220> FEATURE:
<223> OTHER INFORMATION: concensus sequence
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (6)..(6)
<223> OTHER INFORMATION: Xaa can be any amino acid
```

```
<220> FEATURE:
<221> NAME/KEY: misc_feature
<222> LOCATION: (8)..(8)
<223> OTHER INFORMATION: Xaa can be any amino acid
<220> FEATURE:
<221> NAME/KEY: misc_feature
<222> LOCATION: (9)..(9)
<223> OTHER INFORMATION: Xaa equals (X)n where each X is independently
      selected from any amino acid and  n equals 0, 1, 2, 3, or 4
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (14)..(14)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (16)..(16)
<223> OTHER INFORMATION: Xaa can be any amino acid
<220> FEATURE:
<221> NAME/KEY: misc_feature
<222> LOCATION: (17)..(17)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (19)..(19)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (23)..(23)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (25)..(25)
<223> OTHER INFORMATION: Xaa can be any amino acid
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa can be any amino acid
<220> FEATURE:
<221> NAME/KEY: misc_feature
<222> LOCATION: (28)..(28)
<223> OTHER INFORMATION: Xaa can be any amino acid
<220> FEATURE:
<221> NAME/KEY: misc_feature
<222> LOCATION: (29)..(29)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (31)..(31)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (32)..(32)
<223> OTHER INFORMATION: Xaa can be any amino acid

<400> SEQUENCE: 66
```

```
Cys Xaa Xaa Xaa Cys Xaa Pro Xaa Xaa Xaa Pro Pro Cys Xaa Xaa Xaa
1               5                   10                  15

Xaa Cys Xaa Cys Xaa Pro Xaa Xaa Xaa Xaa Xaa Xaa Cys Xaa Xaa
        20                  25                  30

Pro

<210> SEQ ID NO 67
<211> LENGTH: 33
<212> TYPE: PRT
<213> ORGANISM: artificial
<220> FEATURE:
<223> OTHER INFORMATION: concensus sequence
<220> FEATURE:
<221> NAME/KEY: misc_feature
<222> LOCATION: (2)..(2)
<223> OTHER INFORMATION: Xaa can be any amino acid
<220> FEATURE:
<221> NAME/KEY: misc_feature
<222> LOCATION: (3)..(3)
<223> OTHER INFORMATION: Xaa can be any amino acid
<220> FEATURE:
<221> NAME/KEY: misc_feature
<222> LOCATION: (4)..(4)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (9)..(9)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (10)..(10)
<223> OTHER INFORMATION: Xaa can be any amino acid
<220> FEATURE:
<221> NAME/KEY: misc_feature
<222> LOCATION: (14)..(14)
<223> OTHER INFORMATION: Xaa can be any amino acid
<220> FEATURE:
<221> NAME/KEY: misc_feature
<222> LOCATION: (15)..(15)
<223> OTHER INFORMATION: Xaa can be any amino acid
<220> FEATURE:
<221> NAME/KEY: misc_feature
<222> LOCATION: (16)..(16)
<223> OTHER INFORMATION: Xaa can be any amino acid
<220> FEATURE:
<221> NAME/KEY: misc_feature
<222> LOCATION: (17)..(17)
<223> OTHER INFORMATION: Xaa can be any amino acid
<220> FEATURE:
<221> NAME/KEY: misc_feature
<222> LOCATION: (19)..(19)
<223> OTHER INFORMATION: Xaa can be any amino acid
<220> FEATURE:
<221> NAME/KEY: misc_feature
<222> LOCATION: (21)..(21)
<223> OTHER INFORMATION: Xaa can be any amino acid
<220> FEATURE:
<221> NAME/KEY: misc_feature
<222> LOCATION: (23)..(23)
<223> OTHER INFORMATION: Xaa can be any amino acid
<220> FEATURE:
<221> NAME/KEY: misc_feature
<222> LOCATION: (24)..(24)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (26)..(26)
<223> OTHER INFORMATION: Xaa can be any amino acid
<220> FEATURE:
<221> NAME/KEY: misc_feature
<222> LOCATION: (27)..(27)
<223> OTHER INFORMATION: Xaa equals (X)n where each X is independently
      selected from any amino acid and n equals 0, 1, 2, 3, or 4
<220> FEATURE:
```

```
-continued

<221> NAME/KEY: misc_feature
<222> LOCATION: (29)..(29)
<223> OTHER INFORMATION: Xaa can be any amino acid
<220> FEATURE:
<221> NAME/KEY: misc_feature
<222> LOCATION: (31)..(31)
<223> OTHER INFORMATION: Xaa equals (X)n where each X is independently
      selected from any amino acid and n equals 0, 1, 2, 3, or 4
<220> FEATURE:
<221> NAME/KEY: misc_feature
<222> LOCATION: (32)..(32)
<223> OTHER INFORMATION: Xaa can be any amino acid

<400> SEQUENCE: 67

Cys Xaa Xaa Xaa Cys Ser Pro Phe Xaa Xaa Pro Pro Cys Xaa Xaa Xaa
1               5                   10                  15

Xaa Cys Xaa Cys Xaa Pro Xaa Xaa Leu Xaa Xaa Gly Xaa Cys Xaa Xaa
            20                  25                  30

Pro
```